United States Patent [19]

Schneider et al.

[11] Patent Number: 5,456,256
[45] Date of Patent: Oct. 10, 1995

[54] HIGH RESOLUTION ULTRASONIC IMAGING APPARATUS AND METHOD

[75] Inventors: John K. Schneider, Snyder; Frank W. Keeney, Williamsville; Russell J. Drakes, Cheektowaga; Stephen M. Gojevic, Buffalo; Nicholas G. Leszczynski, Amherst; Mark C. Schneider, East Amherst; Darold C. Wobschall, Williamsville, all of N.Y.

[73] Assignee: Ultra-Scan Corporation, Amherst, N.Y.

[21] Appl. No.: 147,027

[22] Filed: Nov. 4, 1993

[51] Int. Cl.⁶ .................................................. A61B 8/00
[52] U.S. Cl. .......................... 128/660.09; 128/662.03
[58] Field of Search .................. 128/660.04, 660.07, 128/660.08, 660.09, 662.03, 663.01, 660.06, 653.1; 382/4, 5

[56] References Cited

U.S. PATENT DOCUMENTS

| | | | |
|---|---|---|---|
| 4,048,986 | 9/1977 | Ott | 128/653.1 |
| 4,202,215 | 5/1980 | Meyer | 128/660.06 |
| 4,325,381 | 4/1982 | Glenn | 128/660 |
| 4,341,120 | 7/1982 | Anderson | 128/660.09 |
| 4,385,831 | 5/1983 | Ruell | 356/71 |
| 4,545,385 | 10/1985 | Pirschel | 128/660.09 |
| 4,637,256 | 1/1987 | Sugiyama et al. | 128/660.09 |
| 4,787,393 | 11/1988 | Fukukita et al. | 128/660.04 |
| 4,977,601 | 12/1990 | Bicz | 382/4 |
| 5,040,225 | 8/1991 | Gouge | 128/660.04 |
| 5,224,174 | 6/1993 | Schneider et al. | 382/5 |
| 5,235,982 | 8/1993 | O'Donnell | 128/660.07 |
| 5,258,922 | 11/1993 | Grill | 382/4 |

*Primary Examiner*—George Manuel
*Attorney, Agent, or Firm*—Hodgson, Russ, Andrews, Woods & Goodyear

[57] ABSTRACT

An ultrasonic imaging system and method for imaging human or animal tissue having a surface and including a probe including a platen for supporting the human or animal tissue for imaging the same, a transducer positioned closely adjacent the supporting means for providing an output ultrasonic beam directed on the surface so that the size of the beam at its focal point is as small as possible to maximize the resolution of the system and a mechanism for moving the transducer in two directions so as to provide a two dimensional scan of the surface by the ultrasonic beam. There is also provided a scan controller operatively connected to the probe for controlling the mechanism to provide the scan of the surface and a signal processor operatively connected to the probe for receiving signals produced in response to the scan of the surface and for processing the signals. In a form of mechanism wherein an oscillatory motor moves the transducer to direct the ultrasonic beam along an arcuate path, there is provided an encoder operatively associated with the motor for providing information on the amount of angular rotation provided by the motor. There is also provided an oscillatory flexible liquid impervious seal between the motor shaft and a liquid filled region containing the transducer in a manner causing minimal drag on the motor. The system and method can be employed in fingerprint scanning and processing, and in biometric identification and verification systems wherein the imaging system is utilized in combination with a record member containing a recorded biometric image and a processor for performing comparisons.

94 Claims, 31 Drawing Sheets

NOTE: LABELS ON RIGHT HAND SIDE OF CONTROL FLOW SYMBOL INDICATE SUBROUTINE NAME.

NOTE: LABELS ON RIGHT HAND SIDE OF CONTROL FLOW SYMBOL INDICATE SUBROUTINE NAME.

NOTE: LABELS ON RIGHT HAND SIDE OF CONTROL FLOW SYMBOL INDICATE SUBROUTINE NAME.

NOTE: LABELS ON RIGHT HAND SIDE OF CONTROL FLOW SYMBOL INDICATE SUBROUTINE NAME.

HIGH RESOLUTION ULTRASONIC IMAGING APPARATUS AND METHOD

BACKGROUND OF THE INVENTION

This invention relates to the art of surface scanning and imaging, and more particularly to a new and improved ultrasonic method and apparatus for surface scanning and imaging.

One area of use of the present invention is in fingerprint scanning and imaging, although the principles of the present invention can be variously applied to scanning and imaging subdermal and other biometric structures. The quality of the images obtained using ultrasound technology is superior as compared to those obtained using optical technology since the ultrasonic images are less dependent on the surface condition of the finger. As a result, by using ultrasound technology, individuals with very dry or very oily fingers, contaminated fingers or fingers having irregular ridge surfaces are able to be imaged equally as well.

In providing an ultrasonic method and apparatus for scanning and imaging fingerprints, subdermal and other biometric structures, an important consideration is that the resolution of the system and hence the resulting images be as high as possible. Another important consideration is that the scanning be performed as quickly as possible so as to minimize delay and inconvenience and avoid any discomfort to the individual.

SUMMARY OF THE INVENTION

It is, therefore, a primary object of this invention to provide a new and improved ultrasonic method and apparatus for imaging human and animal tissue.

It is a more particular object of this invention to provide such a method and apparatus which results in high resolution images.

It is a further object of this invention to provide such a method and apparatus wherein scanning is performed at a very fast rate.

The present invention provides an ultrasonic imaging system and method for imaging human or animal tissue having a surface and including probe means including means for defining the surface in a manner supporting the human or animal tissue for imaging the same, transducer means positioned closely adjacent the supporting means for providing an output ultrasonic beam directed on the surface so that the size of the beam at its focal point is as small as possible to maximize the resolution of the system and motive means for moving the transducer means in two directions so as to provide a two dimensional scan of the surface by the ultrasonic beam. There is also provided scan controller means operatively connected to the probe means for controlling the motive means to provide the scan of the surface and signal processor means operatively connected to the probe means for receiving signals produced in response to the scan of the surface and for processing the signals. In a form of motive means wherein an oscillatory motor moves the transducer means to direct the ultrasonic beam along an arcuate path, there is provided encoder means operatively associated with the motor for providing information on the amount of angular rotation provided by the motor. There is also provided an oscillatory flexible liquid impervious seal between the motor shaft and a liquid filled region containing the transducer means in a manner causing minimal drag on the motor. A plurality of transducers can be arranged along the aforementioned arcuate path to increase the speed of scanning. Another form of motive means operates on controlled release of stored mechanical energy. The system and method can be employed in fingerprint scanning and processing, and in biometric identification and verification systems wherein the imaging system is utilized in combination with a record member containing a recorded biometric image and a processor for performing comparisons. A plurality of transducer elements can be arranged in a linear array or in a two dimensional phased array with electronic focusing and steering of the ultrasonic beams. In fingerprint imaging the finger can be scanned from one edge of the fingernail to the other by placing the finger in a curved platen and moving the transducer means relative thereto or by rolling the finger on a flat platen associated with the above mentioned two dimensional phased array or providing a curved platen with the array associated therewith.

The foregoing and additional advantages and characterizing features of the present invention will become clearly apparent upon a reading of the ensuing detailed description together with the included drawing wherein:

BRIEF DESCRIPTION OF THE DRAWING FIGURES

DETAILED DESCRIPTION OF THE ILLUSTRATED EMBODIMENTS

Figure 1:
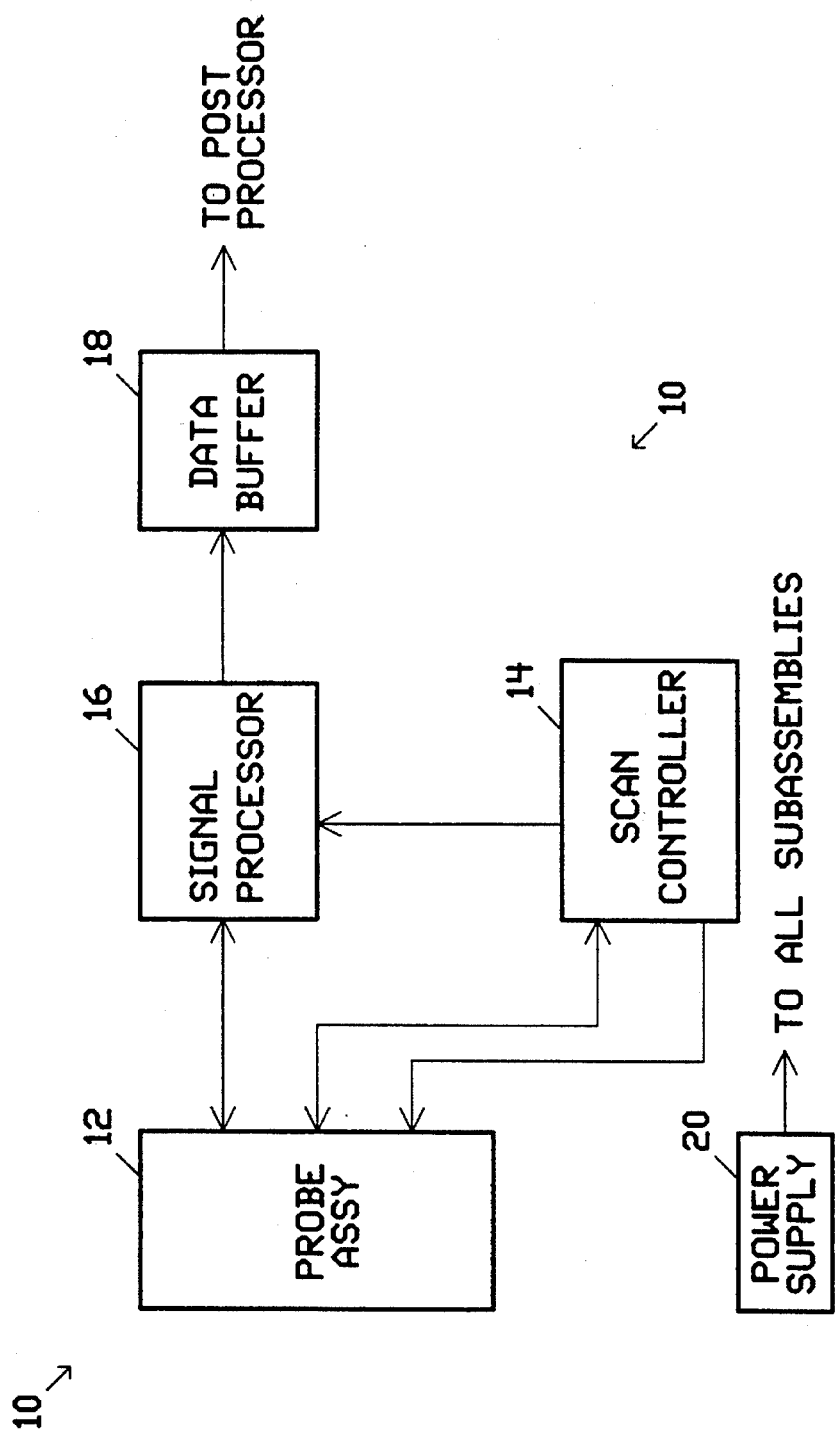
FIG. 1 is a block diagram of the ultrasonic imaging system according to the present invention.

An ultrasonic imaging system 10 according to the present invention is shown in FIG. 1. A probe assembly 12 is the part of the system that is responsible for the motion of a transducer in order to obtain a two dimensional scan window, typically having dimensions of 0.75"×0.75" for fingerprint imaging. The motion of probe assembly 12 is controlled by electronics of a scan controller 14. The scan controller 14 contains the necessary motor driver logic needed to drive the motors of the probe assembly 12 in a manner which will be described. The data out of the transducer of the probe assembly 12 is then received by a signal processor 16 where amplification, range gating, peak detection and A/D conversion take place. This data is then stored in a high speed data buffer random access memory 18 which is interfaced to any device suitable for receiving and processing the raw fingerprint data. A device such as a general purpose computer or custom fingerprint image processor could be used for this purpose. All of the system components or subassemblies are powered by a custom power supply 20 which provides the necessary voltages for operating the system. Each of the components will be described in further detail presently.

One of the applications for the technology of the system of FIG. 1 is obtaining dermatoglyphics or images of the friction skin surface of the finger, namely the fingerprint. The quality of the images obtained using ultrasound technology over optical technology is superior since these images are less dependent on the surface condition of the finger. This is discussed in detail in U.S. Pat. No. 5,224,174 issued Jun. 29, 1993 and entitled Surface Feature Mapping Using High Resolution C-Scan Ultrasonography, the disclosure of which is hereby incorporated by reference. As a result, individuals with very dry or very oily fingers, contaminated fingers or fingers having irregular ridge surfaces are able to be imaged equally as well. In order to obtain high quality fingerprint images, it has been determined according to the present invention that it is critical that the spot size of the transducer be very small, nominally 0.002" in diameter. This spot size is directly related to the resolving power of the system. In order to obtain a spot size of this diameter, a transducer must be built with the proper ratio of aperture, frequency and focal length. It has been found according to the present invention that a frequency of approximately 30 MHz is optimum with an overall element aperture of approximately 0.180" and a focal length of approximately 0.25". The ultrasonic method and apparatus according to the present invention can be used to scan other human and animal tissue surfaces such as palms, toes and the like.

A second fundamental advantage in the use of ultrasound for fingerprint imaging is using subdermal features that are found within the finger to reproduce the friction skin image. This is useful when the ridge detail on the outer surface of the finger has been temporarily modified such as by small cuts, destroyed altogether, or is not discernible due to excessive wear. The immediate underside of the skin contains all of the detail that the surface friction skin does; therefore, by imaging the immediate underside of the epidermis, a fingerprint image can be obtained free from any defects that might be present on the outer surface of the finger. The second or dermal layer of skin also contains artifacts that correspond to the dermatoglyphics of the friction skin. This layer of skin is composed of structures known as dermal papillae which are arranged in double rows where each row lies in a ridge of the epidermal layer. The only modification in the system of FIG. 1 that is required to obtain the subdermal images just below the epidermis is to process the ultrasonic signals returned from this depth and not the surface. This is accomplished by adjusting a range gate. The range gate is a window used to allow a particular portion of the return signal to propagate to the signal processing electronics; therefore, delaying the range gate in time corresponds to imaging deeper into the finger. This will be described in further detail presently.

This technique of subdermal imaging could prove particularly useful for those individuals whose friction skin lacks sufficient detail for analysis. This includes individuals who have undergone some form of trauma to the finger or hand, ranging from the very minor such as small cuts on the surface of the finger to the more severe such as burn victims. This technique would also prove beneficial in imaging others whose occupation tends to wear the ridge structure off from the surface of the finger. Since together these groups of individuals represent a significant percentage of the population, other devices that cannot image below the surface of the finger, such as the optical fingerprint readers, are at a clear performance disadvantage.

A third potential for the application of the technology of the system of FIG. 1 lies in the development of an entirely new biometric. It is well known that blood vessel patterns throughout the body have been used as a means of personal identification. Generally, the techniques that must be employed no obtain these images are deemed intrusive by the user and therefore such techniques generally do not succeed in a commercial mass market environment. The system described herein has the capability to penetrate well beneath the surface of the finger and image blood vessels and other subdermal structures. These structures are highly numerous and contain sufficient information to positively identify an individual. An entirely new biometric could be developed with the expectation that this biometric could prove to be much simpler in the post processing necessary to identify an individual using the fingerprint. The simplicity results in higher processing throughputs, greater accuracy, and lower system complexity, which in turn results in reduced system cost. In order to image this deep within the finger, a lower frequency transducer must be used. It has been found according to the present invention that frequencies of approximately 15 MHz are optimum due to their ability to penetrate deeper into the finger with less attenuation.

The various components or subassemblies of the system of FIG. 1 now will be described in detail. The probe means or assembly 12 comprises means in the form of a platen 30 for defining a surface 32 in a manner supporting human or animal tissue for imaging the same, transducer means 34 for providing an output ultrasonic beam and means generally designated 36 for positioning transducer means 34 closely adjacent supporting means 30 in a manner directing the ultrasonic beam on the surface 32 and so that the size of the beam at its focal point is as small as possible to maximize the resolution of the system. The positioning means 36, in turn, includes first means 38 for moving transducer 34 to direct the ultrasonic beam along the surface 32 in a first direction and second means 40 for moving transducer means 34 to direct the beam along the surface in a second direction. The first direction is into and out of the plane of the paper as viewed in FIG. 2 and the second direction is in the plane of the paper from left to right as viewed in FIG. 2. In the probe assembly shown, the first means 38 comprises motor means for oscillating transducer 34 to move the ultrasonic beam in an arcuate path along surface 32, and the second means 40 comprises motor means for moving transducer 34 to move the ultrasonic beam in a linear path along surface 32. Thus the probe 12 performs a two dimensional scan geometry of the human or animal tissue supported on surface 32.

In particular, a line scan is performed by oscillating the single element fixed focus transducer 34 back and forth using a DC brushless motor 38 or an equivalent limited angle torque motor. An optical encoder 44 is mounted to the base of the DC brushless motor 38 and attached to the shaft of the motor in order to provide feedback information to the control electronics in scan controller 14 as to the rotational position of the motor 38.

The transducer 34 is mounted to a probe arm 48 by suitable means such as adhesive, which arm 48 is attached to the shaft of the DC brushless motor 38 creating an arc to be swept out each time the motor moves through its predefined angle of rotation. The transducer is positioned directly under the platen 30 in which the finger to be imaged is placed. In order to minimize attenuation of the ultrasonic energy as it propagates to the finger, the entire transducer is positioned in a liquid-filled region, i.e. in a water filled cavity 50. This requires establishing a water tight seal in two places on the probe. The first seal is an oscillating seal generally designated 52 and is used to seal the oscillating motor shaft. The second seal is a large bellows 54 responsible for forming the overall water cavity 44. One end of bellows 54 is fastened in a liquid tight manner, such as by screws 56, to a motor bracket 58, and the other end of bellows 54 is fastened in a liquid-tight manner, such as by screws 62, to the portion of the probe housing 64 surrounding platen 30. The oscillatory seal 52 will be described in detail presently. The liquid-filled region 50 thus contains an ultrasonically conductive medium such as water, mineral oil or the like.

Once a single line has been scanned, the second motor means 40 in the form of a linear actuator motor is used to move the entire assembly along the second axis of motion, where a second line is scanned. This process is repeated until an equivalent scan area of 0.75"×0.75" has been imaged.

Upon completing the scan, linear actuator 40 is rewound to its starting position as indicated by a position sensor 68 which will be described in further detail presently.

Figure 2:
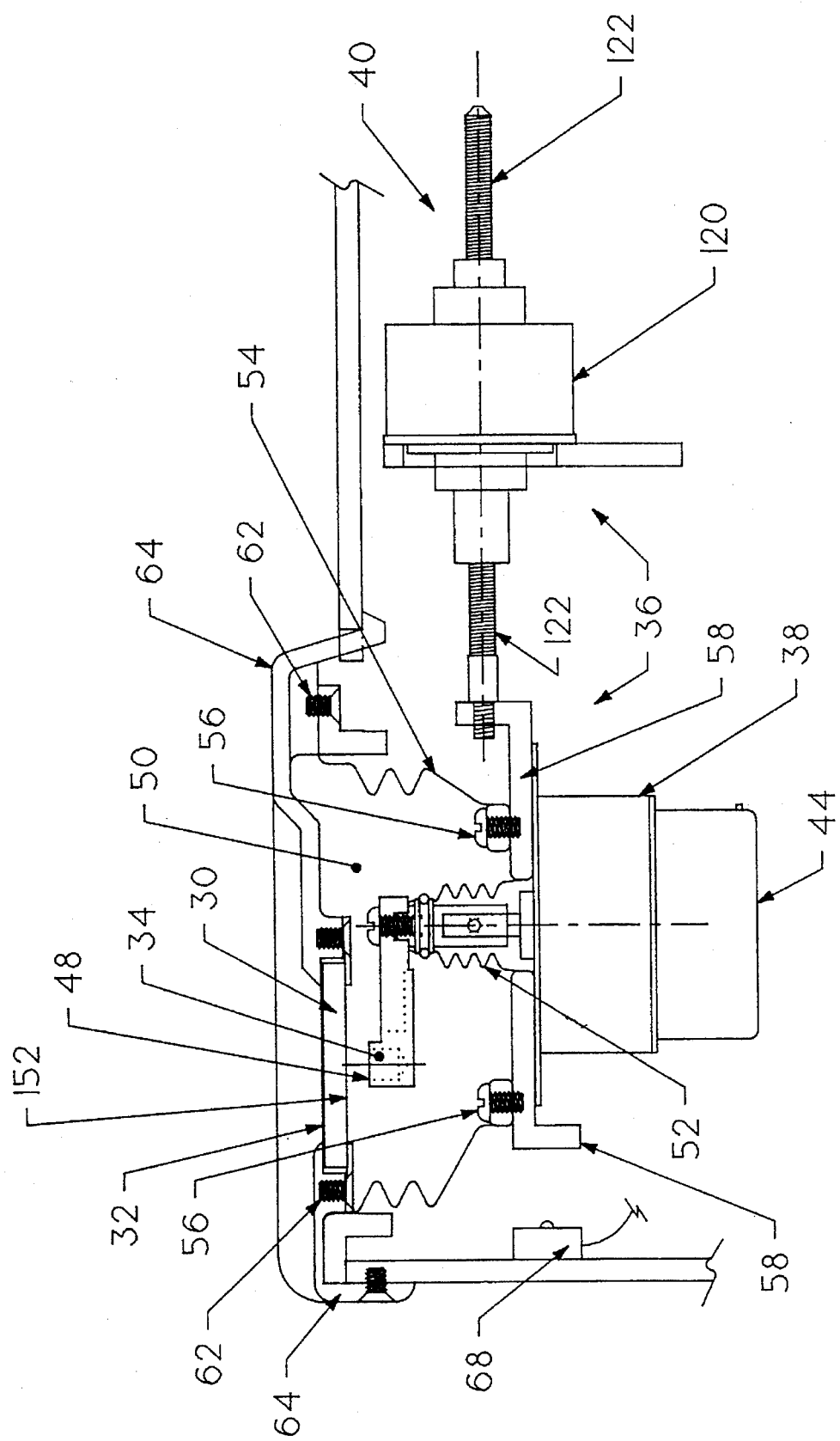
FIG. 2 is a fragmentary cross-sectional view, partly diagrammatic, of the probe means in the system of FIG. 1.
Figure 3:
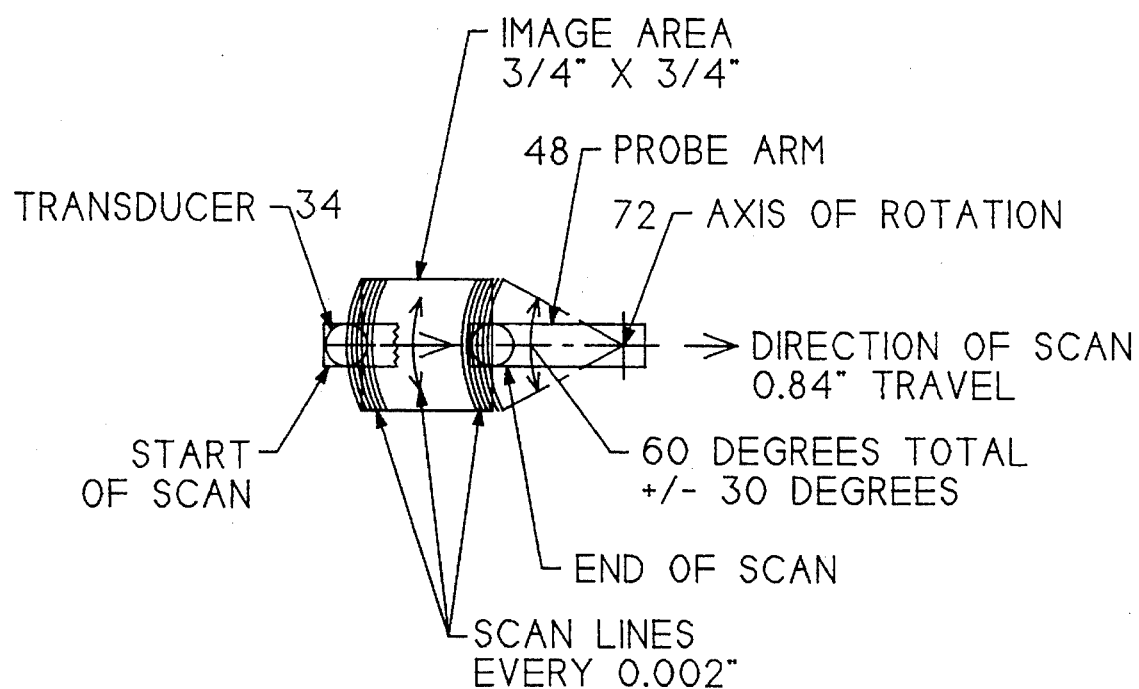
FIG. 3 is a diagrammatic view illustrating operation of the probe means of FIG. 2.

The desired scan geometry is a rectangular window measuring 0.75"×0.75" with data points taken every 0.002" along an X-Y axis configuration. The probe architecture of FIG. 2 shows how the Y axis of motion is easily accomplished by using the linear actuator 40. As will be described in further detail presently, the linear actuator 40 is a stepper motor with an integrated gear assembly that converts the discrete rotational steps of the motor to linear motion in steps sizes of 0.002". However, as is shown in FIG. 3, the X axis geometry is more difficult to achieve due to the non-linear motion of the transducer 34 as a result of being driven by the probe arm 48 pivoting about a single point or pivot axis 72. The resulting image shows an amount of distortion therein equivalent to the amount of curvature defined by the arc of the transducer path of movement. In the system of the present illustration the 60 degree arc is a result of the need to scan 0.75 inch in the X direction. As a result, the scanned image must go through a linearization algorithm to correct for the distortion. The algorithm can be implemented in software of system 10 and its function is to alter each pixel position in order to compensate for the arc motion of the transducer 34. Initially, the data is stored as scanned, each row of stored data points representing an arc of the image. Based on the dimensions of the scanned arc, the algorithm calculates the new position for each pixel in the image.

In particular, since the data for any single scan line is captured in an arc geometry, the final image of the finger would be distorted without first compensating for the arc motion. In order to compensate for this motion, the software of system 10 performs a "linearization" routine which effectively shifts the pixels from their current position in memory to the proper place in memory. By doing this prior to displaying the image, the image is no longer distorted. The algorithm for shifting the data is given below, in conjunction with the illustrations of FIGS. 4 and 5.

Figure 4:
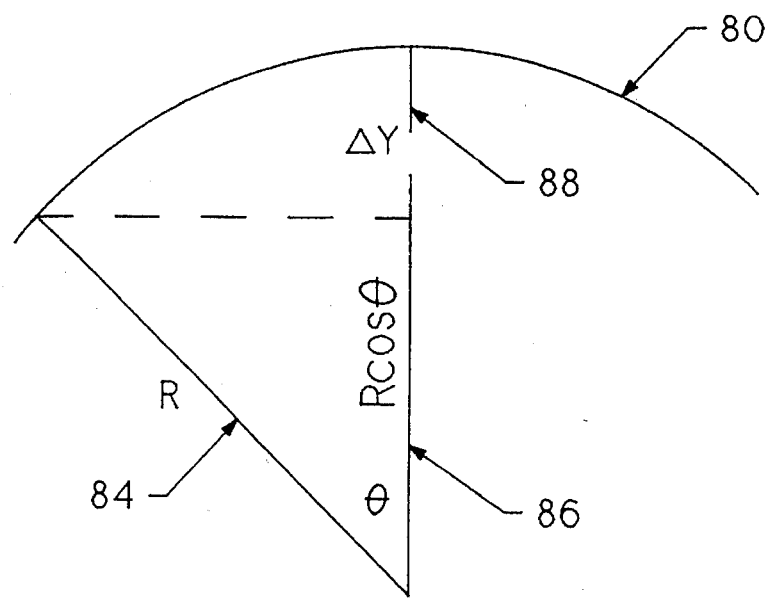
FIG. 4 is a graph illustrating an aspect of operation of the probe means of FIG. 2.
Figure 5:
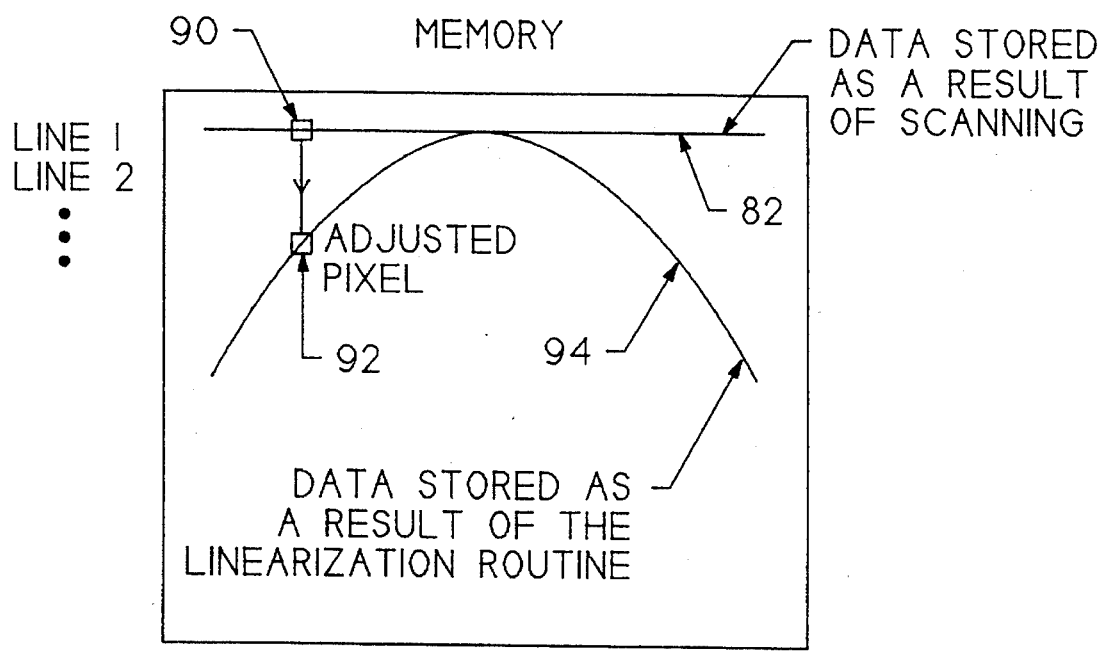
FIG. 5 is a graph illustrating an aspect of the operation of the probe means of FIG. 2.

The data along a given scan arc represented by curve 80 in FIG. 4 is stored in a single line of memory designated 82 in FIG. 5. Each pixel to the right or left of the center pixel must be shifted to a new memory location that is effectively below the center pixel. The question becomes one of how much to shift (i.e., how many memory locations). In order to determine this, it must be understood that each line of memory represents a displacement from the previous line by 0.002". In addition, each point on a line represents an angular displacement from the previous point by 0.176°. Knowing this, the following algorithm can be implemented.

1. Select the point in memory to be moved. Determine how may pixels from the center point this is.

2. Calculate the angular displacement $\emptyset$ using the following:

$\emptyset$=(# of pixels from center point)·(0.176°).

3. Calculate the displacement in inches from the top center point.

$\Delta Y = R - R\cos\emptyset$

4. Calculate the number of memory lines to be shifted by the following:

# of lines=$\Delta Y/0.002$

In connection with the foregoing algorithm, the radius R is represented by line 84 in FIG. 4 and the quantities $R\cos\emptyset$ and $\Delta Y$ are designated 86 and 88, respectively, in FIG. 4. The angular displacement $\emptyset$ also is illustrated in FIG. 4. A pixel stored as a result of scanning is shown at 90 in FIG. 5 and an adjusted pixel, i.e. shifted to a new memory location, is shown at 92 in FIG. 5. Curve 94 in FIG. 5 represents the data stored as a result of the linearization routine, i.e. a series of adjusted pixels.

After completion of this process, the stored image is no longer distorted and represents a true image of the finger. In order to have enough data to create a final image of 0.75"×0.75", additional data in the Y axis of motion must be gathered. Approximately 0.84" of scan arcs must be collect to create 0.7541 of linearized data. This is due to the fact that a single linearized scan line cannot be created unless all the points of that line have been scanned in due to several arcs. A careful study of FIG. 3 shows that the arcs on the extreme ends of the scan only contribute to the edges or the center of the image data. Thus, in order to capture enough data to be linearized, additional samples over the 0.75" window must be captured.

An important aspect to the overall scan geometry is how the timing for the actual data points is accomplished. One approach would be to have a free running timer exciting the transducer at regular intervals and collecting the returned echoes. The timer would have to be running at a rate proportional to the speed of the motor 38 which would collect a data point every 0.002". The disadvantage of this approach is that it requires a very constant RPM motor in order to achieve the proper sampling. This means that while the motor is ramping up to speed or ramping down during a direction change, data cannot be gathered. This results in a significant amount of lost time which increases the overall scan time.

The preferred approach and the one implemented in the system of the present invention is to connect the optical encoder 44 to the shaft of motor 38. The optical encoder 44 outputs a pulse for a given amount of angular rotation. This pulse is dependent only on the amount of angular rotation and not on the speed of rotation. Therefore, by selecting an optical encoder with the proper angular resolution and designing the probe arm 48 to the appropriate length, a pulse from the optical encoder can be generated which corresponds to a transducer movement of 0.002", completely independent of motor velocity. This allows very low cost, low precision motors to be used for the scanner. Furthermore, using this arrangement data can be collected during the ramp up and ramp down times of the motor 38, resulting in much faster scan times than the previous approach.

Figure 6:
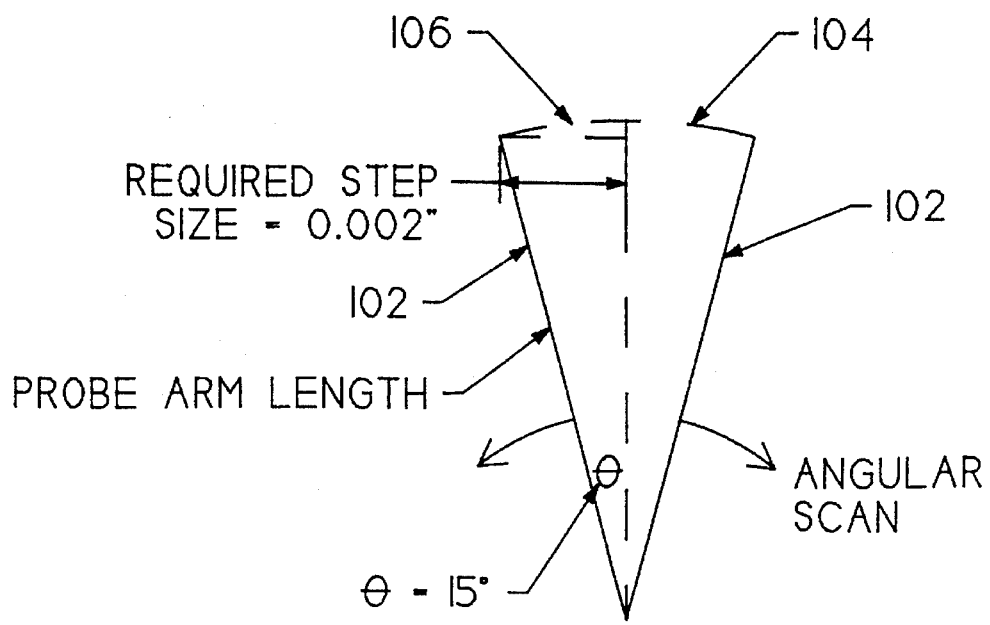
FIG. 6 is a schematic diagram illustrating one aspect of the relationship between encoder angular resolution and probe arm length.
Figure 7:
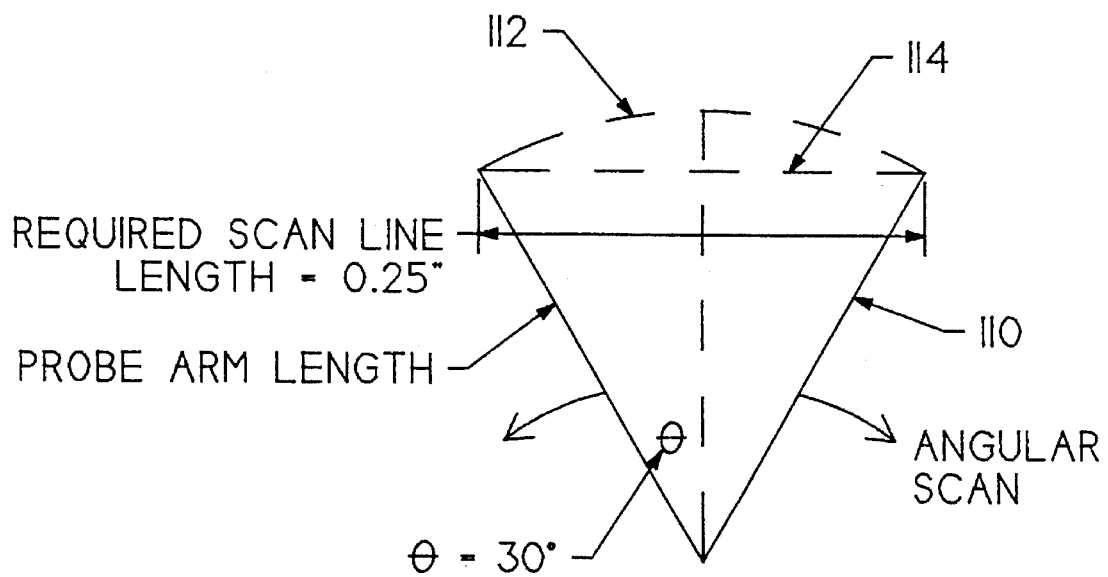
FIG. 7 is a schematic diagram illustrating another aspect of the relationship between encoder angular resolution and probe arm length.

The foregoing is illustrated by the following examples of probe arm length calculation in conjunction with FIGS. 6 and 7. The length of the probe arm 48 is tightly coupled to the resolution of the optical encoder 44 and to overall size of the desired scan area. For the system of the present illustration, the required step size for imaging a finger is approximately 0.002" and a scan area of 0.75"×0.75" is desirable. The optical encoder 44 has a resolution of 512 lines per revolution and provides in-phase and quadrature outputs. When interfaced to an optical decoder IC, for example Hewlett Packard model #HCTL 2020, a composite pulse is generated providing 2048 pulses per revolution. At 2048 pulses per revolution, an angular spacing of 0.175° is obtained.

In order to traverse a distance of 0.002" per angular increment of the optical encoder, a probe arm 48 of the appropriate length must be selected. The probe arm length is calculated as follows, and in reference to FIG. 6 wherein the probe arm length PAL is represented by line 102, an angular scan is indicated by the broken arcuate line 104, and the required step size is indicated by the broken straight line 106. The angle Ø in FIG. 6 represents the angular spacing. With a required step size of 0.002" and angular spacing of 0.175°, the probe arm length PAL is calculated to be approximately 0.65" as follows:

$$\sin\emptyset = \frac{0.002"}{PAL} \quad \sin 0.175 = \frac{0.002}{PAL}$$

$$PAL = 0.65"$$

In connection with the foregoing, the requirement of scan area size must also be considered. It is desirable to have a scan size of 0.75"×0.75". In the system of the present example, the hall effect sensors in the brushless motor 38 are used to provide feedback information as to the position of the motor. Typically, three hall effect sensors are spaced 120° apart and provide angular positional information with a 30° resolution. In other words, it is very easy to scan sectors in sizes that are multiples of 30° (i.e., 30°, 60°, 90°, etc.). Choosing 60° as the sector size and knowing that a scan line length of 0.75" is required, the length of the probe arm is calculated as follows, and in reference to FIG. 7 wherein the probe arm length PAL is represented by line 110, an angular scan is indicated by the broken arcuate line 112 and the required scan line length is indicated by the broken straight line 114. The angle Ø in FIG. 7 represents the angular spacing. The probe arm length PAL is calculated to be approximately 0.75" as follows:

$$\sin\emptyset = \frac{0.75"/2}{PAL} \quad \sin 30 = \frac{.375"}{PAL}$$

$$PAL = 0.75"$$

This result is only slightly different than the required probe arm length calculated in accordance with FIG. 6. In fact, recalculating the step size resolution according to FIG. 6 using 0.75" as the probe arm length, a step size of 0.0023" is obtained which is well within the acceptable margins of error for fingerprint imaging. It should be noted, however, that with a small modification to the circuitry of optical encoder 44, the output of the optical encoder can be used to provide motor positional information in place of the hall effect sensors. This eliminates the requirement of a sector size in 30° increments since the optical encoder has significantly higher resolution. Thus, the probe arm length can be reduced to its theoretical optimum (0.65") and a sector size can be selected to provide a 0.75" scan line length (approximately 70.5°).

As previously described, two motors are used to achieve the scan geometry of the probe architecture. The first motor 38 is responsible for oscillating the piezoelectric transducer 34 in an arc like fashion in order to capture a single line scan worth of data along the X axis. The second motor 40 is a linear actuator that is used to step the first motor assembly to the next line on the Y axis in order to capture a second scan line. This process is repeated until the entire area of interest has been scanned.

Brushless DC motors are gaining in popularity over conventional DC motors due to their numerous performance advantages. The main difference between the two concepts is the means of cumutating the motor coils. In order for any DC motor to operate, the current to the motor coils must be continually switched relative to the field magnets. In a brush type unit this is accomplished with carbon brushes contacting a slotted commutator cylinder which has each motor coil connected to a corresponding bar of the commutator. The switching continues as the motor rotates. With the arrangement there are physical limitations to speed and life because of brush wear. In a brushless motor, the position of the rotor is sensed and continuously fed back to commutation electronics to provide for appropriate switching. The rotor position sensing can be accomplished in many ways, but most manufacturers use hall effect devices. These devices usually provide optimum performance and size versus cost. The sensors are spaced 120° apart and fire in pairs to provide position information. There are 720° electrical degrees for each mechanical revolution. This provides a position feedback resolution of 30°.

A three phase DC brushless motor 38 is used to oscillate the transducer for generating a single line arc scan. Internal to the motor are three hall effect switches which provide feedback information to the scan controller circuit 14. This information provides fairly coarse feedback regarding the angular position of the motor 38. Depending on the state of the hall effect switches, the scan controller circuit sources or sinks current through any or all of the three windings on the motor. This allows for control over both the speed and direction of the motor 38. Thus, by properly monitoring the state of the hall effect devices, the motor 38 can be caused to oscillate back and forth in a sector size that is a multiple integral of the minimum resolution defined by the hall effect switches. The system of the present illustration sweeps out a sector of approximately sixty degrees which is required to achieve a scan line length of 0.75".

Once the motor 38 has swept the transducer 34 across a single line, a linear actuator motor 120 is operated to step the entire assembly along the second axis of scanning. The linear actuator 40 is a small DC stepper motor 120 with an integral lead screw 122 attached so as to convert rotational motion into linear motion. Once the scan controller 14 has sensed that the transducer has completed a line scan, the linear actuator 40 is commanded to move along the second axis of motion by a single line. The motion of transducer 34 is then reversed to sweep the transducer back across the finger in the opposite direction. This process is repeated until the desired area has been scanned. The linear actuator 40 is then rewound to its starting position in preparation for a new scan. The sensor 68 provides positional feedback to indicate that the linear actuator 40 has rewound to the starting position. The sensor 68 provides a signal to the scan controller 14 to halt the rewind process. Several sensors are suitable for this application, including microswitches, hall-effect devices, optical sensors, etc. By way of example, in an illustrative system, motor 38 is a Globe Motors model #559A104, optical encoder 44 is Hewlett Packard model #HEDS-5640 and linear actuator 40 is Hayden Switch Instruments model #35862.

Figure 8:
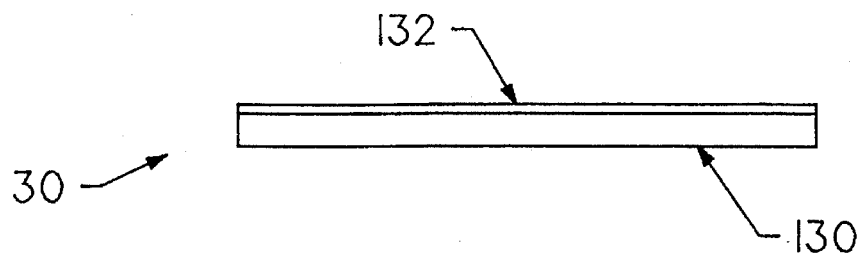
FIG. 8 is a side elevational view of the platen in the probe means of FIG. 2.
Figure 9:
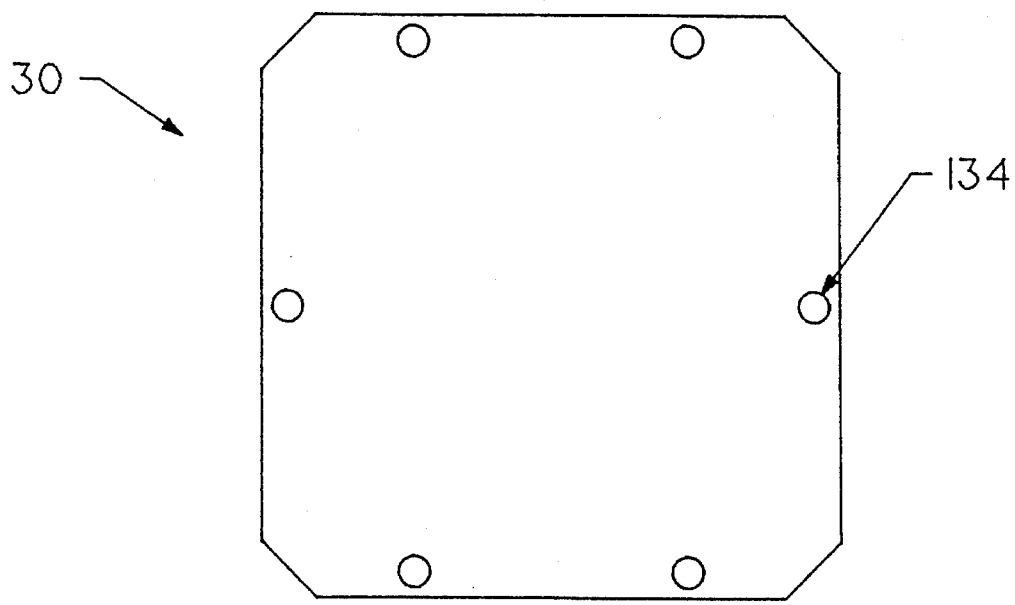
FIG. 9 is a top view of the platen of FIG. 8.

The supporting means or platen 30 is shown in further detail in FIGS. 8 and 9. As previously described, platen 30 creates the interface between the finger and the water path of the ultrasonic transducer 34. It must be of sufficient mechanical strength to provide a rigid support for the finger during the scan process. Deflection or deformation of the platen 30 could result in a distorted image and make the post processing software more difficult. Ideally, the acoustic impedance of the platen 30 must match the skin of the finger as close as possible. Furthermore, since it is highly desirable to place a finger onto the platen 30 without the use of any types of acoustic couplant, the platen interface must be able to fully contact the surface of the finger, minimizing any air gaps in-between. All of these requirements coupled with the ability of the platen 30 to pass high frequency ultrasound without appreciable attenuation or frequency down shift must be met in order to obtain high quality images of the finger.

Platen 30 is constructed using a cross-linked polystyrene or perspex material 130 coated with a thin layer 132 of silicone RTV. The body of polystyrene or perspex material 130 has an acoustic impedance very near that of human tissue and a thickness suitable to provide the necessary mechanical rigidity and provide as short an ultrasonic path as possible, for example a thickness in the range of 1/16 inch to 1/8 inch. Ultrasonic frequencies of 30 MHz are able to propagate through the material without appreciable modification. In order to provide maximum coupling to the finger, if desired the platen 30 can be coated with the thin layer 132 of silicone RTV. Other types of silicone latex rubber can be employed. The RTV improves the mechanical coupling to the finger while maintaining the proper acoustic impedance. The RTV must be of sufficient thickness so as to be able to range gate out the polystyrene/RTV return echoes and process only those echoes associated with the RTV/finger interface. The required thickness of RTV is dependent upon the overall 'Q' of the transducer 34. By way of example, in an illustrative system, the body 130 has a thickness of about 1/16 inch to 1/8 inch and coating 132 has a nominal thickness of about 0.010–0.030 inch. A series of mounting holes 134 can be provided around the periphery of platen 30.

Figure 10:
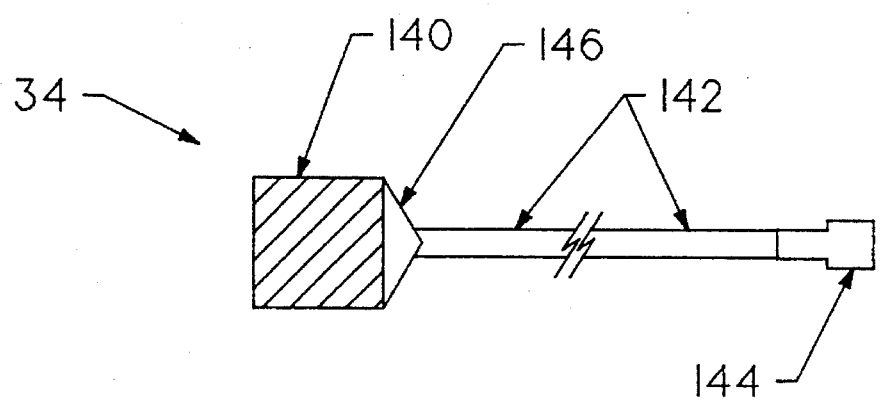
FIG. 10 is a diagrammatic view of the transducer of the probe means of FIG. 2.

An illustrative form of transducer 34 is shown in FIG. 10. The body 140 of transducer is contained in a stainless steel housing. A cable 142 terminated in a connector 144, of the type referred to commercially as Microdot, is electrically connected to the piezoelectric transducer element within housing 140, the connection being enhanced and sealed by a body 146 of potting compound or the like which also provides strain relief. Two forms of transducer 34 can be employed depending upon the type of scanning. A high frequency transducer of approximately 30 MHz, with an aperture of approximately 0.180" and a focal length of approximately 0.25" can be used for fingerprint imaging. This transducer provided the highest resolution, i.e., smallest spot size, but was not significantly attenuated due to the limited depth of penetration into the finger. A second transducer of similar physical characteristics but reduced in frequency to approximately 15 MHz can be used for the subdermal scanning that was targeted at artifacts other than the fingerprint structure. For this imaging, the 30 MHz ultrasound would be so significantly attenuated that the cost of the signal processor 16 would be prohibitive. Therefore, by dropping in frequency by a factor of 2, a much stronger signal is received.

A principal requirement on transducer 34 is to minimize the overall spot size which it generates. The spot size is a function of the frequency of the transducer, aperature and overall focal length and is given by:

$$d = 2.44(f_L/D)\lambda$$

where d is the spot size measured at the zero crossing points, $f_L$ is the transducer focal length, D is the transducer aperture and $\lambda$ is the wavelength of the soundwave. In the design of a transducer, it is desired to keep the ratio $f_L/D$ as small as possible. This can be accomplished using a variety of well-known techniques such as an external focusing lens, a curved transducer element or a combination of both. By way of example, in an illustrative system, transducer 34 produces a spot size of 0.002 inch measured at −6 db points per ASTME1065 and has a ring time of 1 cycle measured at −20 db down from peak. Cable 142 is Cooner coaxial or the equivalent having a diameter of about 0.037 inch. An illustrative commercial form of transducer 34 is available from Krautkramer Bransen under model no. 389-005-860.

Figure 11:
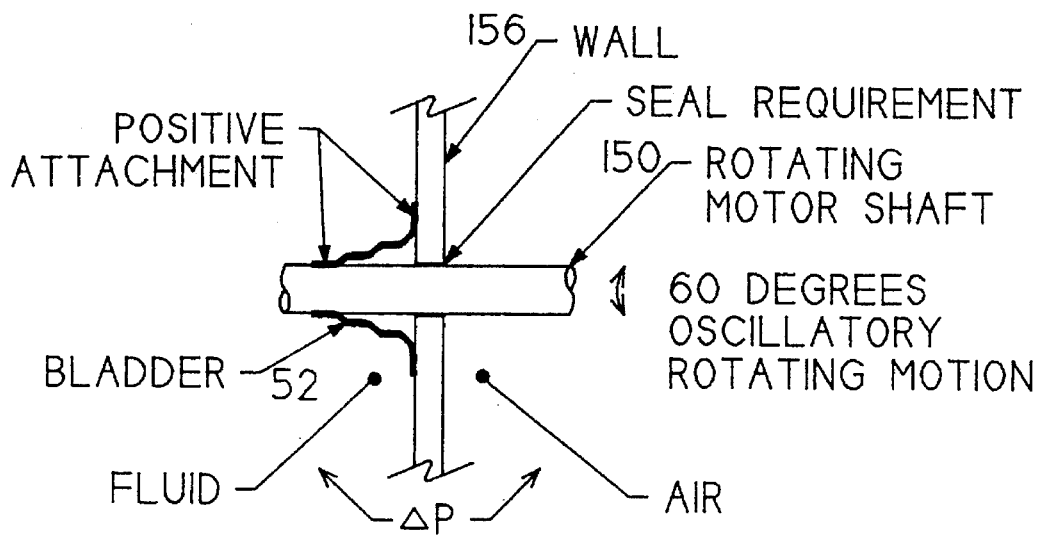
FIGS. 11–13 are diagrammatic views illustrating the oscillatory seal for the motor shaft in the probe means of FIG. 2.
Figure 12:
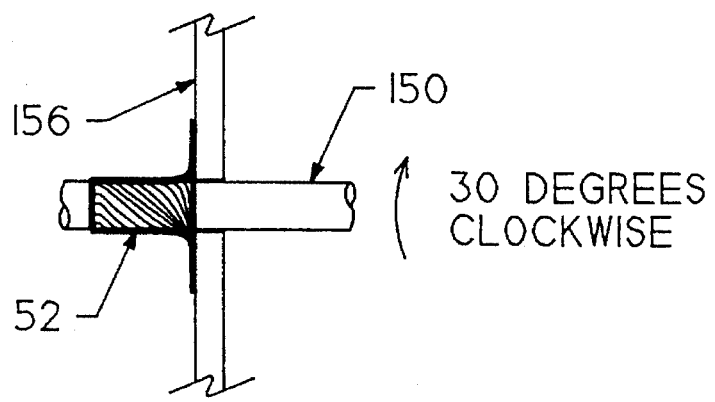
Figure 13:
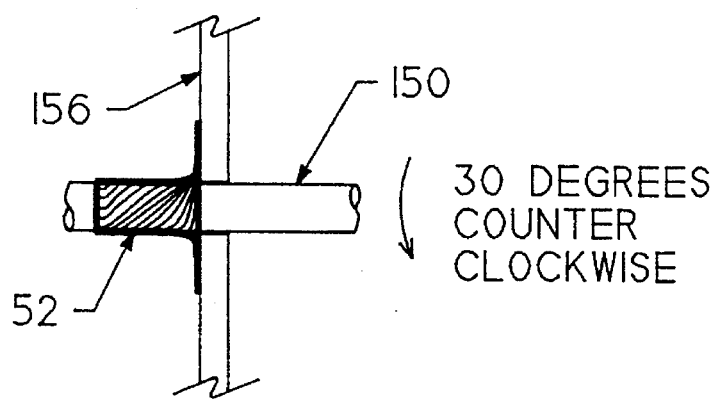

FIGS. 11–13 illustrate in further detail the oscillatory seal 52 which is employed to seal the oscillating shaft 150 of motor 38. In order for ultrasound to propagate any appreciable distance at the frequencies in use for the type of scanning described herein, the sound must propagate through water as opposed to air. As a result, the entire sound path from the transducer 34 to the first or inner 152 surface of platen 30 must be entirely a water path. Since the motors 38 and 120 responsible for creating the scan motion cannot operate submersed in water for any significant amount of time, a water tight seal is required. The seal is responsible for creating a water tight environment for a rotary oscillating rod with limited angular motion. The angular motion is approximately 60 degrees of rotation. Any leakage of the water over a period of 10 years would be deemed as unacceptable for the scanning applications described herein. Furthermore, no differential pressure was present across the seal which prevented the use of some common techniques known to the sealing industry. Lastly, since the seal would be directly loading the 3 phase DC brushless motor 38 which has limited torque capability, the seal should present a minimum load with respect to torque as seen by the motor 38.

The method according to the present invention for providing an absolute seal with long life is to employ a flexible bladder 52 with positive attachment to the rod or motor shaft 150 and wall or similar structural member 156 through which motor shaft 150 extends. Attachment methods include clamping and/or adhesive means. The bladder 52 is of a flexible material that is able to stretch and will not allow fluid to pass through it such as latex or other rubber or rubber like material. The bladder 52 is attached in such a manner as to allow it to be loose between the two attachment points. This looseness and the stretch of the material allows for the limited rotary oscillatory motion with little drag exhibited on the motor 38.

Use of this type of bladder seal is limited to only rotary motion and the total angle of oscillatory motion is constrained by various factors such as looseness, allowable stretch, attachment points, and available motor torque. The material chosen for this application was a latex based product with a wall thickness of approximately 0.020" thick, and sealed to rod 150 and wall 156 by a water-resistant epoxy which is inert to latex material.

Figure 14:
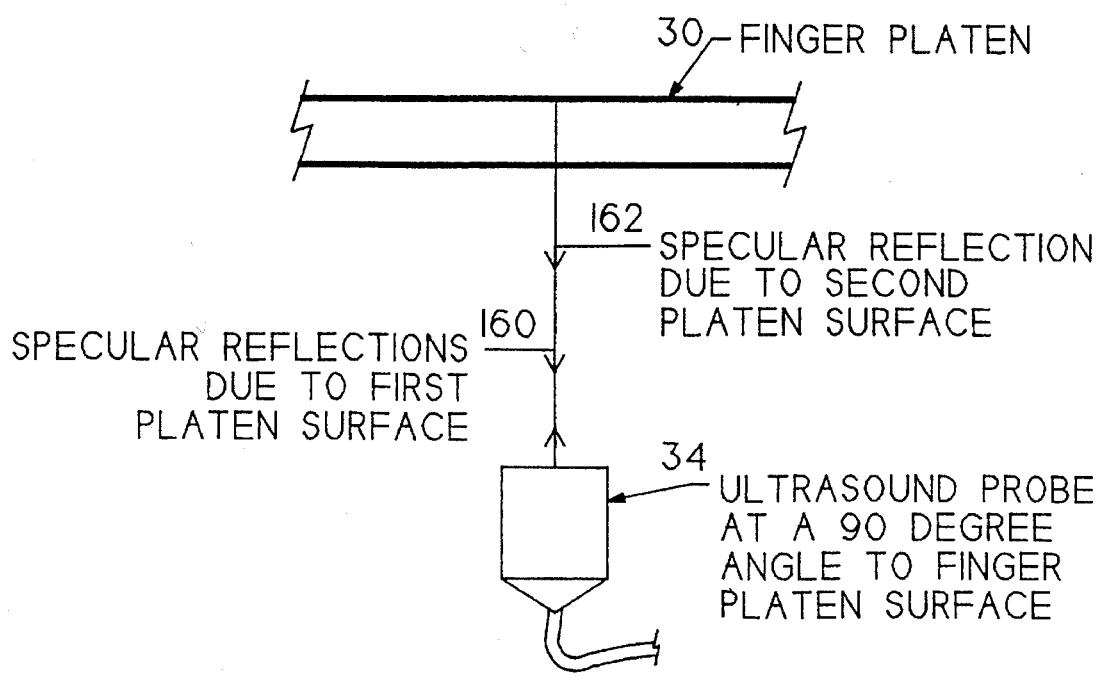
FIGS. 14 and 15 are diagrammatic views illustrating two different modes of scanning with the system of the present invention.

Turning now to the various modes of scanning, acquiring images from the surface of the finger or near the surface of the finger such as in the case of subdermal fingerprint imaging, the amount of attenuation of the ultrasonic signal is minimum. Therefore, in order to obtain maximum spatial resolution, the frequency of the transducer 34 is very high. For this application, the frequency of the transducer is approximately 30 MHz. In order to capture images from structures just below the surface of the finger, an electronic range gate as shown in FIG. 14 is used to allow only those echoes returned from the depth of interest to be processed. Therefore, the only modification to the system to process surface fingerprint images versus subdermal fingerprint images is in the application of the range gate. The timing of this range gate can be controlled by software making it a transparent change to the person that is being imaged.

In both cases the ultrasonic energy enters the finger at a 90 degree angle to the surface of the finger as shown in FIG. 14. Orienting the transducer 34 in this fashion gives the maximum signal strength possible. However, the specular reflections 160 and 162 from the front and back sides, respectively, of the platen 30 are also returned to the transducer 34. This is not a problem for surface imaging since they can be range gated out. However, for deep subdermal imaging, the multipath specular reflections can represent a severe problem when trying to image at particular depths. Therefore, the transducer 34 must be oriented in such a way as to eliminate these echoes.

When images from deeper in the finger are of interest, the amount of attenuation of high frequency ultrasonic signals is so significant that either the signal is lost altogether or the gain bandwidth product of the amplification stages found in the signal processor 16 become so large that the cost of the system is prohibitive. Therefore for imaging these structures, a lower frequency transducer 34 is used, for example about 15 MHz. This solves the problem of high attenuation at the cost of slightly reduced spatial resolution. However, the loss of resolution is not critical since the subdermal structures of interest are larger than the ridge structures found on the surface of the finger.

Figure 15:
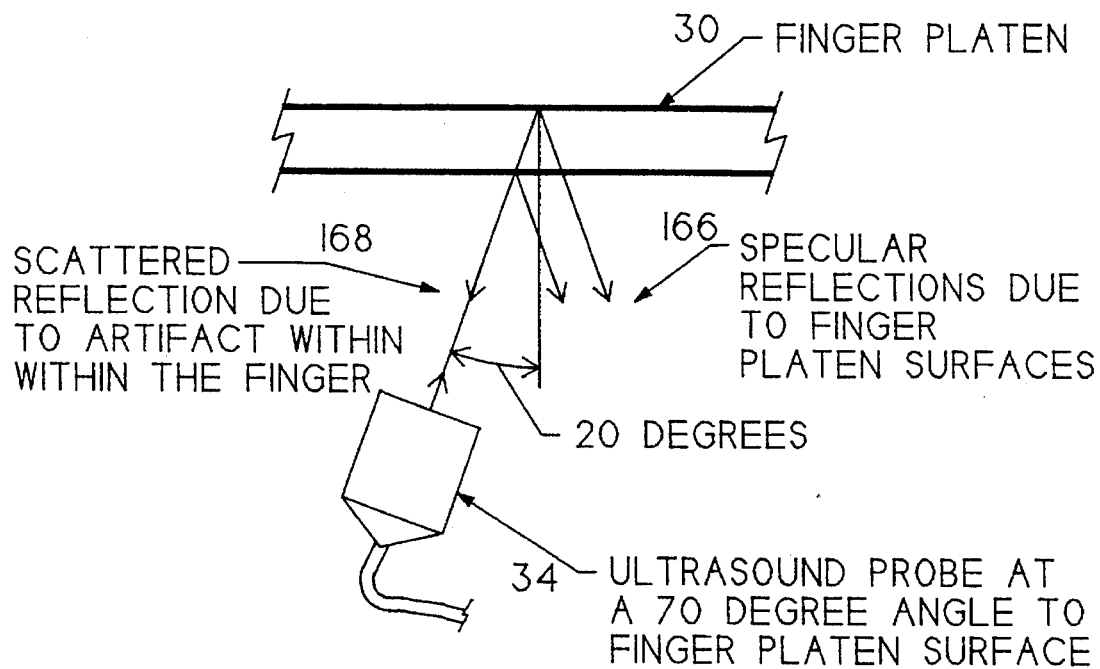

A secondary problem that can occur when imaging deep inside the finger is that depending on the depth at which the echo is to be collected, a multipath echo from specular reflectors that fall in the path of the sound wave may shadow the artifact of interest. Therefore, the multipath echoes that are caused by the specular reflectors need to be removed so as to enable imaging of the actual signals of interest. This can be accomplished by rotating the transducer 34 off axis by a small number of degrees sufficient to cause the specular return echoes to be missed as shown in FIG. 15. This causes any echoes 166 due to a smooth surface to reflect at an angle such that the return echo never makes it back to the transducer 34. Only those echoes 168 that scatter the sound wave in all directions can be seen by the transducer 34. Most structures of interest internal to the body will tend to scatter the soundwave, thereby making this technique very effective for this scanning application.

Figure 16:
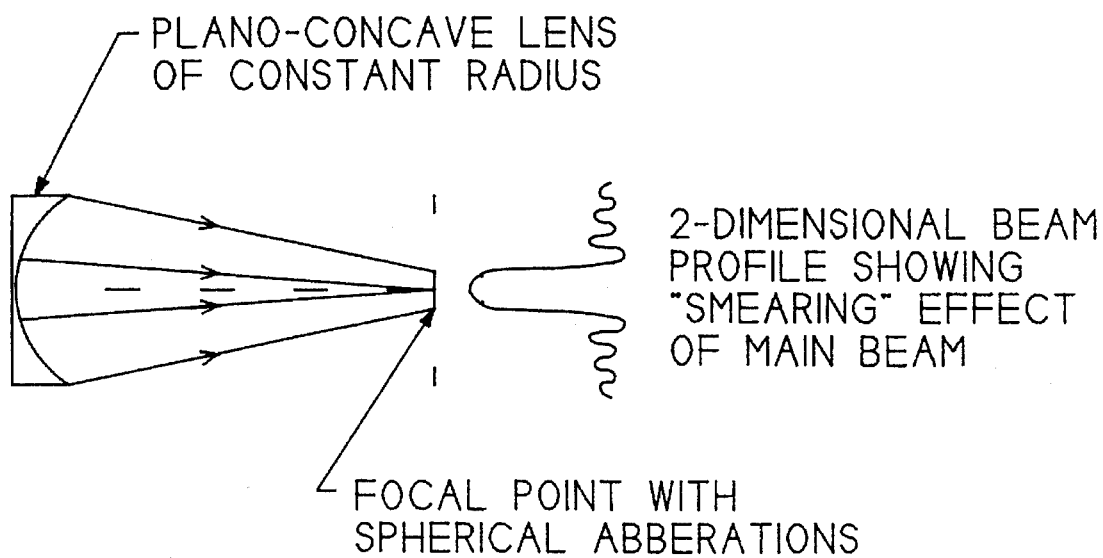
FIGS. 16 and 17 are diagrammatic views illustrating reduction of transducer spot size by correcting the lens focus.
Figure 17:
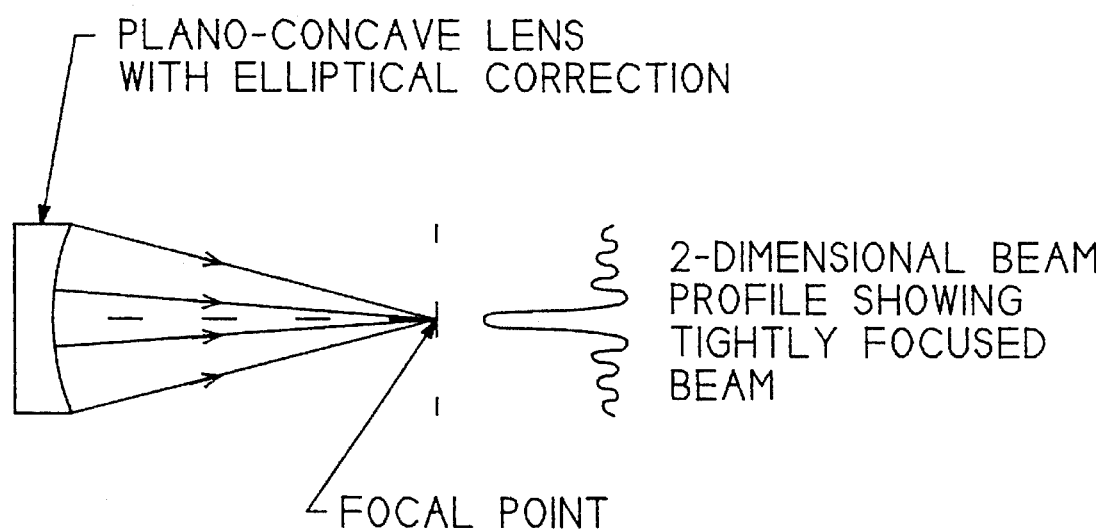

The industry standard for fabricating lenses for focusing ultrasound is to use a fixed radius to create the curvature of the lens. The lens material is normally made from polystyrene and is machined down to the desired size and curvature. This geometry is responsible for defining the focal length of the transducer and the spot size. However, analysis of the lens equation readily shows that constant radius lenses do not provide a diffraction limited spot size. They cause spherical aberrations which have the effect of blurring or enlarging the size of the focused beam. This is illustrated in FIG. 16. Therefore, in order to reduce the size of the spot to the theoretical minimum, a non-spherical shaped lens, a curved transducer element or a combination of a curved element and non-spherical lens must be employed. A corrected lens focus to reduce the spot size is illustrated in FIG. 17.

As previously described, the system control and electronics comprises four main subassemblies: signal processor 16, power supply 20, scan controller 14 and data buffer 18. Signal processor 16 is responsible for driving and receiving signals to and from the ultrasonic transducer 34. Analog to digital conversion takes place on this subassembly and the digital data is passed to the data buffer card 18. The data buffer card 18 is a high speed digital RAM capable of storing an entire fingerprint of greyscale data. This card acts as a FIFO between the signal processor 16 and any post processing hardware used to process the fingerprint data. The scan controller subassembly 14 is responsible for controlling the motion of the transducer 34. It is this subassembly that controls both the X motion and Y motion over the entire scan area. The three subassemblies are powered by a power supply 20 capable of generating all of the necessary voltages at the proper current ratings. The power supply 20 has a logic input to turn off any supply voltages that are not in use in order to conserve energy. The determination whether to turn power off is made by the scan controller 14.

Figure 18:
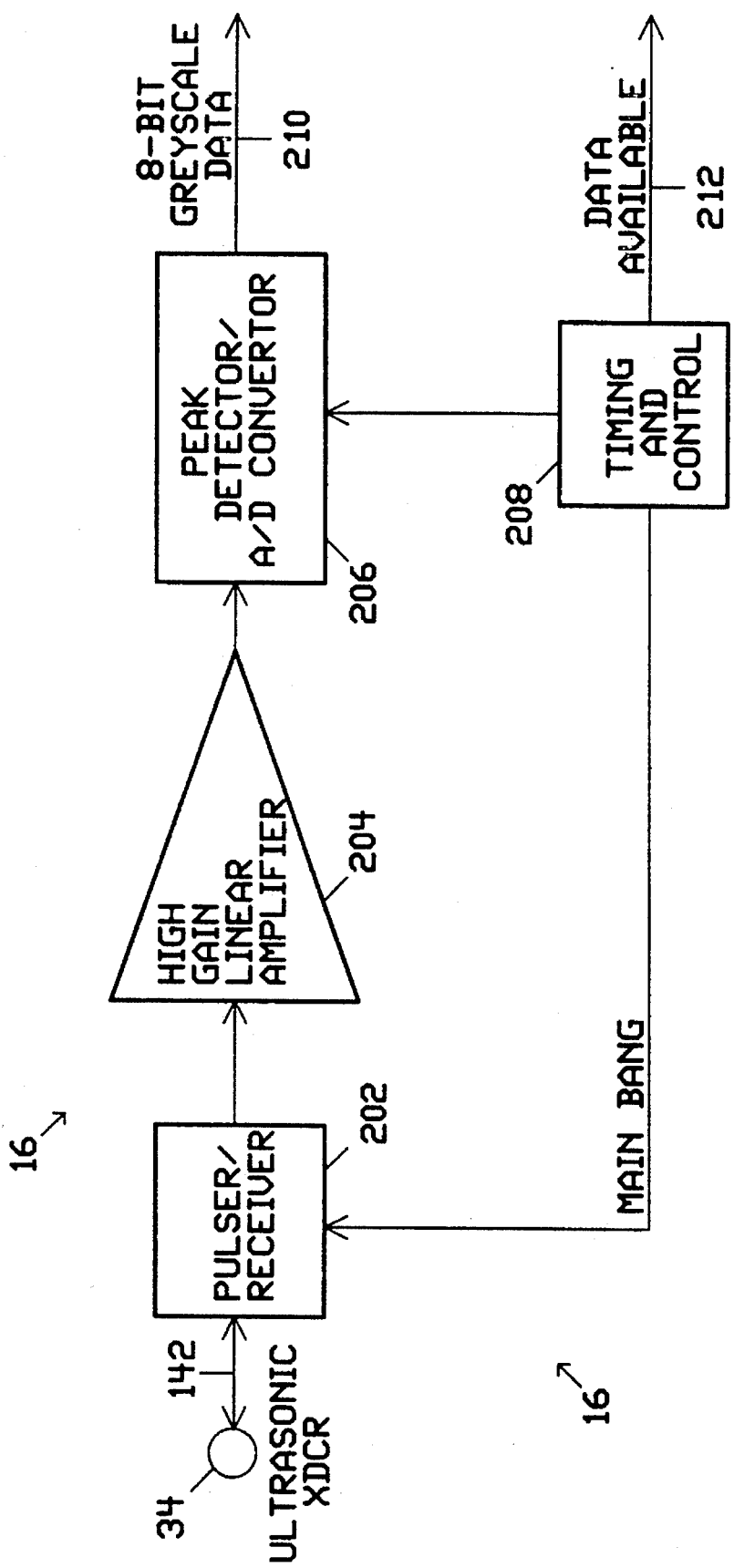
FIG. 18 is a block diagram illustrating the signal processor of the system of FIG. 1.
Figure 19:
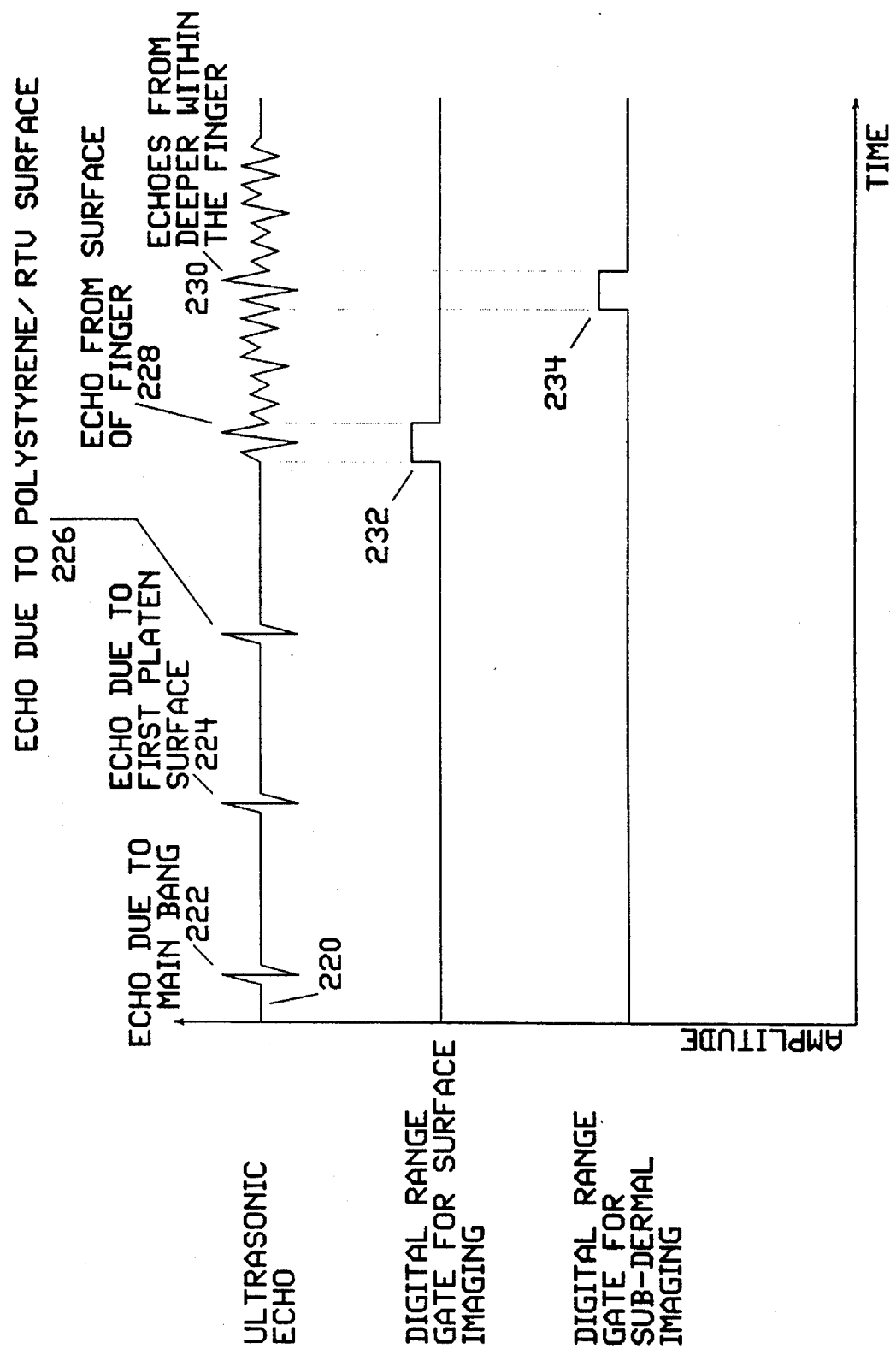
FIG. 19 is a graph including waveforms illustrating operation of the signal processor of FIG. 18.

FIG. 18 is a functional block diagram of the signal processor 16 which is the interface link between the ultrasonic transducer 34 and the data buffer 18. The signal processor 16 contains all of the necessary hardware to drive and receive signals to and from the transducer 34. A pulser-receiver component 202 of signal processor 16 is connected to transducer 34 via the cable 142 and connector 144 previously described. The output of pulser-receiver 202 is connected to the input of a high gain linear amplifier 204, the output of which is connected to the input of a peak detector/ A-D converter component 206. A timing and control component 208 is connected in controlling relation to pulser/ receiver 202 and to peak detector/A-D converter 206. A single edge, negative falling pulse is provided by pulser/ receiver 202 to initially excite the crystal of transducer 34 into oscillation. The pulse has a fast fall time of approximately 3 nanoseconds and an amplitude of about 150 volts DC. The echoes caused by the finger are returned to the transducer 34 and received by the pulser/receiver 202 of signal processor 16 whereupon they are linearly amplified by amplifier 204. A range gate is applied to the signal which allows only that portion of the signal to propagate through to peak detection circuitry 206. Negative peak detection is performed on the signal and the maximum peak detected within a particular range gate is converted to 8 bit digital data provided at the output of component 206. The 8 bit digital data is sent via line 210 to the data buffer 18 along with a timing pulse (DAV) on line 212 for storage in the RAM memory of buffer 18. The timing and control portion 208 of the signal processor 16 is also responsible for generating the range gate timing pulse. The range gate is used to select what portion of the return echo is to be processed by the signal processor. Delaying the range gate to process a later portion of the ultrasonic return signal corresponds to imaging deeper within the finger. A timing diagram depicting the use of the range gate for selective imaging is given in FIG. 19. In particular, waveform 220 represents the various ultrasonic echo signals including the echo 222 in response to the main bang ultrasonic signal emitted from transducer 34, the echo 224 from the surface of platen 30 facing transducer 34, the echo 226 from the interface between platen body 130 and coating 132, the echo 228 from the surface of the finger being scanned and an echo 230 from deeper within the finger. Pulses 232 and 234 are the digital range gate pulses for surface and sub-dermal imaging, respectively.

Figure 20:
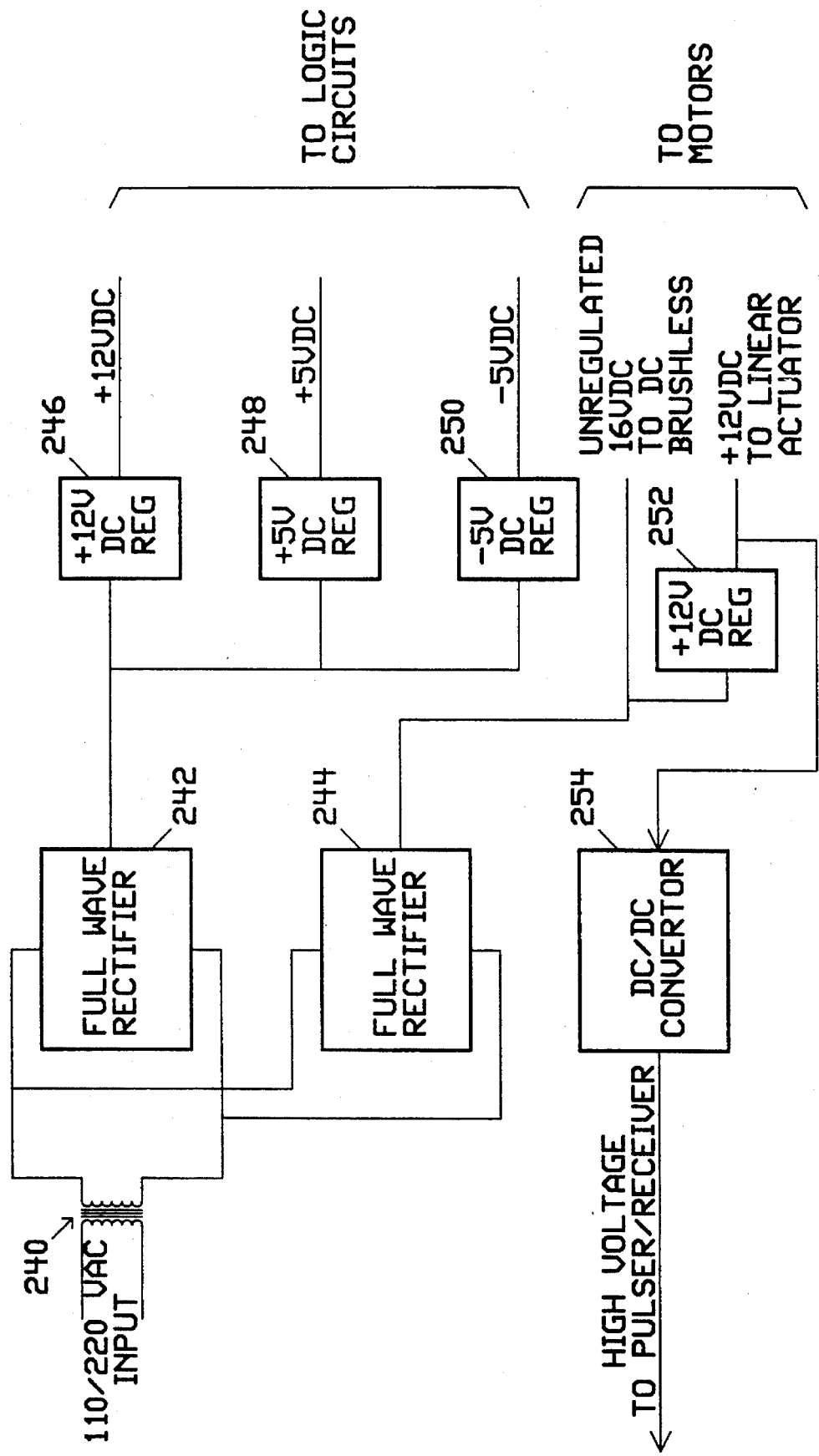
FIG. 20 is a schematic diagram of one form of the power supply of the system of FIG. 1.

A power supply capable of providing power for the linear and digital circuits of the scanner, for the ultrasonic transducer driver, and for the X and Y scan motion drive motors is shown in FIG. 20. The supply operates from either 110 VAC or 220 VAC line inputs and provides isolation from the line in order to comply with several safety certification requirements as defined by Underwriters Laboratories Inc. and other similar agencies. Line voltage selection can be made with switches or wire jumpers. A power transformer 240 with dual primary windings and a single secondary winding with a VA rating of 56 was selected. The secondary winding drives two rectifier networks 242 and 244. One rectifier 242 is a center-tapped bridge that charges two filter capacitors to generate unregulated supply voltages of +17 and −17 volts DC. Three linear regulators 246, 248 and 250 reduce these voltages to +5, +12, and −5 volts DC for the logic and amplifier requirements. The other rectifier 244 is a full wave bridge that charges a filter capacitor to provide an unregulated +17 volts with high current capacity. This line supplies a +12 volt linear regulator 252. The high voltage for the transducer driver is again supplied by a PWM fly-back converter 254 operating off the regulated linear drive motor supply line. The converter can supply up to 6 milliamps of current at an output voltage of 300 volts. This capacity can be increased by using a larger transformer core.

The converter can be disabled by pulling its ENBL input to ground potential. This is useful when power must be conserved or when switching noise produced by the converter interferes with low-level signal amplification. This provides maximum image fidelity by lowering the overall baseline noise of the system. Through the use of a simple feedback resistor, the output of the fly-back converter 254 can be varied allowing additional flexibility in the overall system configuration.

Figure 21:
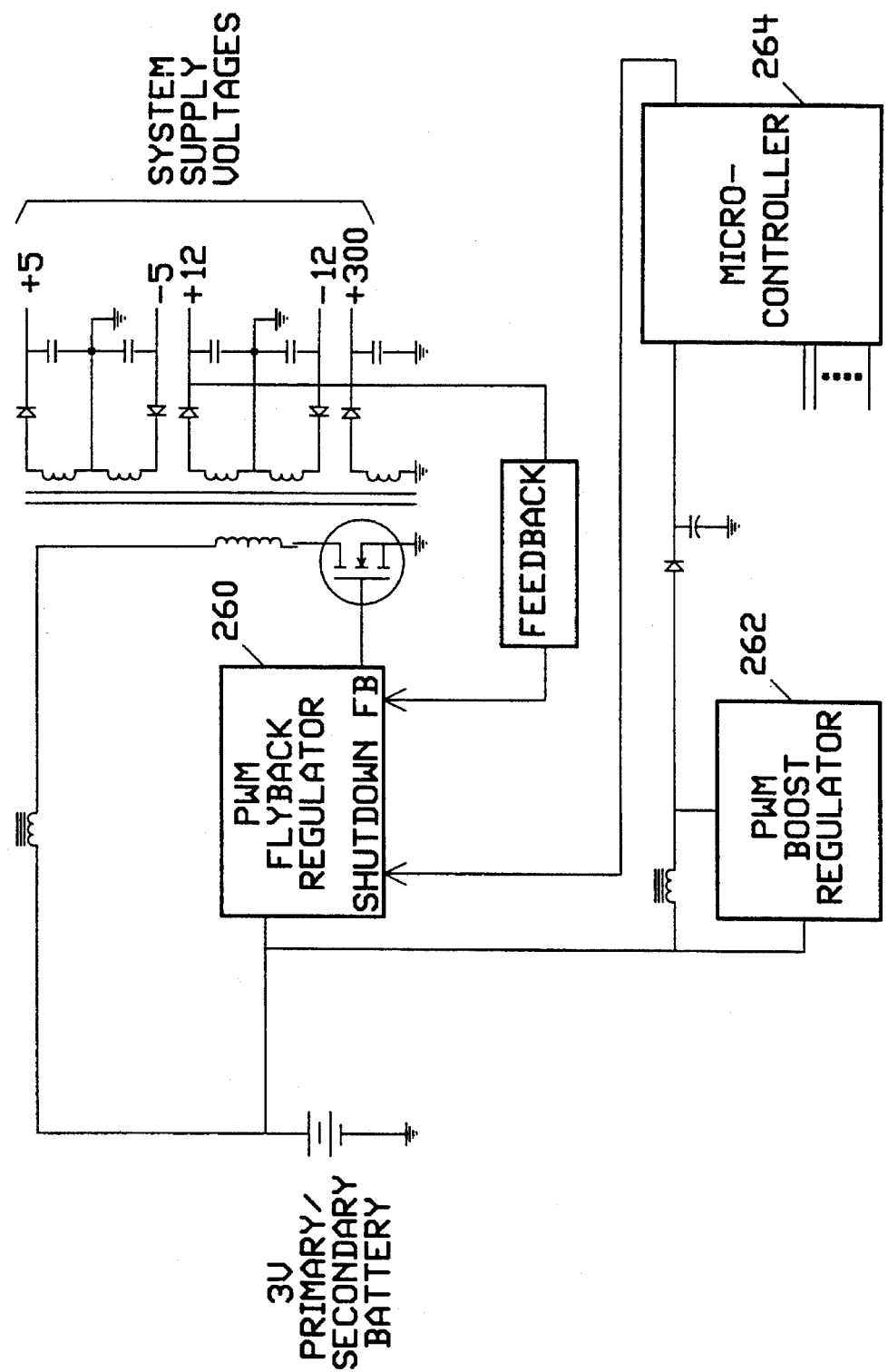
FIG. 21 is a schematic diagram of another form of the power supply of the system of FIG. 1.

There are certain applications that require remote operation of the identification system according to the present invention. These applications usually have only DC voltage available for powering the system and the amount of current that can be used to power an identification system is limited. The first step in providing a field usable device is to eliminate the high current drawing motors from the system. The second step is to add a DC to DC converter to the power supply design in place of the AC power transformer. The DC to DC converter is responsible for converting the DC voltage available to the unit to the proper DC voltage needed for the operation of the power supply. A functional block diagram of the necessary power supply operation is given in FIG. 21. The main PWM flyback converter 260 uses several secondary windings to generate the analog and logic supply voltages and the high voltage for driving the piezoceramic transducer. This converter can be completely shut down when the equipment is not in use. In the dormant state, the converter consumes only a few microwatts of power. A small PWM boost regulator 262 generates the supply voltage for a microcontroller 264. This regulator is always on when the equipment is powered up. A supervisory software loop running in the micro controller 264 during equipment dormant periods senses impending equipment usage and powers up the main converter 260 for the duration of active use. After equipment usage terminates, the main converter 260 is shut down again to extend battery life.

Figure 22:
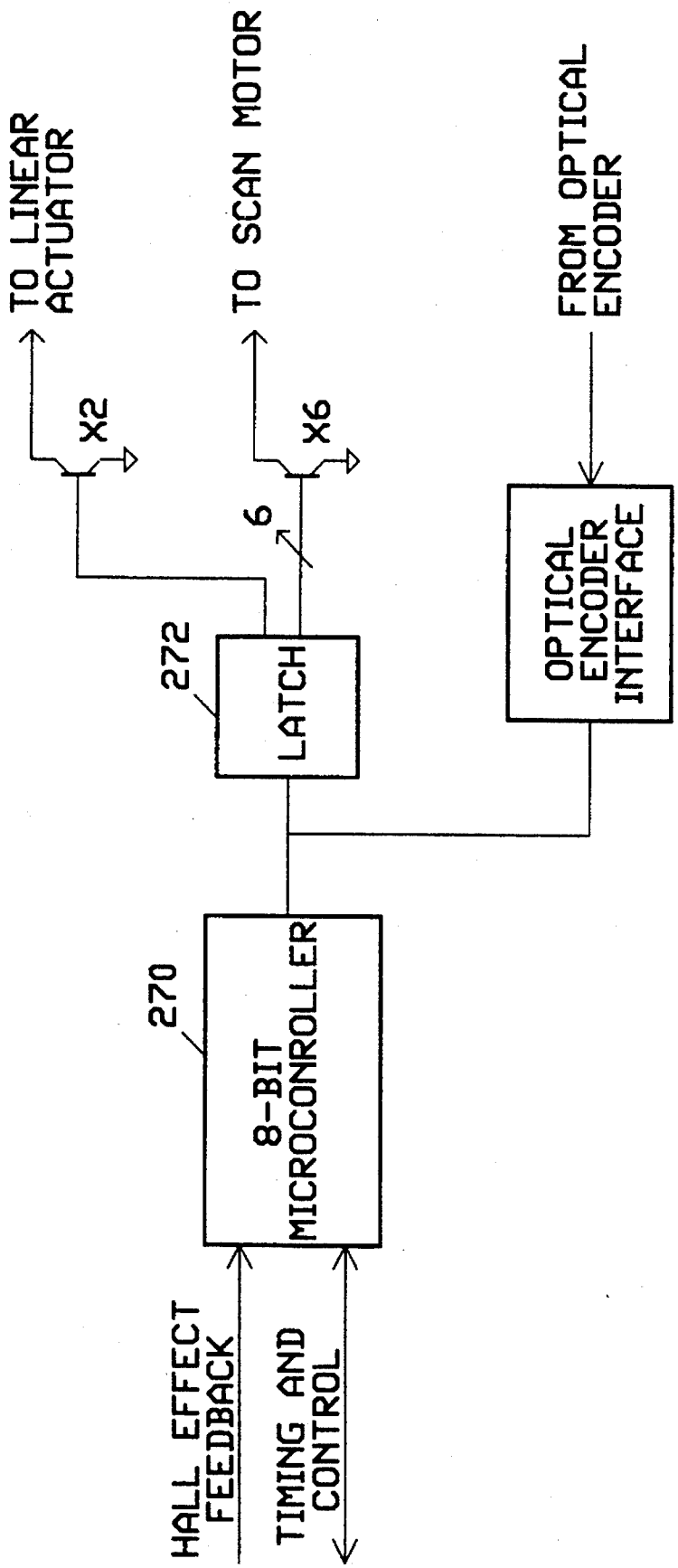
FIG. 22 is a schematic block diagram illustrating the scan controller of the system of FIG. 1.
Figure 23A:
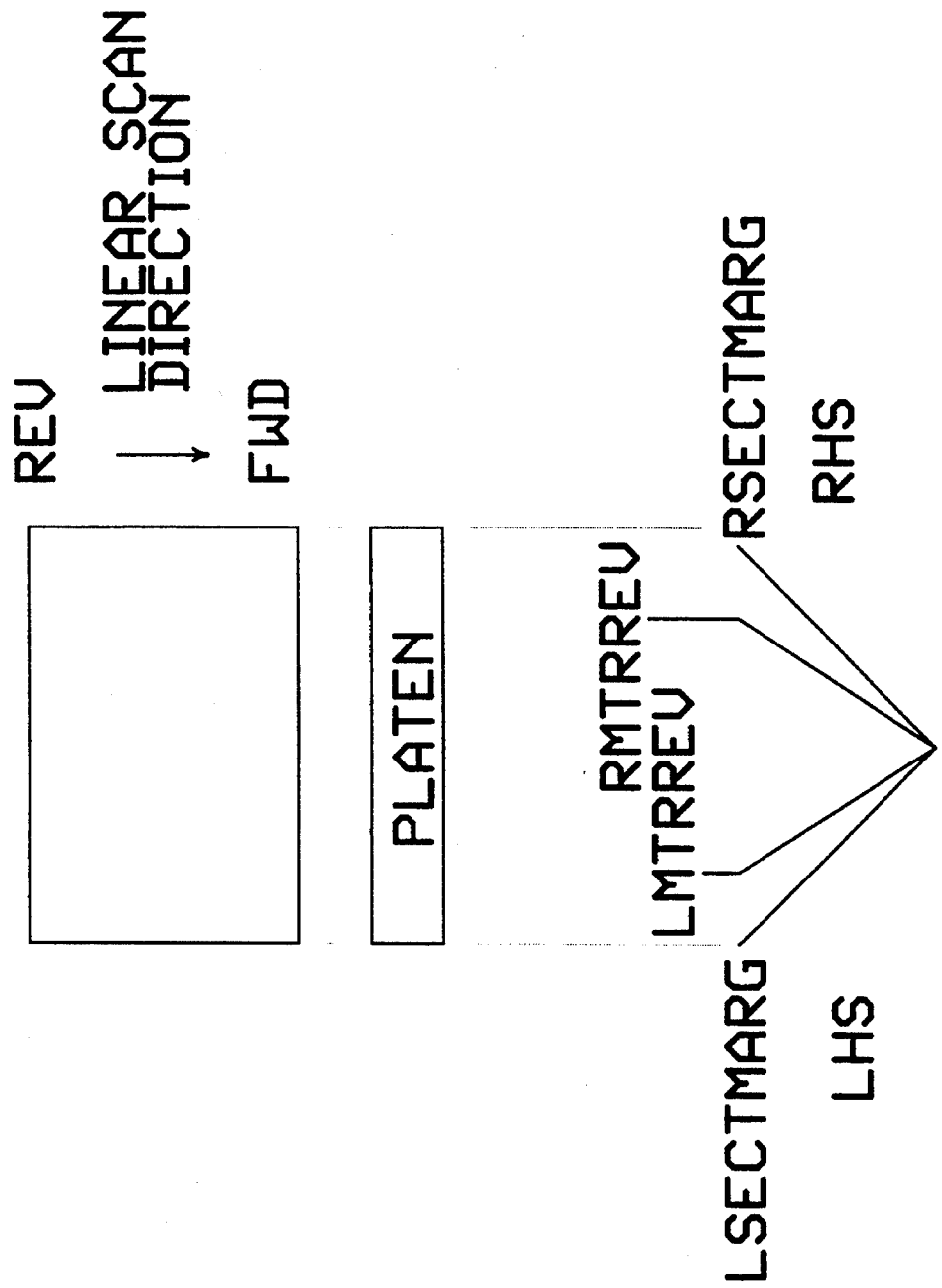
FIGS. 23A–23F are diagrammatic views providing a software flow chart for further illustrating the operation of the method and apparatus of the present invention.
Figure 23B:
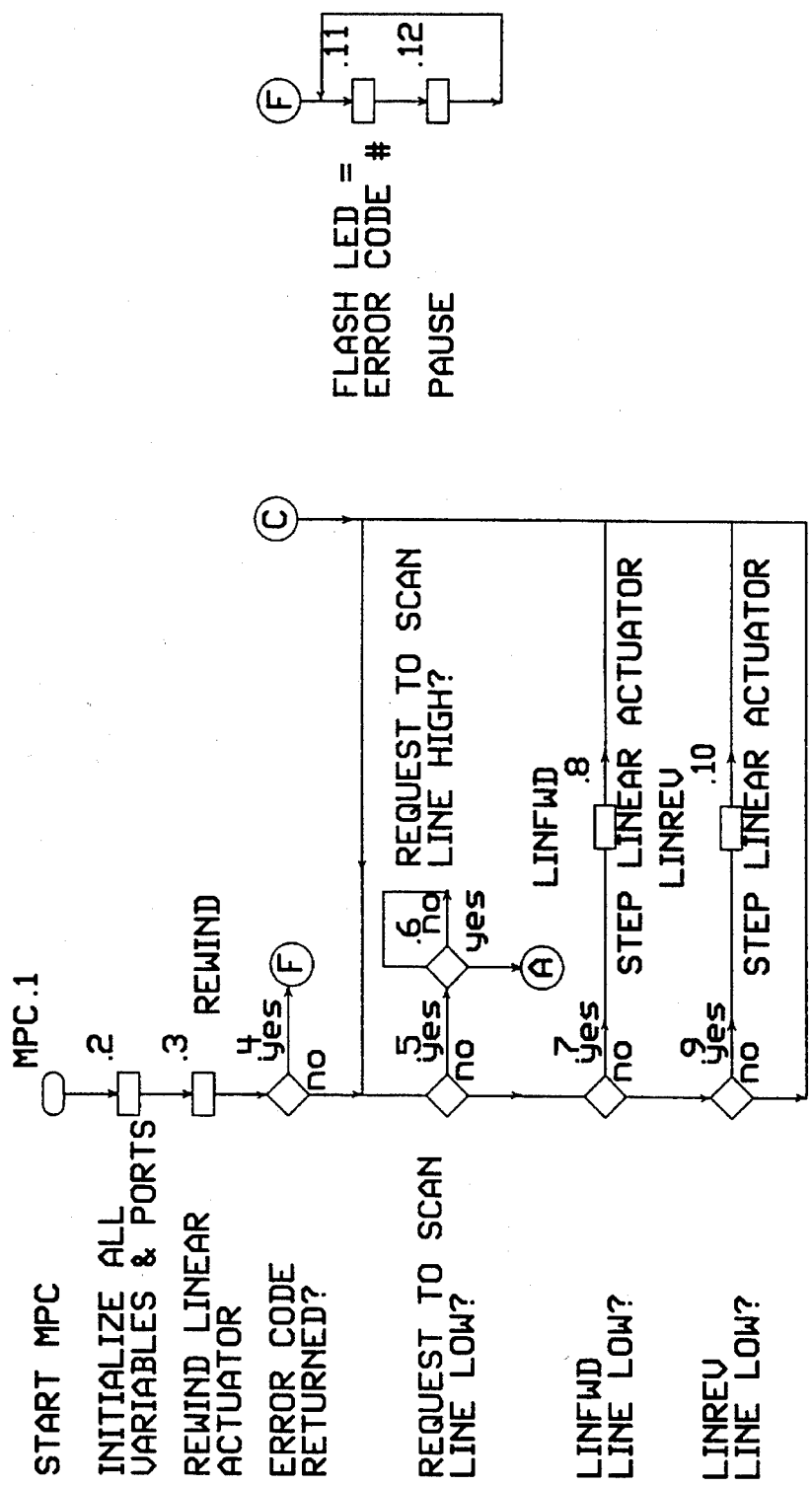
Figure 23C:
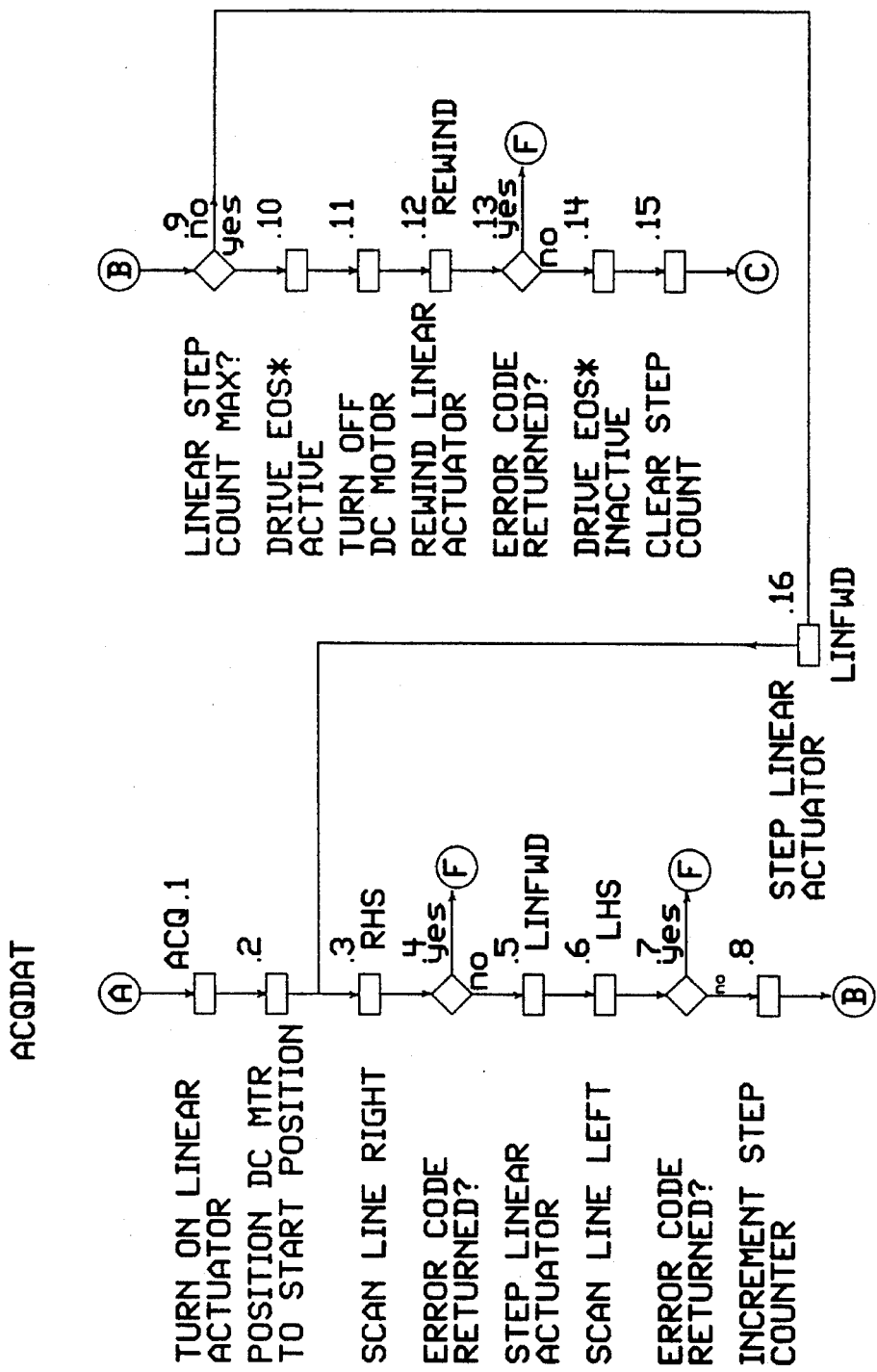
Figure 23D:
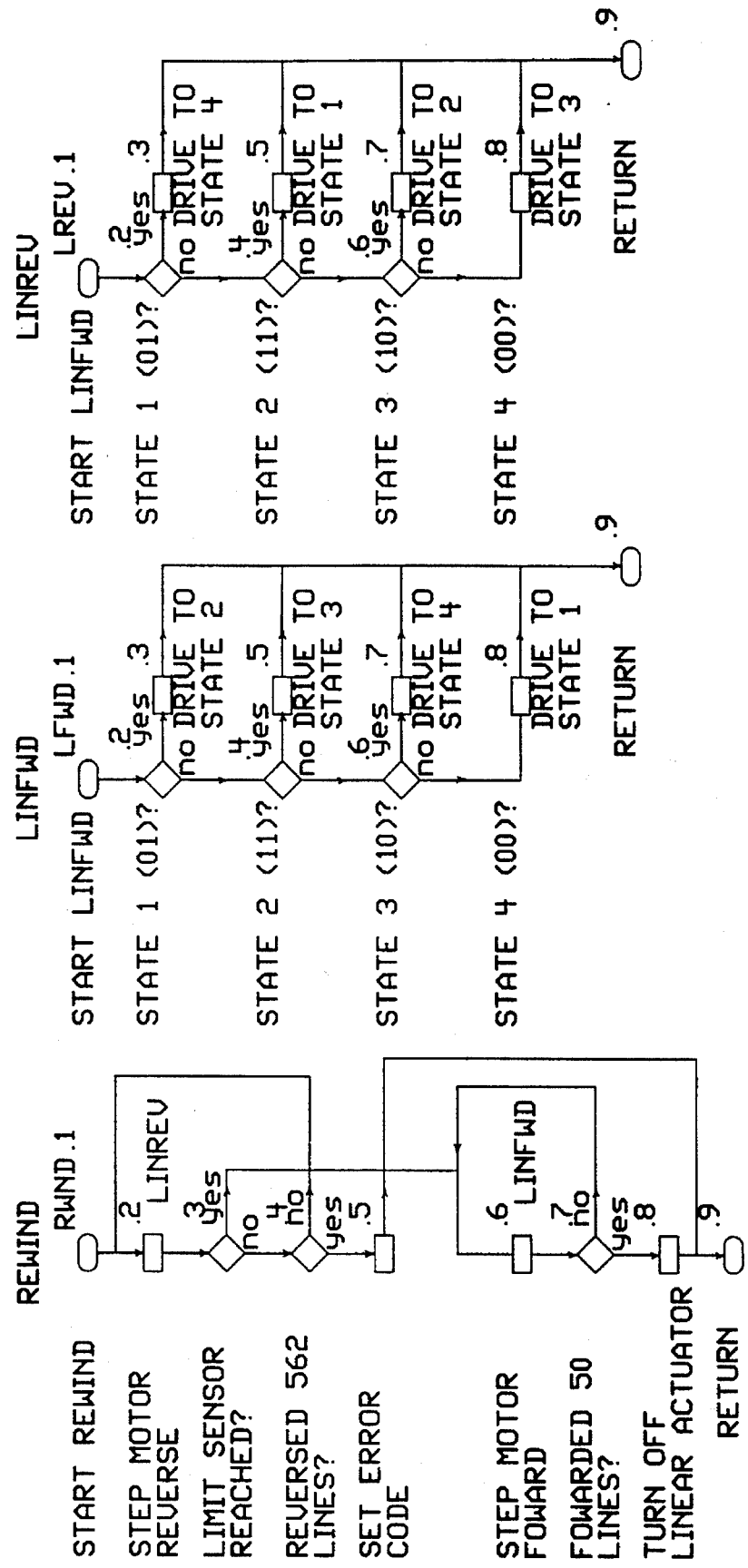
Figure 23E:
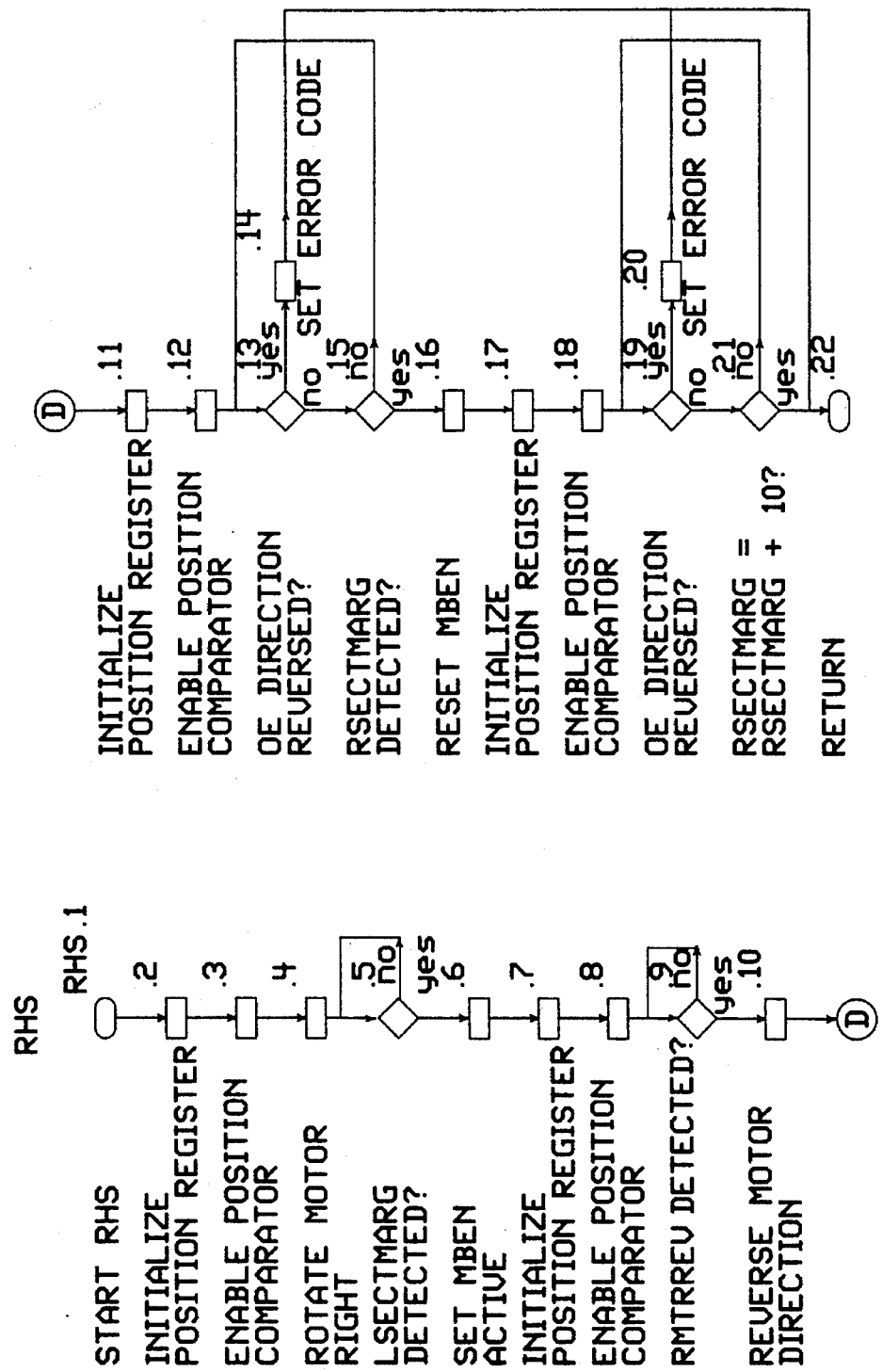
Figure 23F:
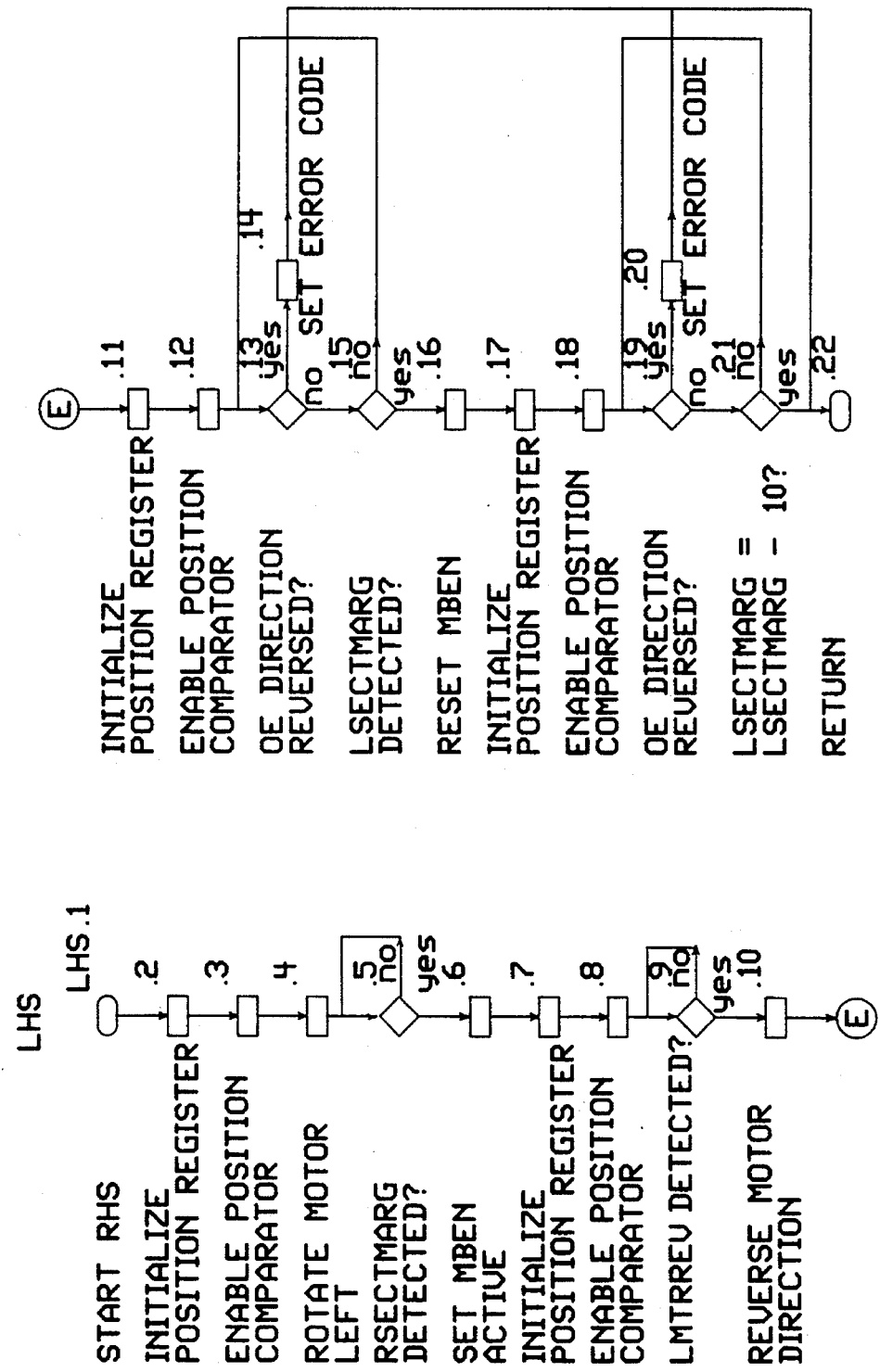

The scan controller 14 is responsible for controlling the scan motion of the two motors 38 and 40 associated with the probe assembly 12. It uses an 8 bit programmable microcontroller running control software as will be described. A functional block diagram of the scan controller is given in FIG. 22. The microcontroller 270 is responsible for sending the necessary commands to control each of the motors, receive positional feedback information from an optical encoder and hall effect sensors that are attached to the motor, and provide the necessary timing and control signals to the remainder of the system. One of the motors to be controlled by the scan controller is the scan motor 38 responsible for oscillating the transducer 34 back and forth over a limited range of angle. One type of motor that can be used for this purpose is a 3 phase DC brushless motor. These motors exhibit a high rate of efficiency and can therefore create large amounts of torque in physically small motor sizes. Furthermore, the absence of brushes to perform the commutation makes for a long term reliable system. The DC brushless motor has three windings which are required to have current either sourced to them or sunk from them independent of each other in order to make them rotate. Therefore, six separate sets of high voltage high current drivers are needed to perform this task. The control bits to the six drivers are driven from an 8 bit latch 272. The latch is used as an extension of the I/O lines that are available from the microcontroller 270. These bits can be set to a logic '1' or logic '0' depending on the desired motion of the motor. As the motor changes its position, sensors internal to the motor provide feedback as to the relative angular position of the motor. The type of sensor that is most often used for this application is the hall effect sensors. The hall effect sensor output is a logic '1' or '0' which decodes the position of the motor to within certain resolution limits. The states of these sensors are driven to the microcontroller 270 where they are read and a decision is made based on their value as to what the next state of the drive outputs should be.

The microcontroller 270 runs assembly level language software which is responsible for the overall functionality of the scan controller 14 as well as establishing the system timing. A software flow chart depicting the logic flow of the software is given in FIG. 23 and a system timing diagram is given in FIG. 24. Each of the individual logic elements of the flow chart is described in the following table:

TABLE I

| | Flow Chart Logic Elements | |
|---|---|---|
| MPC.1 | START MPC - | This is the main routine for overall program control and invoking the necessary subroutines when appropriate. |
| MPC.2 | INITIALIZE ALL VARIABLES AND PORTS | The internal counters and registers used throughout the software, along with the individual I/O lines found on the microcontroller, are all initialized at this time. |
| MPC.3 | REWIND LINEAR ACTUATOR | The linear actuator is rewound to its starting position on power up. Should the Rewind subroutine be unable to successfully rewind the linear actuator, then an error condition exists. |
| MPC.4 | ERROR CODE RETURNED | |
| MPC.5 | REQUEST TO SCAN LINE LOW | The software now looks for the request to scan line to be pulled active (low). This is the first step in initiating a scan. |
| MPC.6 | REQUEST TO SCAN LINE HIGH | The software does not begin to process the request to scan until the request to scan signal has been removed. In the case of a switch driving the signal, the switch must be released. |
| MPC.7 | LINFWD LINE LOW | Assuming a request to scan has not been initiated, the software checks for a second request. This is a request to single step the linear actuator forward by one step. The purpose for doing this is to allow manual positioning of the linear actuator for testing purposes. |
| MPC.8 | LINFWD | This is the actual call to the subroutine to move the linear actuator forward by one position. |
| MPC.9 | LINREV LINE LOW | A third request by the user in the form of single stepping the linear actuator in reverse is now checked for by the software. The purpose for doing this is to allow manual positioning of the linear actuator for testing purposes. |
| MPC.10 | LINREV | This is the actual call to the subroutine to move the linear actuator in reverse by one position. |
| | ACQDAT - | Acquire data is not a stand alone subroutine, but rather part of the main process control routine; however, is functionally significant enough to treat it as a subroutine and will, therefore, be described separately. The main purpose of this section of code is to call the necessary subroutines to perform an entire scan. In addition, this section of code is also responsible for driving various timing signals. |
| MPC.11 | FLASH LED = ERROR CODE # | Upon the detection of an error, all normal processing stops until a system reset occurs. Until a reset is initiated, the error code number is flashed at a relatively high rate in order to blink an LED on and off. This will allow a visual indication of what error had been detected. |
| MPC.12 | PAUSE | A short time delay between successive flashing of error codes is placed in order to distinguish the error code. |
| ACQ.1 | TURN ON LINEAR ACTUATOR | During normal operating mode while waiting for a request to scan, the linear actuator is powered down to conserve power. This is the point where the linear actuator gets powered up in preparation to begin a scan. |
| ACQ.2 | POSITION DC MTR TO START POSITION | During idle periods, the DC brushless motor responsible for moving the transducer is at rest in the center of the scan arc. At this point in time, the transducer is driven to the extreme side of the platen in preparation for a scan. |
| ACQ.3 | SCAN LINE RIGHT | The transducer is sitting at the extreme left side of the platen. The software now gives the command to scan the platen over to the far right side. |
| ACQ.4 | ERROR CODE RETURNED | If the subroutine RHS was unable to successfully scan the line, then an error condition exists and the software checks for that condition at this point in the code. |
| ACQ.5 | STEP LINEAR ACTUATOR | Assuming no error codes from RHS were detected, then the linear actuator is stepped to the next line in preparation for the next scan. |
| ACQ.6 | SCAN LINE LEFT | The transducer is sitting at the extreme right side of the platen. The software now gives the command to scan the platen over to the far left side. |
| ACQ.7 | ERROR CODE RETURNED | If the subroutine LHS was unable to successfully scan the line, then an error condition exists and the software checks for that condition at this point in the code. |
| ACQ.8 | INCREMENT STEP COUNTER | The internal counter used to track the number of lines scanned is now incremented. |
| ACQ.9 | LINEAR STEP COUNT MAX | A check is made to determine if the total number of lines to be scanned has been reached. |
| ACQ.10 | DRIVE EOS* ACTIVE | If the total number of lines to be scanned has been met, then the scan is complete and End of Scan is driven active (low). |
| ACQ.11 | TURN OFF DC MOTOR | At this point in time, power to the DC motor is removed and scanning is stopped. |
| ACQ.12 | REWIND LINEAR ACTUATOR | The linear actuator is rewound to its starting position. |

TABLE I-continued

Flow Chart Logic Elements

| | | |
|---|---|---|
| ACQ.13 | ERROR CODE RETURNED | Should the Rewind subroutine be unable to successfully rewind the linear actuator, then an error condition exists. |
| ACQ.14 | DRIVE EOS* INACTIVE | Once rewinding is complete, EOS* can be driven inactive in preparation for the next scan. |
| ACQ.14 | CLEAR STEP COUNT | The internal counter used for tracking the total number of lines scanned is now reset. |
| RWND.1 | START REWIND | The purpose of this subroutine is to rewind the linear actuator to its home position. The rewinding of the motor continues until one of two events occur. The first event is the normal termination due to the detection of the activation of the position sensor mounted at the end of the linear travel path. Once the sensor has become active, the motor is stepped forward 50 steps or 0.01". This is in order to remove any mechanical play in the overall travel mechanism. The second event that could terminate the rewinding of the motor is that over 550 step commands would have been issued. In this case, it is clear that the total number of step commands issued to the motor has exceeded the required number of commands to fully rewind the motor. In this case, something has failed either in the motor and/or associated drive circuitry, or the sensor itself; therefore, the software no longer continues sending out rewind commands to the motor. |
| RWDN.2 | STEP MOTOR REVERSE | This is a call to the subroutine responsible for stepping the motor in the reverse or rewind direction by 1 step which equates to 0.002". |
| RWND.3 | LIMITED SENSOR REACHED | A check is performed to determine if the sensor indicating home position of the linear actuator has been reached. |
| RWND.4 | REVERSED 562 LINES | Provided that the limit sensor has not been activated, a check is made to see if the maximum number of rewind commands has been given. |
| RWND.5 | SET ERROR CODE | If the motor has been reversed 562 lines without the limit sensor activating, then an error condition exists and an error code indicating such is returned. |
| RWND.6 | STEP MOTOR FORWARD | Normal termination of the rewind has taken place and the motor is now stepped forward by 50 steps to remove any mechanical play in the system. |
| RWND.7 | FORWARD 50 LINES | A check to see if the motor has been stepped forward by the total amount |
| RWND.8 | TURN OFF LINEAR ACTUATOR | This completes the rewind subroutine and power is removed from the motor to conserve overall energy |
| RWND.9 | RETURN | Return from subroutine. |
| LFWD.1 | START LINFWD | The purpose of this subroutine is to step the linear actuator forward by one position of 0.002". |
| LFWD.2 | STATE 1 | This is a check to see if the linear actuator is in 1 of the 4 possible states. |
| LFWD.3 | DRIVE TO STATE 2 | Assuming the linear actuator was in State 1, the motor is driven to State 2. |
| LFWD.4 | STATE 2 | This is a check to see if the linear actuator is in State 2 of the 4 possible states. |
| LFWD.5 | DRIVE TO STATE 3 | Assuming the linear actuator was in State 2, the motor is driven to State 3. |
| LFWD.6 | STATE 3 | This a check to see if the linear actuator is in State 3 of the 4 possible states. |
| LFWD.7 | DRIVE TO STATE 4 | Assuming the linear actuator was in State 3, the motor is driven to State 4. |
| LFWD.8 | DRIVE TO STATE 1 | Since the motor was determined to not be in States 1–3, it must be in State 4 and, therefore, will be driven to State 1. |
| LFWD.9 | RETURN | Return from subroutine. |
| LREV.1 | START LINREV | The purpose of this subroutine is to step the linear actuator in reverse by one position or 0.002". |
| LREV.2 | STATE 1 | This is a check to see if the linear actuator is in 1 of the 4 possible states. |
| LREV.3 | DRIVE TO STATE 4 | Assuming the linear actuator was in State 1, the motor is driven to State 4. |
| LREV.4 | STATE 2 | This is a check to see if the linear actuator is in State 2 of the 4 possible states. |
| LREV.5 | DRIVE TO STATE 1 | Assuming the linear actuator was in State 2, the motor is driven to State 1 . |
| LREV.6 | STATE 3 | This is a check to see if the linear actuator is in State 3 of the 4 possible states. |
| LREV.7 | DRIVE TO STATE 2 | Assuming the linear actuator was in State 3, the motor is driven to State 2. |
| LREV.8 | DRIVE TO STATE 1 | Since the motor was determined to not be in States 1–3, it must be in State 4 and, therefore, will be driven to State 3. |
| LREV.9 | RETURN | Return from subroutine. |
| RHS.1 | START RHS | The purpose of this subroutine is to drive the motor to the right side of the platen and generate the appropriate control for setting and clearing MBEN. |
| RHS.2 | INITIALIZE POSITION REGISTER | An eight bit register is used to hold the value of the angular position out of the optical encoder to set and reset the MBEN timing pulse. This register is loaded by the software several times during a single scan sweep. |
| RHS.3 | ENABLE POSITION COMPARATOR | Once the eight bit position register has been loaded, the comparator is enabled to begin checking the output of the optical encoder against the position register outputs. |
| RHS.4 | ROTATE MOTOR RIGHT | This command is responsible for starting the motor rotating to the right side of the platen. |
| RHS.5 | LSECTMARG DETECTED | As the motor begins to rotate to the right side of the platen, the software monitors the output of the comparator for a detection. Once a detection has occurred, the software can reload the position register in preparation for the next position check. |

TABLE I-continued

Flow Chart Logic Elements

| | | |
|---|---|---|
| RHS.6 | SET MARGIN ACTIVE | MBEN timing signal is driven active. |
| RHS.7 | INITIALIZE POSITION REGISTER | Reload the position register to search for RMTRREV. |
| RHS.8 | ENABLE POSITION COMPARATOR | Enable the position comparator to look for RMTRREV. |
| RHS.9 | RMTRREV DETECTED | The software waits until the motor reaches the reverse motor point for the right side of the platen. |
| RHS.10 | REVERSE MOTOR DETECTION | The direction of the motor is reversed in an effort to slow it down as quickly as possible. |
| RHS.11 | INITIALIZE POSITION REGISTER | Reload the position register to search for RSECTMARG. |
| RHS.12 | ENABLE POSITION COMPARATOR | Enable the position comparator to look for RSECTMARG. |
| RHS.13 | OE DIRECTION REVERSED | The direction bit out of the optical encoder is checked for a direction change. If the motor is able to slow down and reverse before the RSECTMARG is detected, then an error condition exists. |
| RHS.14 | SET ERROR CODE | An error code indicating the appropriate error condition is set. |
| RHS.15 | RSECTMARG DETECTED | The software waits until the far right side of the platen has been detected. Once this occurs, MBEN is reset and the line scan is complete. |
| RHS.16 | RESET MBEN | Drive MBEN inactive. |
| RHS.17 | INITIALIZE POSITION REGISTER | Reload the position register to look for a count of RSECTMARG +10. This ensures enough overshoot to keep MBEN inactive long enough to satisfy data buffer requirements. |
| RHS.18 | ENABLE POSITION COMPARATOR | Enable the position comparator to look for RSECTMARG +10. |
| RHS.19 | OE DIRECTION REVERSED | The direction bit out of the optical encoder is checked for a direction change. If the motor is able to slow down and reverse before LSECTMARG is detected, then an error condition exists. |
| RHS.20 | SET ERROR CODE | An error code indicating the appropriate error condition is set. |
| RHS.21 | RSECTMARG +10 DETECTED | The software waits until the far right side of the platen plus 10 additional counts has been detected. Once this occurs, the motor has traveled far enough to meet all necessary timing requirements and can reverse anytime hereinafter. |
| RHS.22 | RETURN | Return from subroutine. |
| LHS.1 | START LHS | The purpose of this subroutine is to drive the motor to the left side of the platen and generate the appropriate control for setting and clearing MBEN. |
| LHS.2 | INITIALIZE POSITION REGISTER | An eight bit register is used to hold the value of the angular position out of the optical encoder to set and reset the MBEN timing pulse. This register is loaded by the software several times during a single scan sweep. Once the eight bit position register has been coded, the comparator is enabled to begin checking the output of the optical encoder against the position register outputs. |
| LHS.3 | ENABLE POSITION COMPARATOR | |
| LHS.4 | ROTATE MOTOR LEFT | This command is responsible for starting the motor rotating to the left side of the platen. |
| LHS.5 | RSECTMARG DETECTED | As the motor begins to rotate to the left side of the platen, the software monitors the output of the comparator for a detection. Once a detection has occurred, the software can reload the position register in preparation for the next position check. |
| LHS.6 | SET MBEN ACTIVE | MBEN timing signal is driven active. |
| LHS.7 | INITIALIZE POSITION REGISTER | Reload the position register to search for LMTRREV. |
| LHS.8 | ENA13LE POSITION COMPARATOR | Enable the position comparator to look for LMTRREV. |
| LHS.9 | LMTRREV DETECTED | The software waits until the motor reaches the reverse motor point for the left side of the platen. |
| LHS.10 | REVERSE MOTOR DIRECTION | The direction of the motor is reversed in an effort to slow it down as quickly as possible. |
| LHS.11 | INITIALIZE POSITION REGISTER | Reload the positin register to search for LSECTMARG. |
| LHS.12 | ENABLE POSITION COMPARATOR | Enable the position comparator to look for LSECTMARG. |
| LHS.13 | OE DIRECTION REVERSED | The direction bit out of the optical encoder is checked for a direction change. If the motor is able to slow down and reverse before the LSECTMARG is detected, then an error condition exists. |
| LHS.14 | SET ERROR CODE | An error code indicating the appropriate error condition is set. |
| LHS.15 | LSECTMARG DETECTED | The software waits until the far left side of the platen has been detected. Once this occurs, MBEN is reset and the line scan is complete. |
| LHS.16 | RESET MBEN | Drive MBEN inactive. |
| LHS.17 | INITALIZE POSITION REGISTER | Reload the position register to look for a count of LSECTMARG +10. This ensures enough overshoot to keep MBEN inactive long enough to satisfy data buffer requirements. |
| LHS.18 | ENABLE POSITIN COMPARATOR | Enable the position comparator to look for LSECTMARG +10. |
| LHS.19 | OE DIRECTION REVERSED | The direction bit out of the optical encoder is checked for a direction change. If the motor is able to slow down and reverse before RSECTMARG is detected, then an error condition exists. |
| LHS.20 | SET ERROR CODE | An error code indicating the appropriate error condition is set. |
| LHS.21 | LSECTMARG +10 DETECTED | The software waits until the far left side of the platen plus 10 additional counts has been detected. Once this occurs, the motor has traveled far enough to meet all necessary timing requirements and can |

TABLE I-continued

Flow Chart Logic Elements

| | | |
|---|---|---|
| | | reverse anytime hereinafter. |
| LHS.22 | RETURN | Return from subroutine. |

Figure 24:
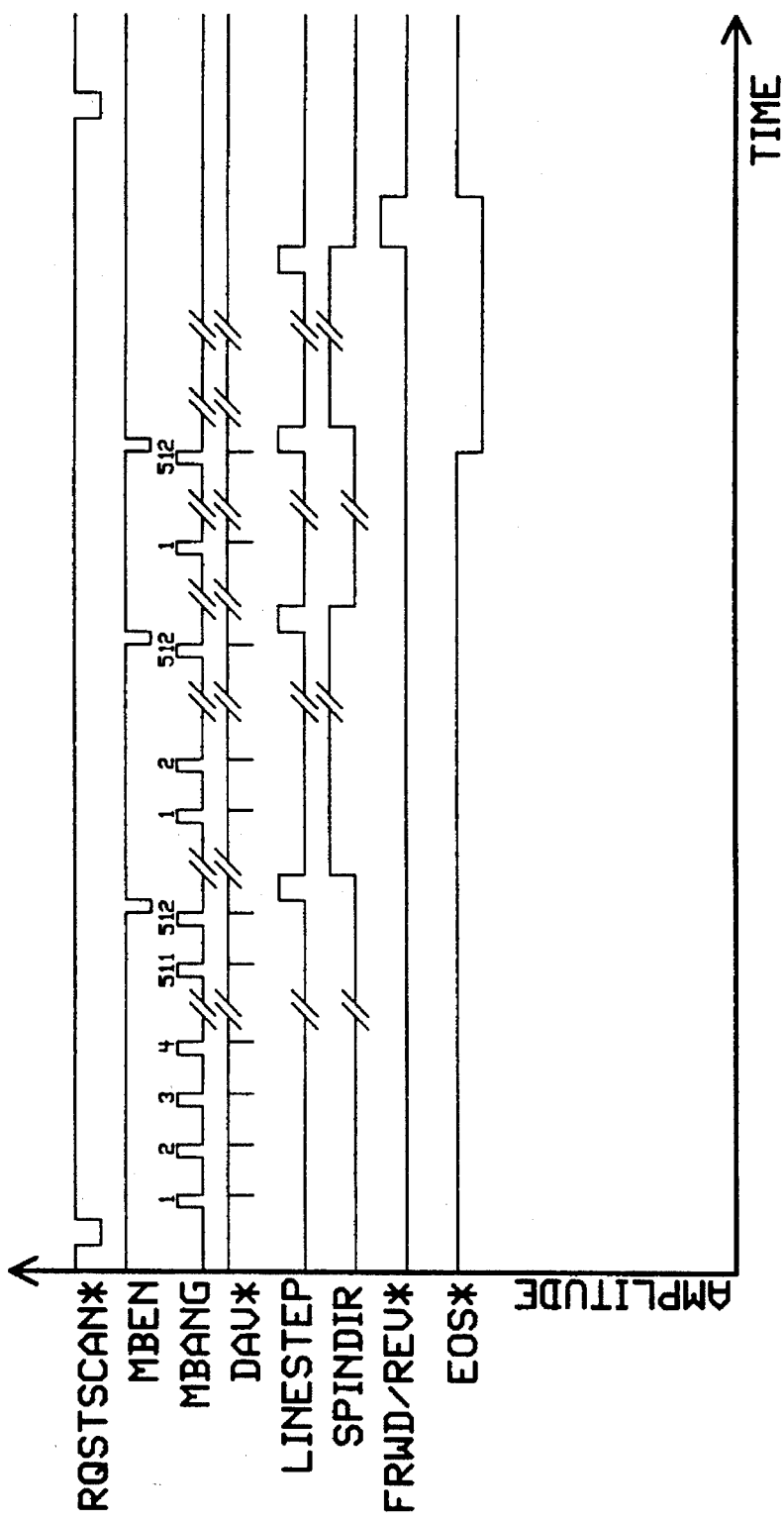
FIG. 24 is a graph illustrating waveforms illustrating system timing for the method and apparatus of the present invention.

Referring to the system timing diagram of FIG. 24, RQSTSCAN is the request to scan signal used in the START MPC routine, MBEN is the main bang enable pulse, MBANG is the main bang pulse, DAV is a data available pulse for operating data buffer 18 as will be described, LINESTEP is a pulse which commands the linear actuator 40 to move to the next line to be scanned, SPINDIR is a pulse signal which controls the direction of rotation of motor 38, FRWD/REV is a pulse signal which controls the direction of movement of linear actuator 40 and EOS is the end of scan signal used in the ACQDAT subroutine.

Figure 25:
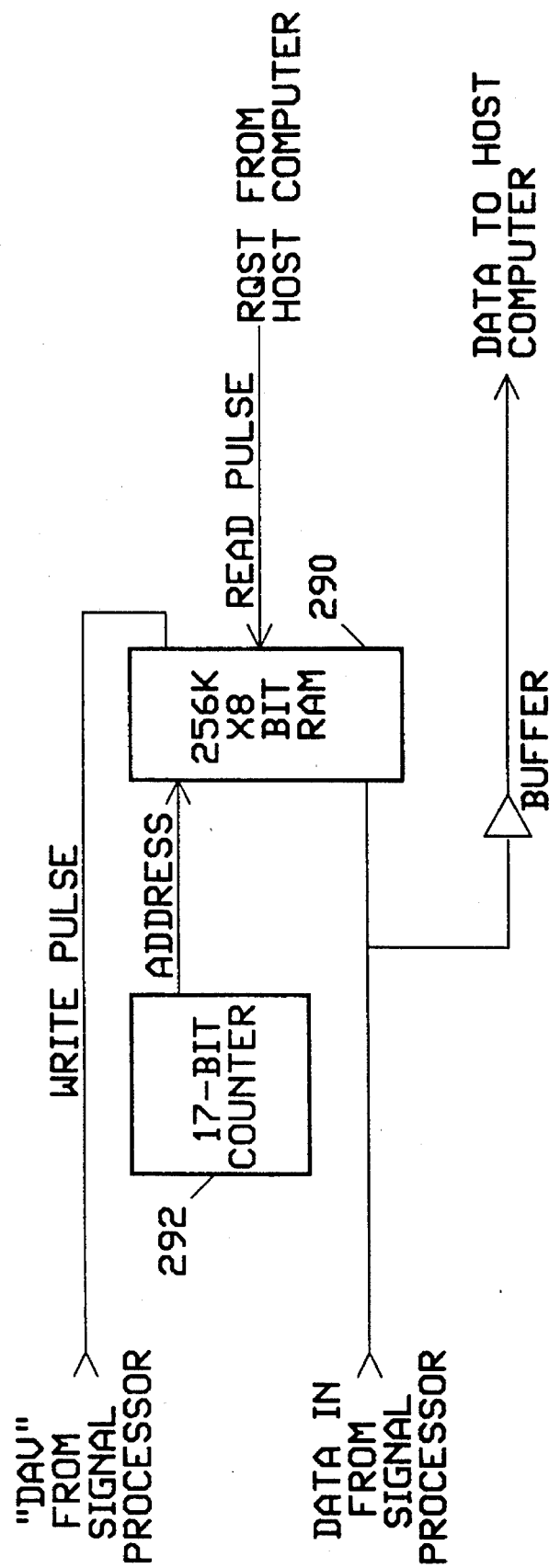
FIG. 25 is a block diagram illustrating the data buffer of the system of FIG. 1.

The data buffer 18 acts as a FIFO (first in first out) data storage array. Due to speed limitations that generally exist in the computers used to process the captured image, the ultrasonic reader can supply data at a faster rate than the post processors can receive it. To avoid slowing the scan down and preventing the user from having to hold their finger on the platen 30 for an inordinate amount of time, the data buffer 18 acts as a temporary storage device for an entire scan worth of data and allows the post processor to read this data at a slower rate once the scan has been completed. A functional block diagram of data buffer 18 is given in FIG. 25.

The data buffer 18 is arranged as 512 rows by 512 columns of 8 bit data. When valid data from the signal processor is available, a data available pluse (DAV) is driven active. The DAV pulse is used by the data buffer 18 to write the data into a RAM 290 and increment an address counter 292. Each row may contain up to a maximum of 512 data points. At the end of the row, a Main Bang Enable pulse (MBEN) is driven which indicates to the data buffer 18 to move to the next row. The current state of the address counter 292 which also corresponds to the total number of data points in the first row of data, is now stored in a nine bit latch (not shown) for later use by the post processor. As data for the second row of scanning becomes available, the address counter 292 is decremented starting from the maximum count of the previous row down to zero. Each subsequent scan line alternately increments and decrements the address counter 292 as described above.

After all data has been written into the data buffer 18, the post processor can now read the data. The data is read in the same manner in which it was stored, with two exceptions. Prior to any data being read, the post processor must first read the nine bit data latch to determine the number of data points to read for each row. The post processor then generates a read pulse similar to the DAV pulse for each data point of each row. Secondly, the post processor must read all 512 rows regardless of the actual number of rows in which data was stored.

In order to decrease the overall scan time of the system, the human or animal tissue, i.e. the finger, must be scanned at a faster rate. This can be accomplished by one of two ways. The first is to increase the speed of the motor 38. This requires a larger, more powerful motor and rapidly becomes physically cumbersome to design around, as well as expensive. The second approach, and the one described herein, uses multiple transducers to capture several points on the finger simultaneously. Simply, if two transducers are used, then each transducer is required to scan only half of the surface of the finger, three transducers—one-third, etc. With the addition of each transducer, the scan time reduces proportionately. A multiple transducer approach is illustrated diagrammatically in FIG. 26. Since the transducers scan along an arc, the multiple transducer approach must ensure that each transducer is scanning at a radius equal to that of the other transducers. This is to ensure that the total data captured is along a continuous line in order for the linearization algorithm to work.

Figure 26:
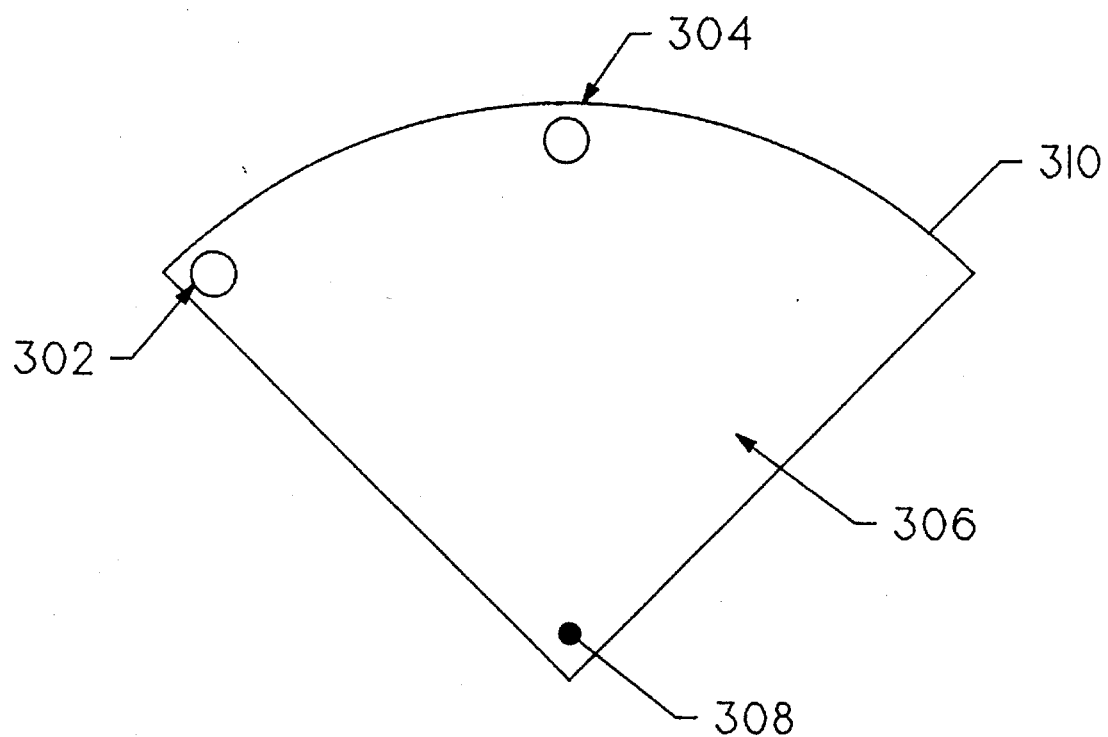
FIG. 26 is a diagrammatic view illustrating a multiple transducer approach for the probe of the present invention.

In particular, and referring to FIG. 26, a plurality of transducers, in the present illustration the two transducers 302 and 304, are supported by means including a pie-shaped element 306. Each transducer 302, 304 can be identical to transducer 34 in the probe means of FIG. 2, and element 306 is provided in place of probe arm 48. Element 306 is connected to the output shaft of the probe oscillatory motor, i.e. to the shaft of motor 38, for oscillatory movement about a pivot axis designated 308 in FIG. 26. As in the probe of FIG. 2, transducers 302, 304 are positioned closely adjacent to the platen which supports the human or animal tissue, i.e. the finger, for imaging the same. The transducers 302, 304 are in spaced relation along a transducer path which in the present illustration has a curvature corresponding to arcuate edge 310 of element 306 and joins the centers of the transducers 302, 304. The correction of the output shaft of the oscillatory motor, i.e. motor 38, to element 306 for pivotal or oscillating movement about axis 308 moves the transducers 302, 304 along a first scanning path along the surface of the platen so that the transducer path is in registry with the first scanning path and each of the ultrasonic beams from transducers 302, 304 is directed along a portion of the first scanning path in a manner such that the sum of the portions scanned equals the total length of the scanning path. In the arrangement of FIG. 26, the transducers 302, 304 are spaced equally along the transducer path. Thus, the portions of the first scanning path along which the ultrasonic beams are directed are equal and in sum equal the total length of the first scanning path. In the arrangement of FIG. 26, the transducer path and the first scanning path are arcuate and have a common radius which extends from pivot axis 308. A second motive means, i.e. in the form of linear actuator 40 in the probe of FIG. 2, moves the plurality of transducers 302, 304 along a second scanning path along the surface which second path is linear in a radial direction relative to the arcuate paths. In order to process the data returned from the transducers 302, 304 a high speed multiplexer preceded by a sample-and-hold circuit could be used. The scan controller 14 could multiplex between the multiple transducers in a controlled fashion to allow a sequencing of the data to take place.

In certain scanning applications it becomes necessary to scan an area larger than that illustrated in FIG. 3. For example, to satisfy certain Federal Bureau of Investigation fingerprint scanning requirements, the system of the present invention must scan an area of 35 mm.×35 mm. and scan the entire surface of the finger from one edge of the fingernail to the other edge of the fingernail. In order to scan the entire surface of the finger, i.e. from fingernail to fingernail, the flat platen previously described in connection with FIG. 2 must be changed to a curved platen. The curved platen comes into full contact with the perimeter of the finger and enables a much larger area to be scanned. The key to this approach is a method whereby the transducer will still collect the specular returns from the surface of the finger. To accomplish this, the transducer must be rotated about the axis of the cylindrical surface, i.e. the curved surface of the platen corresponding to the nail-to-nail surface of the finger. This can be achieved by the probe architecture shown in FIG. 27.

A curved platen 320 is semicylindrical in cross-sectional shape and has a semi-cylindrical, curved inner surface 322 adapted to receive the surface of a finger being scanned. The longitudinally extending edges 324, 326 of platen 320 are approximately in registry with the edges of the fingernail of a finger contacting surface 322. Platen 320 has a longitudinal axis 328 which is substantially coincident with the longitudinal axis of the finger being scanned. An oscillatory motor 330 similar to motor 38 in FIG. 2 is mounted at the center of the radius for the cylindrical lens or platen 320. In other words, the axis of the motor output shaft 332 is coincident with the longitudinal axis 328 of platen 320. A probe arm extends a transducer 340 just past the surface of the cylindrical lens or platen 320. Probe arm 338 has a first section 342 extending at a right angle to motor output shaft 322 and a second section 344 substantially parallel to shaft 322. Transducer 340 can be identical to transducer 34 in the probe of FIG. 2. The transducer 340 is then oscillated in a circular fashion along a given scan line. The entire assembly of motor 33, transducer arm and transducer 340 is stepped linearly by a linear actuator 346 fixed to a support 350 similar to linear actuator 40 in FIG. 2 and a second scan line is swept, similar to the flat platen approach.

Figure 27:
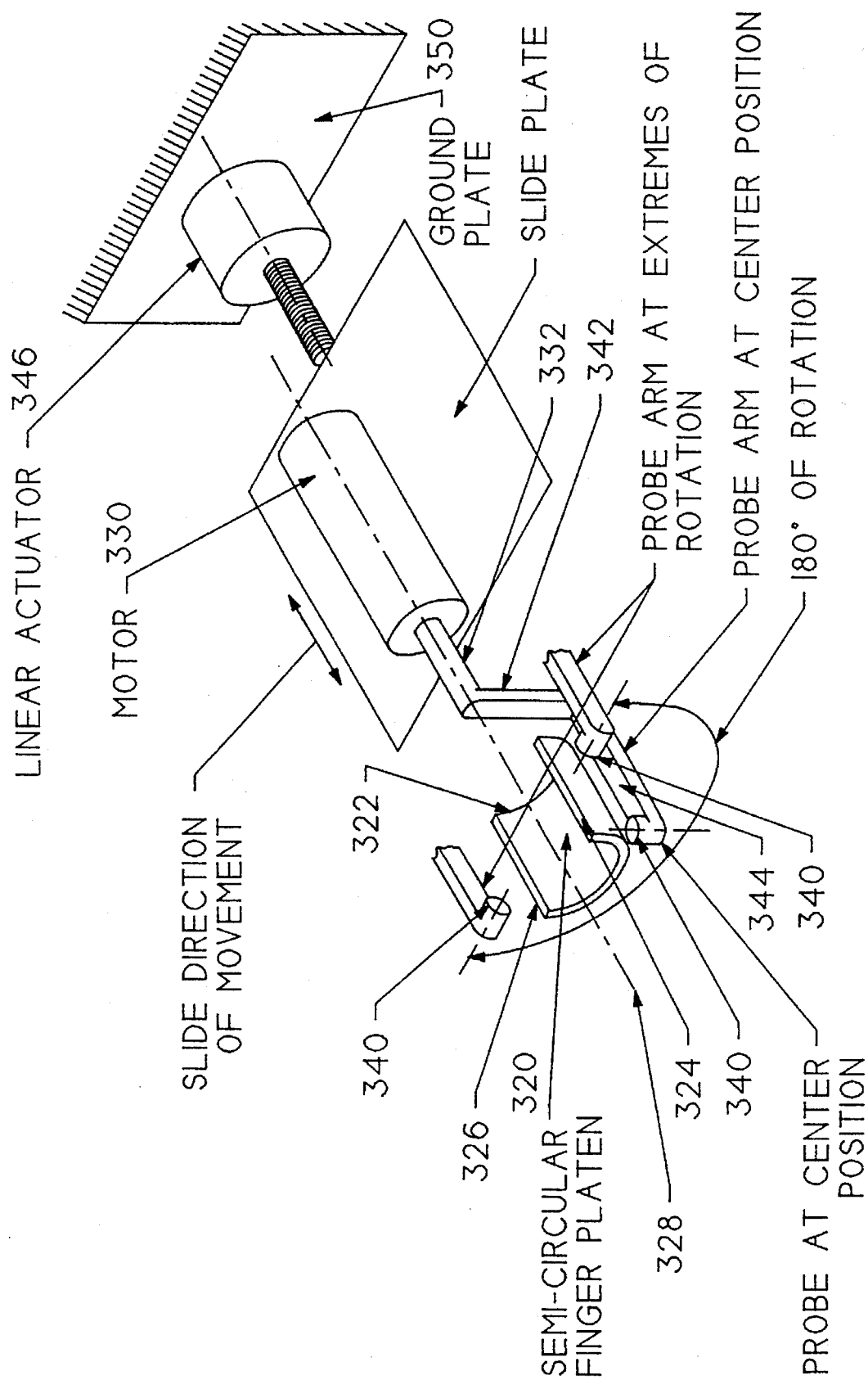
FIG. 27 is a fragmentary perspective view, partly diagrammatic, of an alternative probe architecture according to the present invention for fingerprint scanning.

The main difference in this approach is the fact that the circular sweep is along a linear path on the finger as opposed to the arc motion of the earlier approach. As a result, no linearization routines are required. FIG. 27 shows the probe arm 338 at the center and at both extremes of rotation through a 180° path. Again, this approach lends itself to multiple transducers for improved scan times. The transducers can now be mounted along a straight line axis where each is responsible for scanning a portion of the finger in the y-axis (i.e., different scan lines). This is in contrast to the previous approach where the multiple transducers each scanned on the same line.

There are several basic systems in which the system and method of the present invention can be configured. Such basic systems can be categorized fundamentally as identification systems wherein a finger is scanned and the system is responsible for identifying the individual, and verification systems wherein a finger is scanned and compared to a reference to verify that the individual is who he claims to be.

Figure 28:
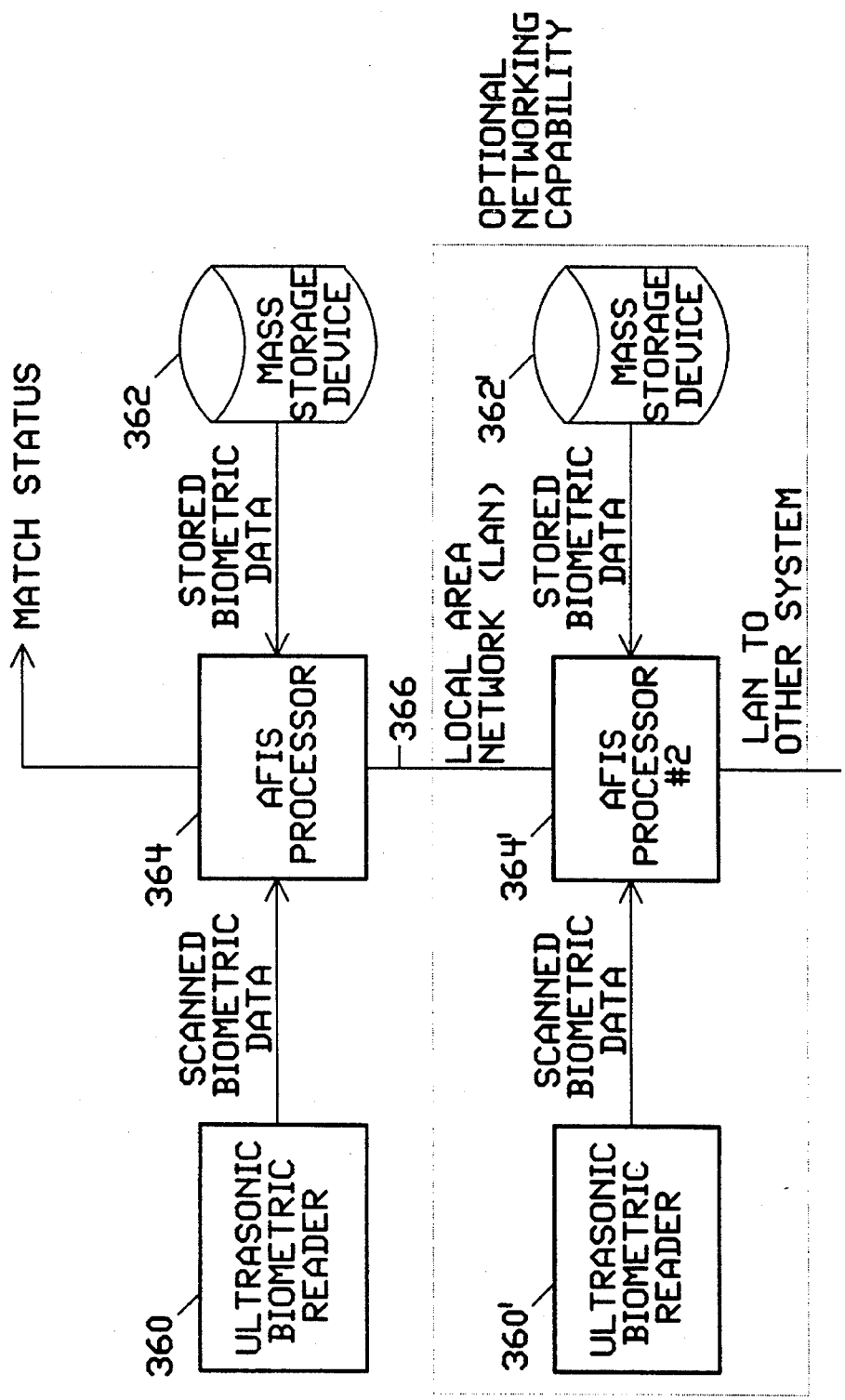
FIG. 28 is a block diagram illustrating the use of the system and method of the present invention in an identification system.

FIG. 28 illustrates the system and method of the present invention configured in an identification system which takes the image obtained from the scanned finger and compares it to a large database of previously scanned images to determine if a match exists. These identification systems, which typically are quite large and used by law enforcement agencies, immigration services and the like, have been generically termed AFIS or Automatic Fingerprint Identification Systems. Referring to FIG. 28 the ultrasonic biometric reader 360 comprises the system according to the present invention including probe assembly 12, signal processor 16, scan controller 14 and power supply 20. Data buffer 18 can be included if desired. There is provided means in the form of mass storage device 362 for storing a database of previously stored images, i.e. stored fingerprint images. There is also provided a system processor means 364 having inputs coupled to database storage means 362 and to the output of the processor in ultrasonic biometric reader 360 for comparing a scanned image from reader 360 to the previously stored images in device 362 to determine if a match exists. FIG. 28 also illustrates a second combination of ultrasonic biometric reader 360', mass store device 362' and processor 364' with local area network means 366 for connecting the processors 364 and 364' together.

Figure 29:
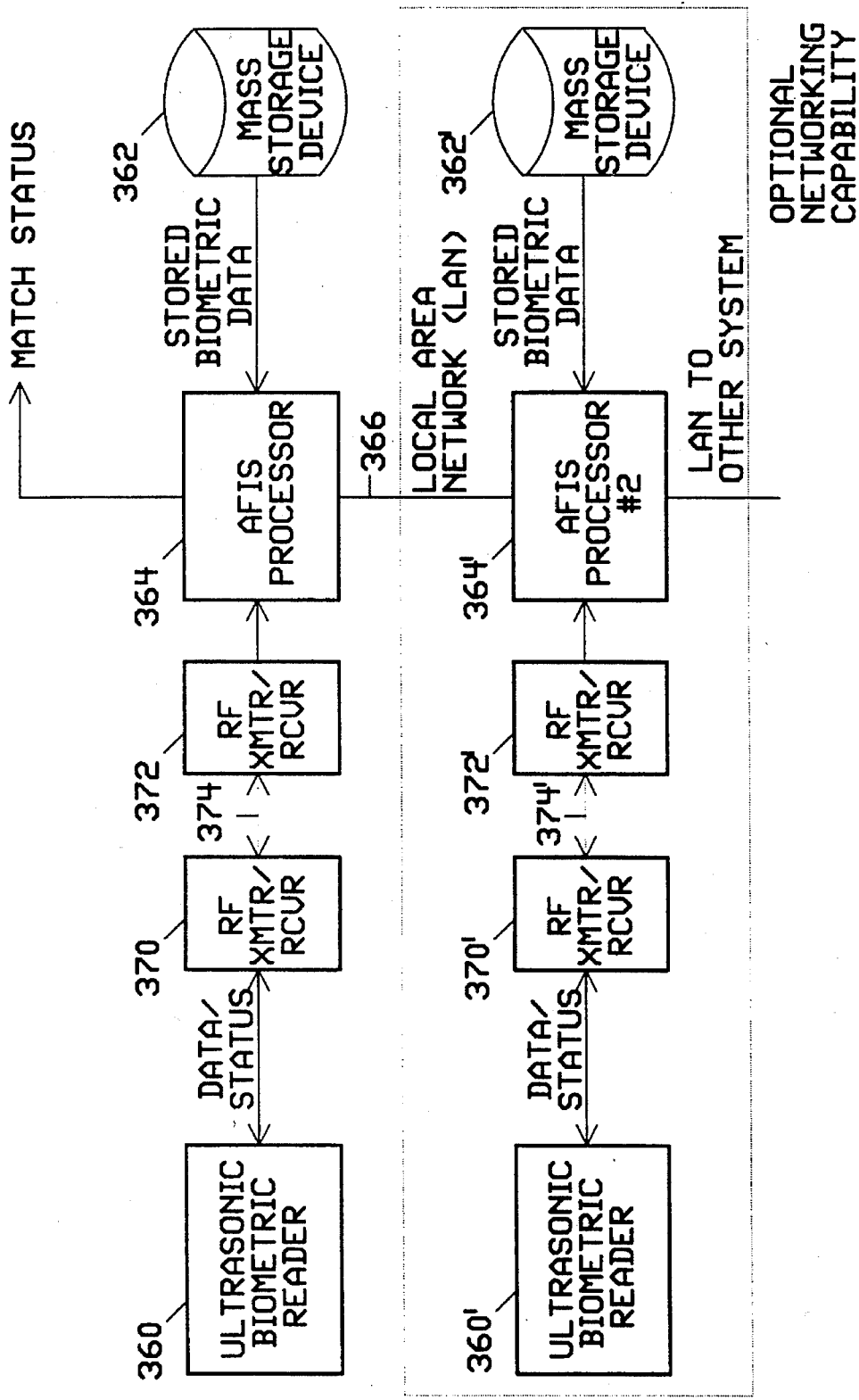
FIG. 29 is a block diagram illustrating a wireless version of the system of FIG. 28.

FIG. 29 illustrates an alternative arrangement wherein the hard-wired communication link between ultrasonic biometric reader 360 and processor 364 is replaced by a wireless communication link such as an RF transmitter/receiver 370 connected to the output of biometric reader 360, an RF transmitter/receiver/372 connected to the input of processor 364 and the transmission medium 374 therebetween. As a result, the ultrasonic biometric reader 360 can be located in a remote or mobile area such as a police car or other remote data entry site. A finger is placed on the reader, scanned and the data transmitted in a wireless manner to an AFIS processor for processing. The communication link is bi-directional and transmits back to the reader any pertinent information. Other wireless communication links can be employed such as optical, ultrasonic and the like.

Figure 30:
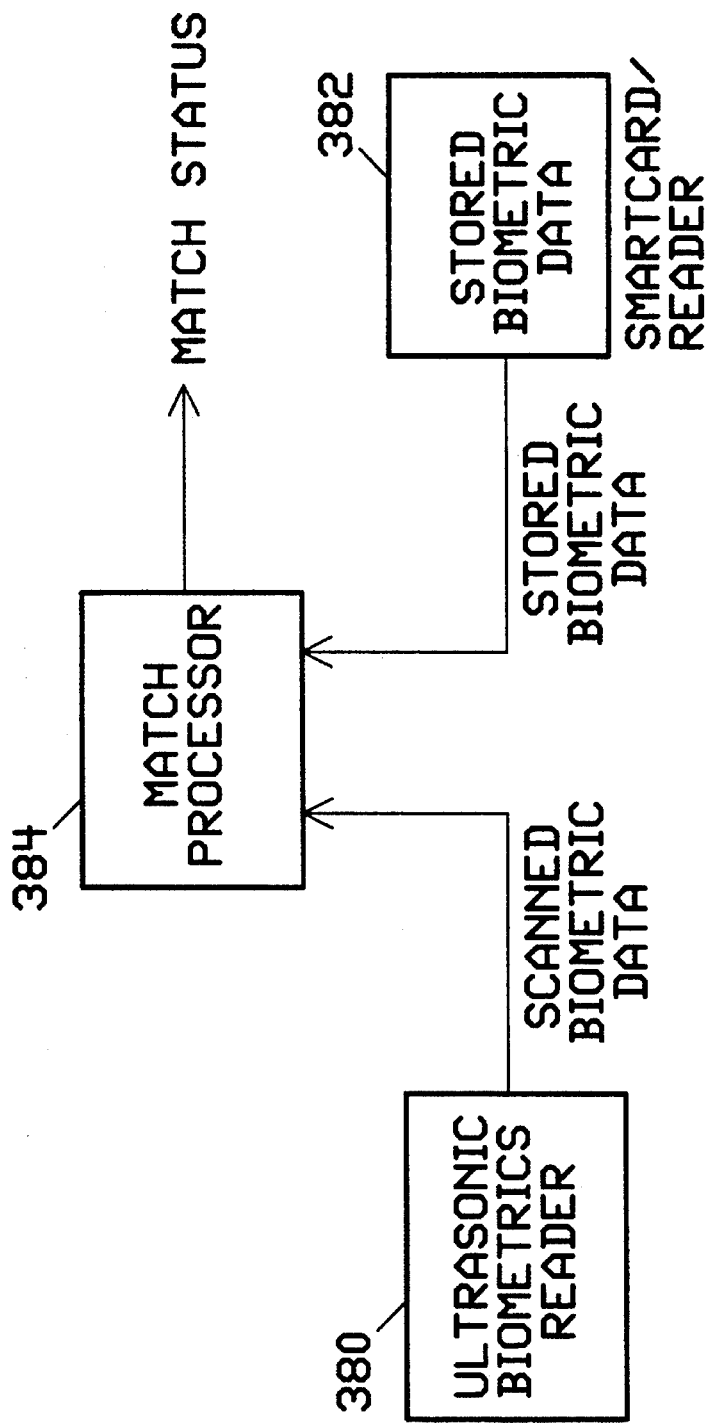
FIGS. 30 and 31 are block diagrams illustrating the use of the system and method of the present invention in a verification system.
Figure 31:
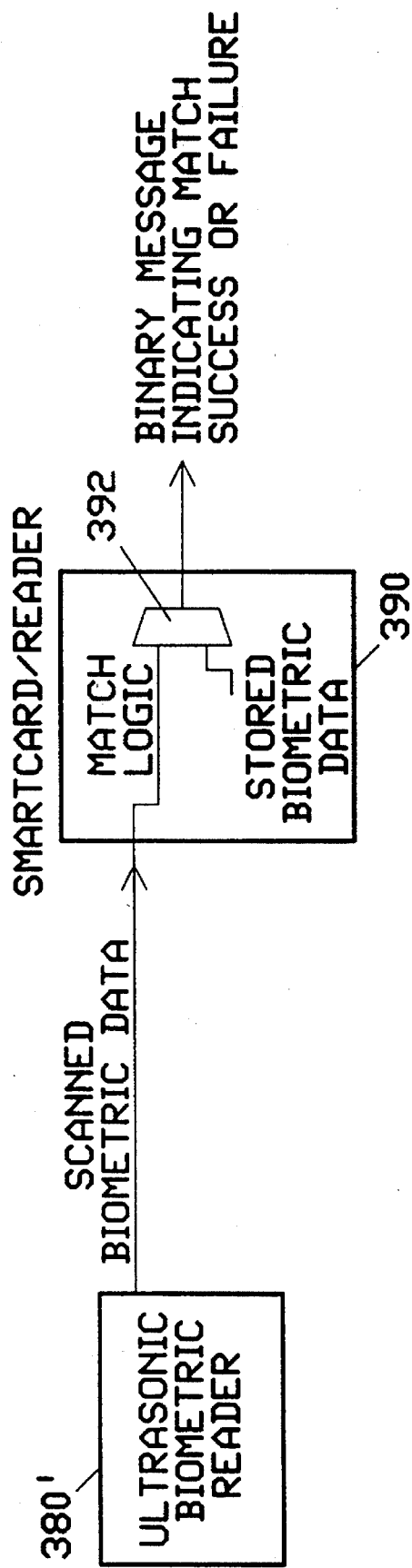

FIGS. 30 and 31 illustrate the system and method of the present invention configured in a verification system where a finger is scanned and compared to a single reference print to verify if the individual is who he claims to be. This type of system is much less complex in nature as compared to identification systems since it does not require the extensive searching that larger AFIS system must do, which require high speed processors, large databases, etc. One method of implementing such a system is using smartcards or any other type of portable data storage device such as a magostripe card, optical storage card, semiconductor storage card and the like. Smartcards are plastic cards similar in size to a standard credit card. The traditional mag-stripe found on the back of the card is either replaced or supplemented by an on board microprocessor. The microprocessor has built in memory which enables two options for overall system configuration. A first option is to simply encode the biometric data into the memory of the smartcard. A person wishing to have his identity verified places his finger on the ultrasonic reader and the finger is scanned. The data is then read out of the smartcard presented by the individual and a computer is used to compare the two images. This is illustrated in FIG. 30 wherein an ultrasonic biometric reader 380 comprises the system according to the present invention including probe assembly 12, signal processor 16, scan controller 14 and power supply 20. Data buffer 18 can be included if desired. A record member 382 in the form of the smartcard mentioned above has storage means containing a recorded biometric image, i.e. for storing a recorded fingerprint image. A processor means 384 has a first input for receiving output signals from the ultrasonic biometric reader and a second input for receiving a signal representation of the recorded image to determine if a match exists between the scanned and recorded images. Thus, in the arrangement of FIG. 30 the record member 382 and processor 384 are physically separate.

A second option is similar to the first option with the main difference being that the computer used to compare the two images is replaced by the processor of the smartcard. Thus, the smartcard not only contains the biometric data of the finger but is also responsible for comparing that data to the scanned data of the finger. This is illustrated in FIG. 31 wherein a smartcard or record member 390 has storage means containing a recorded biometric image and processor means 392 thereon having one input for receiving output signals from the ultrasonic biometric reader 380' and a second input for receiving a signal representation of the recorded image to determine if a match exists between the scanned and recorded images. Thus, in the arrangement of FIG. 31 the record member 390 and the processor 392 are physically integrated.

Figure 32:
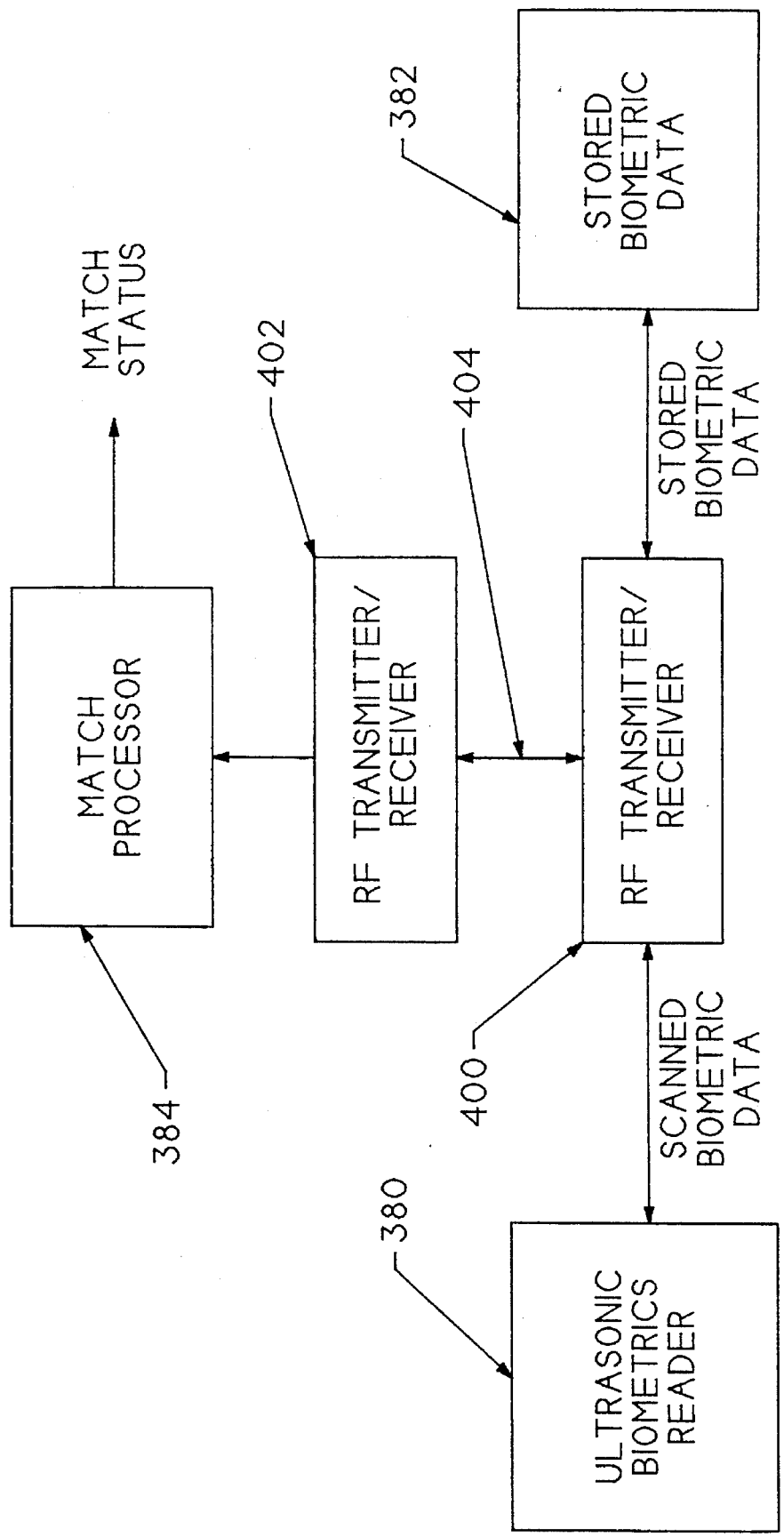
FIG. 32 is a block diagram illustrating a wireless version of the system of FIG. 30.

FIG. 32 illustrates an alternative arrangement wherein the hard-wired communication link between processor 384 and ultrasonic biometric reader 380 and record member 382 in the arrangement of FIG. 30 is replaced by a wireless communication link. The wireless communication link comprises an RF transmitter/receiver 400 connected to the outputs of biometric reader 380 and record member 382, an RF transmitter/receiver 402 connected to processor 384 and the transmission medium 404 therebetween. The RF communication link is bi-directional, allowing match results to be sent back to the reader subsystem. Other wireless communication links can be employed such as optical, ultrasonic and the like.

There are situations where the need exists for an identification/verification system to operate in remote areas with no AC power available. Normally under these conditions, only 12 VDC power exists and at limited current draw. As a result, there is a need to provide a low power version of the probe according to the present invention. The two largest power draws in the probe as previously described are the two motors 38 and 40 involved with controlling the scan motion. Removing these two motors reduces the overall power consumption of the probe by orders of magnitude.

Figure 33:
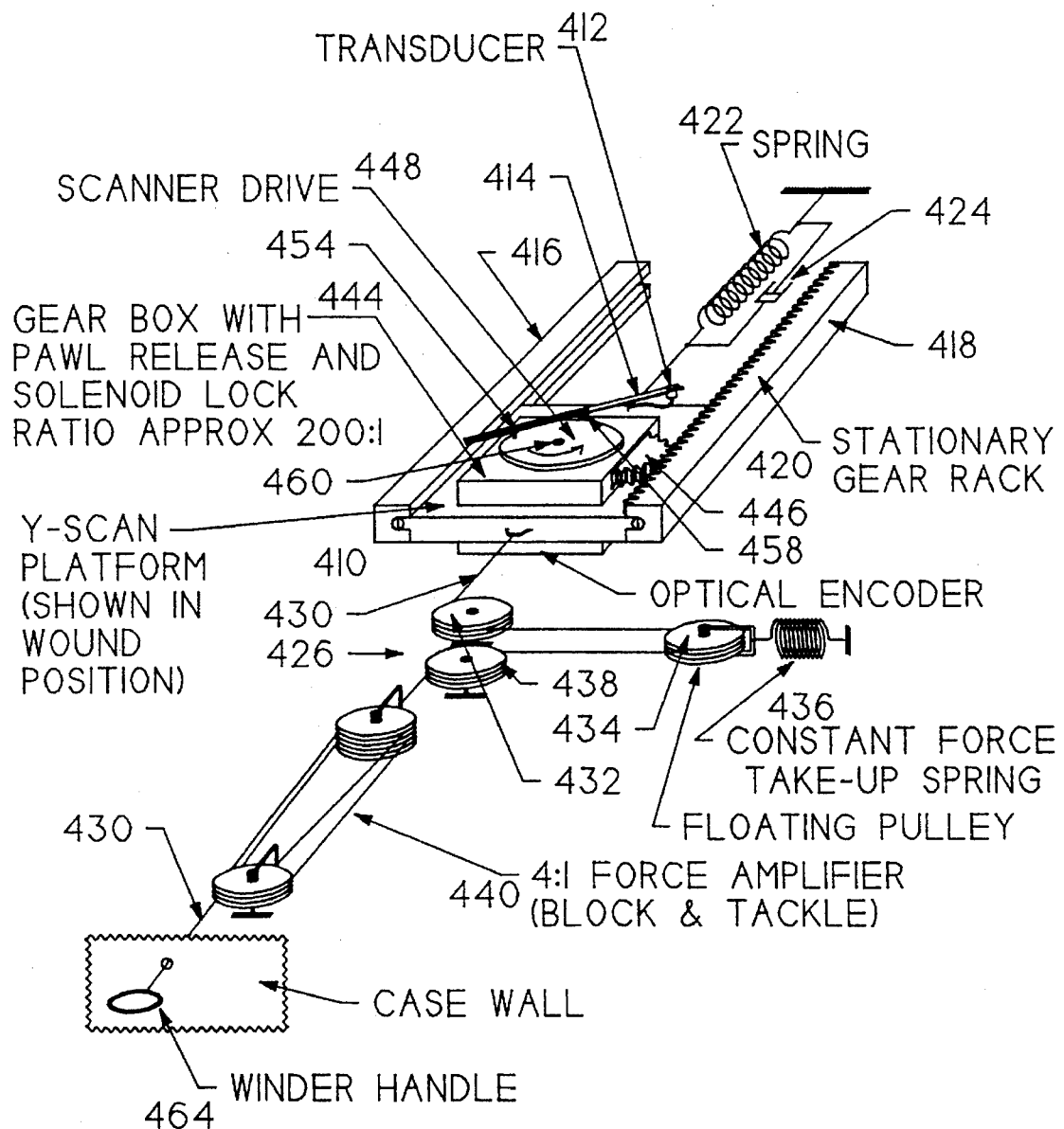
FIG. 33 is a developed perspective view, partly diagrammatic, of a spring-driven probe mechanism according to the present invention.

In accordance with this embodiment of the probe of the present invention as shown in FIG. 33, the operator is required to impart the necessary energy into the system to operate the scan motion. This is accomplished by stretching a spring prior to operation and having the spring power the mechanism for the duration of a single scan cycle. A platform 410 supports a transducer 412 carried on an arm 414, and platform 410 travels in two stationary guide tracks 416, 418 in the Y-direction of the scan. One of the guide tracks incorporates an elongated rack 420. A drive spring 422 for storing mechanical energy is attached to the rear of the platform; when elongated and released, the spring drives the platform 410 in the Y direction of the scan. The rate of release of energy from the spring 422 is controlled by a mechanical damper 424 operatively associated therewith to regulate the scanner motion.

A means generally designated 426 for storing energy in the drive spring 422, i.e. elongating the spring, is attached to the front of the moving platform 410. A tensioning cable 430 first passes over a fixed pulley 432 and then around a spring-driven take-up floating pulley 434 which in cooperation with a take-up spring 436 withdraws the pull cable into the instrument case in both the elongated and relaxed drive spring states. The cable then passes around another fixed pulley 438 and through a force amplifier 440 (block and tackle) with a 4:1 ratio that eases tensioning of the drive spring by exchanging force for distance.

A gearbox 444 is mounted on the top surface of the scanner platform 410. A gear 446 protruding from the side of the gear box engages the rack 420 and transmits most of the spring energy to an X-scan drive disk 448 as the platform 410 moves in the Y direction of the scan. The gear ratio of the box is such that the X-drive makes approximately 200 revolutions for 0.8 inches of platform travel (a gear ratio of 200:1).

The X-scan is performed by the pivoted arm 414 that carries the transducer 412 in 1 inch long arcs over the scan window. A pin 454 on the perimeter of the X-drive disk 448 engages a slot (not shown) in the scan arm 414 which is pivoted at 458. As the disk 448 rotates, its circular motion is translated to almost linear motion at the transducer end of the arm 414. Two X-scan lines are generated for each full revolution of the disk 448. An optical encoder (not shown) mounted on the underside of the Y-scan platform is driven by the X-drive disk shaft 460 protruding through the platform 410. Its signals are used to synchronize the X-scan. The beginning of the Y-scan is signaled by an optical sensor (not shown) mounted on the platform 410.

When a scan is to be performed, the user pulls the spring tensioning handle 464 to an extension of appropriate length until a visual indicator (not shown) signals full extension. The operator then releases the handle 464 and places his finger on the scan area. Shortly thereafter, a solenoid (not shown) unlocks the gear box 444 and starts the scan.

Thus, the arrangement of cable 430, pulleys 432, 434 and 438, take-up spring 436 and block and tackle 440 comprises motive means operatively coupled to supporting means 410 and to energy storage means 426 for transferring stored energy to supporting means 410 in a controlled manner and with it transducer means 412 along a linear path. Rack 420, gear 446, disk 448, pin 454 and the slot in arm 414 comprise motion conversion means drivenly coupled to the above-mentioned motive means and drivingly coupled to the transducer means 412 for moving the transducer means along a path cross-wise relative to the linear path in response to operation of the motive means. The cross-wise path is an arcuate path and the transducer 412 is moved back and forth along the arcuate path.

Transducer 412 can be identical to transducer 43 in the probe of FIG. 2, and transducer 412 is positioned closely adjacent the platen for supporting the finger in a manner similar to that of FIG. 2.

The probe architecture described hereinabove for scanning the finger performs a 2-dimensional scan geometry through strictly mechanical means. For example, in the arrangement of FIG. 2, a single line scan is performed by oscillating a single element fixed focus transducer back and forth using a DC brushless motor (or an equivalent limited angle torque motor). Once a single line has been scanned, a second motor is used to move the entire assembly along the second axis of motion, thereby sweeping out a second scan line. The high velocity oscillatory motion of the transducer is a consideration with respect to long term reliability. Furthermore, there is a certain amount of audible noise associate with this motion that may be a consideration in certain situations. Therefore, it is highly desirable to transition the predominantly mechanical scan motion of the probe into a solid-state version of the probe.

The first step in developing a new scan architecture would be to replace the single element, fixed focused transducer with a linear array of transducers. The linear array is a single line of properly sized, properly spaced transducer elements that can be used to image a single line of the finger. The array would contain enough elements at the proper spacing to avoid any motion in the axis parallel to the axis of the array. Once an entire line has been imaged, the linear array is then stepped in the second axis of motion in order to scan a second line of the finger. This would be accomplished by a linear actuator similar to actuator 40 in FIG. 2. This motion is repeated until the entire finger has been scanned. Implementing such an architecture has the advantage of eliminating the high speed oscillatory motion caused by the DC brushless motor. This alone is a great improvement with respect to overall reliability and user perception. Another advantage of the linear array is the ability to electronically focus the beam. It is well-known in the field that by delaying the excitation of the inner elements with respect to the outer elements, the shape of the sound beam will be as if it propagated through a focusing lens. Since this focusing can only take place in one axis, the size of the individual elements in the second axis must be small enough to provide the required resolution.

A second step is developing the solid state approach is the use of a 2-dimensional phased array. A 2-D phased array is a matrix of closely spaced elements of sufficient size and spacing to scan the entire finger without any type of mechanical motion whatsoever. This is accomplished by electronic beam steering. It is well-known in the field that the ultrasonic beam from a 2-dimensional phased array can be swept across a surface by purely electronic means. Each individual element is driven at a well-defined phase relationship to its neighboring elements. By doing such, the output is deflected off axis to a predictable point in space. A second advantage is the ability to electronically focus as described previously for the linear array. However, in this case, focusing can take place in both axes to provide a symmetrical spot size.

Figure 34:
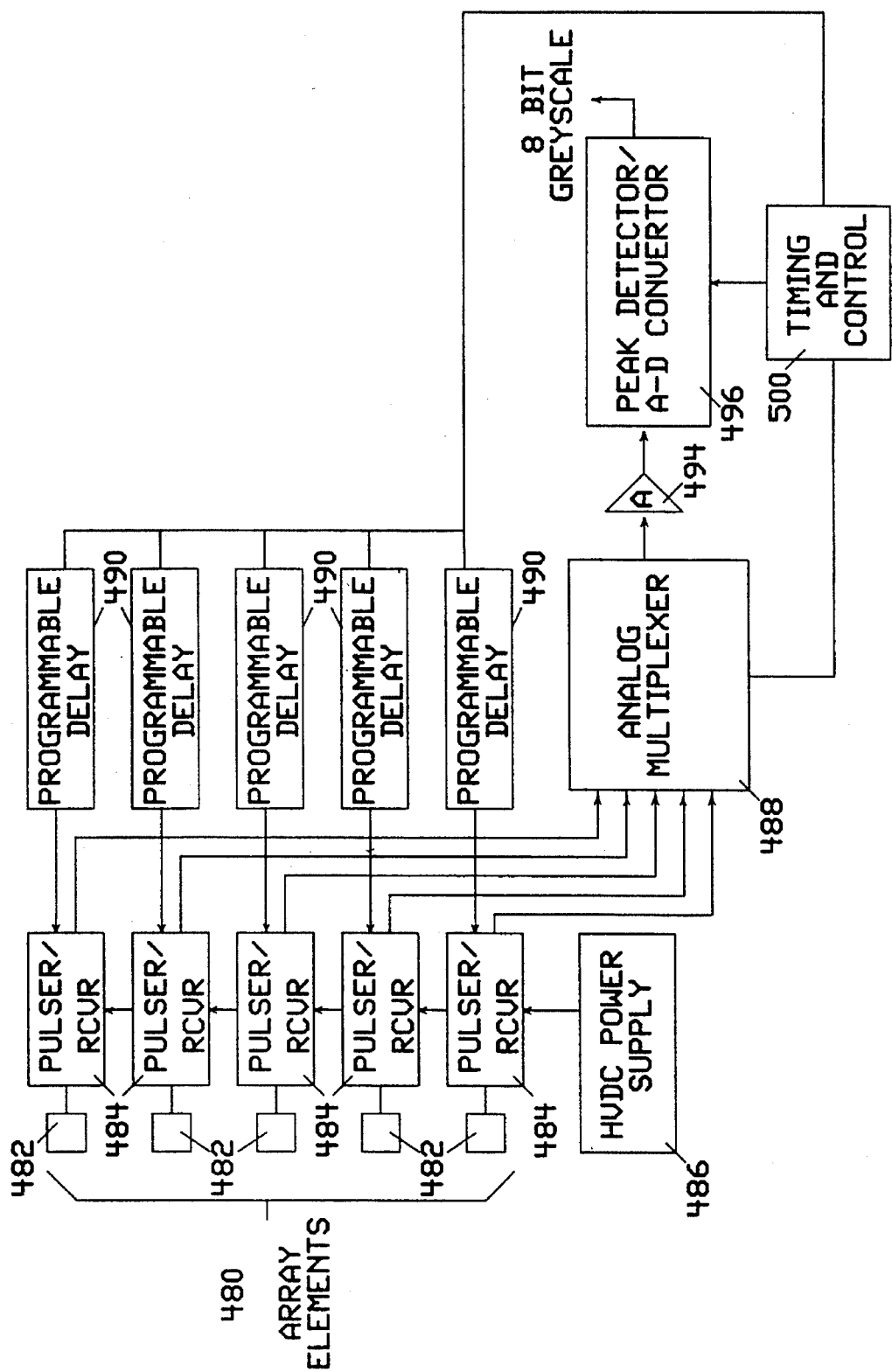
FIG. 34 is a block diagram of a solid state probe architecture according to the present invention.

The foregoing is illustrated in FIG. 34 wherein there is shown an array 480 of closely-spaced transducer elements 482. Array 480 is representative of either a linear array or a two-dimensional phased array. The tissue being scanned, i.e. a finger, is supported by suitable means in scanning relation to array 480 such as platen 30 in the probe of FIG. 2. A pulser/receiver component 484 is provided for and connected to each transducer element 482. The components are powered by a high voltage d.c. power supply 486. Each of the pulser/receiver components 484 is connected to an analog multiplexer 488. There is also provided a corresponding plurality of digital programmable delay components 490, one for and each connected to a corresponding one of the pulser/receiver components 484. The output of the analog multiplexer 488 is coupled through an amplifier 494 to a peak detector/analog-digital converter circuit 496, the output of which is an 8-bit greyscale information signal. A timing and control circuit 500 is connected to multiplexer 488 and to the programmable delay components 490.

In transmit mode, each element 482 of the array 480 is driven at a time which is slightly skewed from the surrounding elements. By differentially delaying (phase shifting) the pulses to the elements in a linear fashion across the array, the resulting transmitted ultrasonic beam can be electronically steered. By imposing a spherical time delay curvature across the array, the beam can be made to converge and focus at a desired depth. Combining these two approaches gives both beam sweeping and beam focusing. The details of these techniques are well-known and often practiced by the medical community for medical ultrasound scanners.

In receive mode, the return echo from each pulser/receiver 484 is sent to the analog multiplexer 488. The array elements are read in a fashion similar to how they are transmitted, each skewed in time with respect to its neighbor. The high-speed analog multiplexer 488 is sequenced to read each of the array elements at the appropriate time. The output of the multiplexer 488 is further amplified and peak detected. The results of the peak detector 496 for each cell is then summed to provide a final 8-bit value.

The implementation of both the analog multiplexer 488 and programmable delay lines 490 is well-known in the industry. Typically, the programmable delay lines are achieved using digital counter IC's. A unique count is loaded into each IC and downcounted to zero to produce a delay. Typical IC's used for such a device could be 74HC161, 74HC163, 74HC191, 74HC193, and others.

The analog multiplexer 488 is also implemented using readily available IC's. Multiple IC's are usually required to provide enough analog inputs. A typical analog multiplexer that could be used is the ADG409 by Analog Devices, Norwood, Mass.

The foregoing transducer array approach, particularly the two dimensional phased array approach, can be employed in an arrangement wherein the finger is rolled side-to-side on a flat platen so as to scan the finger from one edge of the fingernail to the other edge of the fingernail. Alternatively, a curved platen shaped like platen 320 in FIG. 27 can be provided to receive the finger in a stationary manner. A curved array of transducer elements can be provided in the one direction, i.e. along an arcuate path, and means provided to move the array along the longitudinal axis of the platen. Alternatively, a two dimensional phased array of transducer elements can be provided over the entire surface of the curved platen.

It is therefore apparent that the present invention accomplishes its intended objects. The ultrasonic scanning and imaging method and apparatus of the present invention enable scanning to be performed at an extremely fast rate and provide very high resolution images. While embodiments of the present invention have been described in detail, that is done for purposes of illustration, not limitation.

What is claimed is:

1. A probe for an ultrasonic imaging system for providing an output ultrasonic beam to scan human or animal tissue having a surface, said probe comprising:
   a) means for defining said surface in a manner rigidly supporting said human or animal tissue for imaging the same over the area of an image plane;
   b) transducer means for providing an output ultrasonic beam; and
   c) means for positioning said transducer means closely adjacent said supporting means in a manner directing said ultrasonic beam on said surface in a direction always substantially perpendicular to said image plane and so that the size of said beam at its focal point is as small as possible to maximize the resolution of said system in a plane substantially perpendicular to the direction of said beam.

2. A probe according to claim 1, wherein said means for defining said surface comprises platen means of a material having an acoustic impedance substantially matching the acoustic impedance of the tissue being imaged.

3. A probe according to claim 1, wherein said means for defining said surface comprises platen means in the form of a body of material having an acoustic impedance substantially matching the acoustic impedance of the tissue being imaged and having sufficient mechanical strength to support the tissue without deflection or deformation, said body being provided with a coating thereon of material which improves mechanical coupling of said body to the tissue being imaged while maintaining the matching of acoustic impedance.

4. A probe according to claim 1, wherein said positioning means comprises:
   a) first means for moving said transducer means to direct said beam along said surface in a first direction;
   b) second means for moving said transducer means to direct said beam along said surface in a second direction; and
   c) said first and second directions being along said image plane.

5. A probe according to claim 4, wherein said first means comprises motor means for oscillating said transducer means in an arcuate path along said surface.

6. A probe according to claim 5, wherein said second means comprises motive means for moving said transducer means in a linear path along said surface.

7. A probe according to claim 6, wherein said motive means includes means for guiding said transducer means along said linear path coinciding with a radius of said arcuate path.

8. A probe according to claim 5, further including encoder means operatively connected to said motor means for providing information on the amount of angular rotation provided by said motor means.

9. A probe for an ultrasonic imaging system for providing an output ultrasonic beam to scan human or animal tissue having a surface, said probe comprising:
   a) means for defining said surface in a manner rigidly supporting said human or animal tissue for imaging the same over the area of an image plane;
   b) transducer means for providing an output ultrasonic beam in a direction always substantially perpendicular to said image plane;
   c) motor means having an output shaft for providing oscillatory output motion;
   d) means for coupling said output shaft to said transducer means so that in response to oscillation of said shaft said output ultrasonic beam is directed in an arcuate path along said surface in a direction substantially parallel to said image plane; and
   e) motive means for moving said transducer means in a manner such that said output ultrasonic beam is directed in a linear path along said surface in a direction substantially parallel to said image plane and in a radial direction relative to said arcuate path.

10. A probe according to claim 9, further including encoder means operatively coupled to said output shaft of said motor means for providing information on the amount of angular rotation provided by said motor means.

11. A probe according to claim 10, wherein said encoder means comprises optical encoder means for providing an output pulse for a given amount of angular rotation of said output shaft of said motor means.

12. A probe according to claim 11, wherein the angular resolution of said optical encoder means and a dimension of said coupling means are related in a manner such that an output pulse from said optical encoder means corresponds to a given amount of movement of said ultrasonic beam along said arcuate path independent of the velocity of said motor means.

13. A probe according to claim 9, further including position sensor means operatively associated with said means for moving said transducer means to direct said beam in said linear path for establishing a starting and reference position.

14. A probe for an ultrasonic imaging system for providing an output ultrasonic beam to scan human or animal tissue having a surface, said probe comprising:
   a) means for defining said surface in a manner supporting said human or animal tissue for imaging the same;
   b) transducer means for providing an output ultrasonic beam;
   c) means for positioning said transducer means closely adjacent said supporting means in a manner directing said ultrasonic beam on said surface and so that the size of said beam at its focal point is as small as possible to maximize the resolution of said system, said positioning means comprising first means for moving said transducer means to direct said beam along said surface in a first direction and second means for moving said transducer means to direct said beam along said surface in a second direction, said first means comprising motor means for oscillating said transducer means in an arcuate path along said surface;
   d) means for providing a liquid-filled region between said transducer means and said surface; and
   e) means for providing a rotational and oscillatory flexible liquid impervious seal between said motor means and said means providing said liquid-filled region.

15. A probe for an ultrasonic imaging system for providing an output ultrasonic beam to scan human or animal tissue having a surface, said probe comprising:
   a) means for defining said surface in a manner supporting said human or animal tissue for imaging the same;
   b) transducer means for providing an output ultrasonic beam;
   c) motor means having an output shaft for providing oscillatory output motion;
   d) means for coupling said output shaft to said transducer means so that in response to oscillation of said shaft said output ultrasonic beam is directed in an arcuate path along said surface;
   e) means for moving said transducer means in a manner such that said output ultrasonic beam is directed in a linear path along said surface and in a radial direction relative to said arcuate path;
   f) means for providing a liquid-filled region between said transducer means and said surface; and
   g) means for providing a rotational and oscillatory flexible liquid impervious seal between said output shaft of said motor means and said means providing said liquid-filled region in a manner causing minimal drag on said motor means.

16. A probe according to claim 15, wherein said means providing said liquid-filled region includes a wall having an aperture through which said output shaft extends and wherein said seal providing means is attached to said wall and to said output shaft.

17. A probe according to claim 16, wherein said seal providing means is in the form of a bladder having openings at opposite ends and positively attached adjacent said ends to said shaft and to said wall.

18. A probe according to claim 17, wherein said bladder is stretchable and attached in a manner allowing it to be loose between the attachment locations to provide limited rotary oscillatory motion with minimal drag on said motor means.

19. A probe according to claim 17, wherein said bladder is of relatively thin latex material and is adhesively attached to said shaft and said wall.

20. A method for ultrasonic imaging of human or animal tissue having a surface comprising the steps of:
   a) defining said surface in a manner supporting said human or animal tissue for imaging the same;
   b) providing an ultrasonic energy beam;
   c) directing said ultrasonic beam in an arcuate path along said surface;
   d) directing said ultrasonic beam in a linear path along said surface and in a radial direction relative to said arcuate path;
   e) linearizing the scanned image resulting from said step of directing said ultrasonic beam in an arcuate path; and
   f) said step of linearizing comprising storing the data as scanned wherein each row of stored data points represents an arc of the image and calculating the new position for each pixel in the image band on the dimensions of the scanned arc.

21. A method for ultrasonic imaging of human or animal tissue having a surface comprising the steps of:
   a) defining said surface in a manner rigidly supporting said human or animal tissue for imaging the same over the area of an image plane;

b) providing an ultrasonic energy beam in a direction always substantially perpendicular to said image plane;

c) directing said ultrasonic beam in an arcuate path along said surface in a Direction substantially parallel to said image plane;

d) directing said ultrasonic beam in a linear path along said surface in a direction substantially parallel to said image plane and in a radial direction relative to said arcuate path; and e) providing timing for the date points resulting from scanning the surface along said arcuate path.

22. A method according to claim 21, wherein said timing is provided by energizing said ultrasonic beam at regular intervals along said arcuate path.

23. An ultrasonic imaging system for imaging human or animal tissue having a surface comprising:

a) probe means including means for defining said surface in a manner rigidly supporting said human or animal tissue for imaging the same, transducer means positioned closely adjacent said supporting means for providing an output ultrasonic beam directed on said surface so that the size of said beam at its focal point is as small as possible to maximize the resolution of said system and motive means for moving said transducer means in two directions so as to provide a two dimensional scan of said surface by said ultrasonic beam;

b) scan controller means operatively connected to said probe means for controlling said motive means to provide said scan of said surface;

c) signal processor means operatively connected to said probe means for receiving signals produced in response to said scan of said surface and for processing said signals.

24. A system according to claim 23, further including data buffer means connected to said signal processor means for storing data resulting from said processing of said signals.

25. A system according to claim 24, further including processor means operatively connected to said data buffer means so that said imaging system can scan said surface at a relatively fast rate independent of the rate at which said processor means reads data from said data buffer means.

26. A system according to claim 23, wherein said scan controller means comprises:

a) means for providing command signals for controlling said motive means;

b) means for receiving positional information from said motive means; and c) means for providing timing and control signals for said system.

27. A probe for an ultrasonic imaging system for providing an output ultrasonic beam to scan human or animal tissue having a surface, said probe comprising:

a) means for defining said surface in a manner supporting said human or animal tissue for imaging the same;

b) transducer means for providing an output ultrasonic beam;

c) means for supporting said transducer means;

d) means for storing mechanical energy;

e) motive means operatively coupled to said supporting means and to said energy storing means for transferring stored energy to said supporting means in a controlled manner to move said supporting means and with it said transducer means along a linear path; and f) motion conversion means drivenly coupled to said motive means and drivingly coupled to said transducer means for moving said transducer means along a path cross-wise relative to said linear path in response to operation of said motive means.

28. A probe according to claim 27, wherein said motion conversion means includes means for converting linear motion from said motive means into oscillatory motion of said transducer means along an arcuate path extending cross-wise relative to said linear path.

29. A probe for an ultrasonic imaging system for providing an output ultrasonic beam to scan human or animal tissue having a surface, said probe comprising:

a) means for defining said surface in a manner supporting said human or animal tissue for imaging the same;

b) transducer means for providing an output ultrasonic beam;

c) means for supporting said transducer means;

d) means for storing mechanical energy;

e) motive means operatively coupled to said supporting means and to said energy storing means for transferring stored energy to said supporting means in a controlled manner to move said supporting means and with it said transducer means along a linear path;

f) motion conversion means drivenly coupled to said motive means and drivingly coupled to said transducer means for moving said transducer means along a path cross-wise relative to said linear path in response to operation of said motive means;

g) said means for storing mechanical energy comprising spring means and tensioning means operatively coupled to said spring means for extending said spring means to store energy therein; and h) said motive means comprising damper means operatively associated with said spring means for controlling the release of energy stored in said spring means and force conversion means for converting the release of stored energy in said spring means to linear motion of said supporting means.

30. A probe for an ultrasonic imaging system for providing an output ultrasonic beam to scan human or animal tissue having a surface, said probe comprising:

a) means for defining said surface in a manner supporting said human or animal tissue for imaging the same;

b) transducer means for providing an output ultrasonic beam;

c) means for supporting said transducer means;

d) means for storing mechanical energy;

e) motive means operatively coupled to said supporting means and to said energy storing means for transferring stored energy to said supporting means in a controlled manner to move said supporting means and with it said transducer means along a linear path;

f) motion conversion means drivenly coupled to said motive means and drivingly coupled to said transducer means for moving said transducer means along a path cross-wise relative to said linear path in response to operation of said motive means;

g) said motion conversion means comprising rack means fixed in relation to said supporting means and pinion means carried by said supporting means so that upon linear movement of said supporting means said pinion is rotated.

31. A probe according to claim 30, further including means for converting rotary motion of said pinion means into oscillatory motion of said transducer means along an arcuate path extending cross-wise relative to said linear path of said supporting means.

32. A biometric verification system comprising:
   a) an ultrasonic imaging system for imaging human or animal tissue and providing output signals representing a scanned biometric image;
   b) a record member having storage means containing a recorded biometric image;
   c) processor means having a first input for receiving output signals from said ultrasonic imaging system and a second input for receiving a signal representation of said recorded image to determine if a match exists between said scanned and recorded images; and
   d) means for providing a wireless communication link between said processor means and said ultrasonic imaging system and said record member.

33. An ultrasonic imaging method for imaging human or animal tissue having a surface comprising:
   a) providing a plurality of ultrasonic transducer elements arranged in an array and each providing an output ultrasonic beam;
   b) supporting said human or animal tissue so that the surface thereof can be scanned by the ultrasonic beams from said array of transducers;
   c) arranging said transducer elements in a linear array for scanning said surface in a first direction;
   d) moving said array of transducer elements in a second direction substantially perpendicular to said first direction;
   e) energizing said transducer elements;
   f) receiving signals produced in response to scanning of the surface;
   g) imposing a spherical time delay curvature across the array during energizing of the transducer elements so that the ultrasonic beams can be converged and focused.

34. An ultrasonic imaging method for imaging human or animal tissue having a surface comprising:
   a) providing a plurality of ultrasonic transducer elements arranged in an array and each providing an output ultrasonic beam;
   b) supporting said human or animal tissue so that the surface thereof can be scanned by the ultrasonic beams from said array of transducers;
   c) arranging said transducer elements in a linear array for scanning said surface in first direction;
   d) moving said array of transducer elements in a second direction substantially perpendicular to said first direction;
   e) energizing said transducer elements;
   f) differentially delaying the energizing of said transducer elements in an appropriate fashion across the array;
   g) imposing a spherical time delay curvature across the array during energizing of the transducer elements;
   h) so that the ultrasonic beams from said transducer elements are swept and focused during scanning of the surface; and
   i) receiving signals produced in response to scanning of the surface.

35. An ultrasonic imaging method for imaging human or animal tissue having a surface comprising:
   a) providing a plurality of ultrasonic transducer elements arranged in an array and each providing an output ultrasonic beam;
   b) arranging said array of transducer elements in a two dimensional array extending over the area of the surface to be scanned;
   c) supporting said human or animal tissue so that the surface thereof can be scanned by the ultrasonic beams from said array of transducers;
   d) energizing said transducer elements;
   e) imposing a spherical time delay curvature across the array during energizing of the transducer elements so that the ultrasonic beams can be converged and focused; and
   i) receiving signals produced in response to scanning of the surface.

36. An ultrasonic imaging method for imaging human or animal tissue having a surface comprising:
   a) providing a plurality of ultrasonic transducer elements arranged in an array and each providing an output ultrasonic beam;
   b) arranging said array of transducer elements in a two dimensional array extending over the area of the surface to be scanned;
   c) supporting said human or animal tissue so that the surface thereof can be scanned by the ultrasonic beams from said array of transducers;
   d) energizing said transducer elements;
   e) differentially delaying the energizing of said transducer elements in an appropriate fashion across the array;
   f) imposing a spherical time delay curvature across the array during energizing of the transducer elements;
   g) so that the ultrasonic beams from said transducer elements are swept and focused during scanning of the surface; and
   h) receiving signals produced in response to scanning of the surface.

37. An ultrasonic imaging method for imaging human or animal tissue having a surface comprising:
   a) providing a plurality of ultrasonic transducer elements arranged in an array and each providing an output ultrasonic beam;
   b) supporting said human or animal tissue so that the surface thereof can be scanned by the ultrasonic beams from said array of transducers;
   c) said step of supporting said human or animal tissue comprising rolling the finger of a subject on a flat platen from side-to-side so that the finger is scanned from one edge of the fingernail to the other edge of the fingernail;
   d) energizing said transducer elements; and
   e) receiving signals produced in response to scanning of the surface.

38. An ultrasonic imaging method for imaging human or animal tissue having a surface comprising:
   a) providing a plurality of ultrasonic transducer elements arranged in an array and each providing an output ultrasonic beam;
   b) supporting said human or animal tissue so that the surface thereof can be scanned by the ultrasonic beams from said array of transducers;
   c) energizing said transducer elements;
   d) receiving signals produced in response to scanning of the surface; and
   e) said step of supporting said human or animal tissue comprising placing the finger of a subject in a curved platen wherein said array of transducer elements is arranged in one direction along the curvature of the platen and moved in another direction along the longitudinal axis of the platen so that the finger is scanned from one edge of the fingernail to the other edge of the fingernail.

39. An ultrasonic imaging method for imaging human or animal tissue having a surface comprising:
   a) providing a plurality of ultrasonic transducer elements arranged in an array and each providing an output ultrasonic beam;
   b) supporting said human or animal tissue so that the surface thereof can be scanned by the ultrasonic beams from said array of transducers;
   c) energizing said transducer elements;
   d) receiving signals produced in response to scanning of the surface; and
   e) said step of supporting said human or animal tissue comprising placing the finger of a subject in a curved platen wherein said array of transducer elements is arranged in two dimensions over the surface of the platen so that the finger is scanned from one edge of the fingernail to the other edge of the fingernail.

40. A probe for an ultrasonic imaging system for providing an output ultrasonic beam to scan human or animal tissue having a surface, said probe comprising:
   a) means for defining said surface in a manner rigidly supporting said human or animal tissue for imaging the same;
   b) transducer means for providing an output ultrasonic beam;
   c) means for providing a liquid-filled region between said transducer means and said surface; and
   d) means for positioning said transducer means in said liquid-filed region and closely adjacent said supporting means in a manner directing said ultrasonic beam on said surface and so that the size of said beam at its focal point is as small as possible to maximize the resolution of said system.

41. A probe for an ultrasonic imaging system for providing an output ultrasonic beam to scan human or animal tissue having a surface, said probe comprising:
   a) means for defining said surface in a manner supporting said human or animal tissue for imaging the same;
   b) transducer means for providing an output ultrasonic beam;
   c) means for positioning said transducer means closely adjacent said supporting means in a manner directing said ultrasonic beam on said surface and so that the size of said beam at its focal point is as small as possible to maximize the resolution of said system;
   d) said means for defining said surface comprising platen means in the form of a body of material having an acoustic impedance substantially matching the acoustic impedance of the tissue being imaged and having sufficient mechanical strength to support the tissue without deflection or deformation, said body being provided with a coating thereon of material on the surface of the body which contacts the tissue which improves mechanical coupling of said body to the tissue being imaged while maintaining the matching of acoustic impedance.

42. A probe for an ultrasonic imaging system for providing an output ultrasonic beam to scan human or animal tissue having a surface, said probe comprising:
   a) means for defining said surface in a manner supporting said human or animal tissue for imaging the same;
   b) transducer means for providing an output ultrasonic beam;
   c) means for positioning said transducer means closely adjacent said supporting means in a manner directing said ultrasonic beam on said surface and so that the size of said beam at its focal point is as small as possible to maximize the resolution of said system;
   d) said positioning means including motor means having an output shaft for providing oscillatory motion to move said transducer means for scanning said surface;
   e) means for providing a liquid-filled region between said transducer means and said surface; and
   f) means for providing an rotary oscillatory flexible liquid impervious seal between said output shaft of said motor means and said means providing said liquid-filled region in a manner causing minimal drag on said motor means.

43. A probe according to claim 42, wherein said means providing said liquid-filled region includes a wall having an aperture through which said output shaft extends and wherein said seal providing means is attached to said wall and to said output shaft.

44. A probe according to claim 43, wherein said seal providing means is in the form of a bladder having openings at opposite ends and positively attached adjacent said ends to said shaft and to said wall.

45. A probe according to claim 44, wherein said bladder is stretchable and attached in a manner allowing it to be loose between the attachment locations to provide limited rotary oscillatory motion with minimal drag on said motor means.

46. A probe according to claim 44, wherein said bladder is of relatively thin latex material and is adhesively attached to said shaft and said wall.

47. A method for ultrasonic imaging of human or animal tissue having a surface comprising the steps of:
   a) utilizing an ultrasonic beam to perform an ultrasonic scan in three dimensions over a fixed area of the surface to provide a return signal; and
   b) applying a high resolution range gate to said return signal to allow propagation of only that portion of the return signal from the immediate underside of the epidermis of the tissue;
   c) so that an image is generated in a plane substantially perpendicular to the direction of propagation of the ultrasonic beam.

48. A method according to claim 47, wherein said step of performing an ultrasonic scan is with ultrasonic energy having a frequency of about 30 MHz.

49. A method according to claim 47, wherein said return signal is processed to provide a peak signal and wherein said high resolution range gate is applied to said peak signal.

50. A method for ultrasonic imaging of human or animal tissue having a surface comprising the steps of:
   a) utilizing an ultrasonic beam to perform an ultrasonic scan in three dimensions over a fixed area of the surface to provide a return signal; and
   b) applying a high resolution range gate to said return signal to allow propagation of only that portion of the return signal from a predetermined location beneath the surface of the tissue;
   c) so that an image is generated in a plane substantially perpendicular to the direction of propagation of the ultrasonic beam.

51. A method according to claim 50, wherein said step of performing an ultrasonic scan is with ultrasonic energy having a frequency of about 15 MHz.

52. A method according to claim 50, wherein an ultrasonic scan is performed in a manner such that only the scatter return is received for imaging.

53. A method for ultrasonic imaging of human or animal tissue having a surface comprising the steps of:
   a) defining said surface in a manner rigidly supporting said human or animal tissue for imaging the same over the area of an image plane;
   b) providing an ultrasonic energy beam in a direction always substantially perpendicular to said image plane;
   c) directing said ultrasonic beam in an arcuate path along said surface in a direction substantially parallel to said image plane; and
   d) directing said ultrasonic beam in a linear path along said surface in a direction substantially parallel to said image plane and in a radial direction relative to said arcuate path.

54. A method according to claim 53 further including linearizing the scanned image resulting from said step of directing said ultrasonic beam in an arcuate path.

55. A method according to claim 54, wherein said step of linearizing comprises altering the position of each pixel in the imaging to compensate for the arc motion of the ultrasonic beam.

56. A method according to claim 53, wherein said return signal is processed to provide a peak signal and wherein said high resolution range gate is applied to said peak signal.

57. A probe for an ultrasonic imaging system for providing an output ultrasonic beam for scanning the finger of a subject, said probe comprising:
   a) curved supporting means for rigidly supporting the finger for scanning from one edge of the fingernail to the other edge thereof, said supporting means having a longitudinal axis and supporting the finger with said longitudinal axis being substantially parallel to the longitudinal axis of the finger;
   b) transducer means for providing an output ultrasonic beam, said transducer means comprising a plurality of transducers in spaced-apart relation in a direction along the longitudinal axis of said supporting means;
   c) means for moving said transducer means along a first path substantially radially about said longitudinal axis of said supporting means so that said ultrasonic beam is directed along a path from one edge of the fingernail to the other; and
   d) means for moving said transducer means along a second path substantially parallel to the longitudinal axis of said supporting means so that said ultrasonic beam is directed along a path substantially parallel to the longitudinal axis of the finger.

58. A probe for an ultrasonic imaging system for providing an ultrasonic beam to scan human or animal tissue having a surface, said probe comprising:
   a) means for defining said surface in a manner supporting said human or animal tissue for imaging the same;
   b) a plurality of transducer means, each providing an output ultrasonic beam;
   c) means for supporting said transducer means in spaced relation along a transducer path;
   d) first motive means operatively connected to said supporting means for moving said transducer means along a first scanning path along said surface so that said transducer path is in registry with said first scanning path and each of the ultrasonic beams from said plurality of transducer means is directed along a portion of said first scanning path in a manner such that the sum of the portions scanned equals the total length of said scanning path; and
   e) second motive means for moving said plurality of transducer means along a second scanning path along said surface.

59. A probe according to claim 58, wherein said plurality of transducer means are equally spaced along said transducer path.

60. A probe according to claim 58, wherein the portions of said first scanning path along which said ultrasonic beams are directed are equal and in sum equal the total length of said first scanning path.

61. A probe according to claim 58, wherein said transducer path and said first scanning path are arcuate and have a common radius.

62. A probe according to claim 61, wherein said first motive means provides oscillatory motion about an axis located at the common radius of said transducer path and said first scanning path.

63. A probe according to claim 61, wherein said second motive means provides linear motion in a radial direction relative said arcuate paths.

64. A biometric identification system comprising:
   a) an ultrasonic imaging system for imaging human or animal tissue having a surface and comprising probe means including means for defining said surface in a manner supporting said human or animal tissue for imaging the same, transducer means positioned closely adjacent said supporting means for providing an output ultrasonic beam directed on said surface so that the size of said beam at its focal point is as small as possible to maximize the resolution of said system and motive means for moving said transducer means in two directions so as to provide a two dimensional scan of said surface by said ultrasonic beam, said imaging system further comprising scan controller means operatively connected to said probe means for controlling said motive means to provide said scan of said surface and signal processor means operatively connected to said probe means for receiving signals produced in response to said scan of said surface and for processing said signals to provide an output;
   b) means for storing a database of previously stored images; and
   c) system processor means having inputs coupled to said database storage means and to the output of said processor means for comparing a scanned image from said ultrasonic imaging system to the previously stored images in said database storage means to determine if a match exists.

65. A system according to claim 64, further including data buffer means connected between the output of said signal processor means and said system processor means so that said ultrasonic imaging system can scan said surface at a relatively fast rate independent of the rate at which said system processor means reads data from said data buffer means.

66. A system according to claim 64, in combination with another ultrasonic imaging system, database storage means and system processor means together with local area network means for connecting said first-named system processor means and said another system processor means together.

67. A system according to claim 64, further including means for providing a wireless communication link between said ultrasonic imaging system and said system processor means.

68. A biometric verification system comprising:
   a) an ultrasonic imaging system for imaging human or animal tissue and providing output signals representing a scanned biometric image;
   b) a record member physically separate from said imaging system and having storage means containing a recorded biometric image, said record member being sufficiently small in size and light in weight so as to be portable and said record member being in a form so that it can be carried on a person;
   c) processor means having a first input for receiving output signals from said ultrasonic imaging system and a second input for receiving a signal representation of said recorded image from said record member to determine if a match exists between said scanned and recorded images.

69. A biometric verification system according to claim 68, wherein said record member and said processor means are physically separate.

70. A biometric verification system according to claim 68, wherein said record member and said processor means are physically integrated.

71. A biometric verification system according to claim 68, wherein said ultrasonic imaging system comprises:
   a) probe means including means for defining a surface in a manner supporting said human or animal tissue for imaging the same, transducer means positioned closely adjacent said supporting means for providing an output ultrasonic beam directed on said surface so that the size of said beam at its focal point is as small as possible to maximize the resolution of said system and motive means for moving said transducer means in two directions so as to provide a two dimensional scan of said surface by said ultrasonic beam;
   b) scan controller means operatively connected to said probe means for controlling said motive means to provide said scan of said surface; and
   c) signal processor means operatively connected to said probe means for receiving signals produced in response to said scan of said surface and for processing said signals to provide an output.

72. A probe for an ultrasonic imaging system for providing an output ultrasonic beam for scanning the finger of a subject, said probe comprising:
   a) curved supporting means for rigidly supporting the finger for scanning from one edge of the fingernail to the other edge thereof, said supporting means having a longitudinal axis and supporting the finger with said longitudinal axis being substantially parallel to the longitudinal axis of the finger;
   b) transducer means for providing an output ultrasonic beam;
   c) means for moving said transducer means along a first path substantially radially about said longitudinal axis of said supporting means so that said ultrasonic beam is directed along a path from one edge of the fingernail to the other; and
   d) means for moving said transducer means linearly along a second path substantially parallel to the longitudinal axis of said supporting means so that said ultrasonic beam is directed along a path substantially parallel to the longitudinal axis of the finger.

73. A probe according to claim 72, wherein said supporting means is substantially semicylindrical in cross-sectional shape and wherein said first path is an arcuate path having an arc length of about 180 degrees.

74. A probe according to claim 72, further including means for positioning said transducer means closely adjacent said supporting means in a manner directing said ultrasonic beam on the finger and so that the size of said beam at its focal point is as small as possible to maximize the resolution of said system.

75. A probe according to claim 72, wherein said supporting means has a curved surface adapted to contact the finger and has longitudinally extending edges approximately in registry with the edges of the fingernail.

76. An ultrasonic imaging system for imaging human or animal tissue having a surface comprising:
   a) transducer means comprising a plurality of transducer elements each providing an output ultrasonic beam, said transducer elements being arranged in an array;
   b) means for rigidly supporting said human or animal tissue so that the surface thereof can be scanned by the ultrasonic beams from said array of transducer elements; and
   c) means for energizing said transducer elements and for receiving signals produced in response to scanning of the surface.

77. A system according to claim 76, wherein said array of transducer elements comprises a linear array extending in a first direction relative to the surface and further including means for moving said array in a second direction substantially perpendicular to said first direction.

78. A system according to claim 76, wherein said array of transducer elements comprises a two dimensional array extending over the area of the surface to be scanned and further including means for electronically steering the ultrasonic beams from said array of transducer elements.

79. An ultrasonic imaging system for imaging human or animal tissue having a surface comprising:
   a) transducer means comprising a plurality of transducer elements each providing an output ultrasonic beam, said transducer elements being arranged in an array;
   b) means for rigidly supporting said human or animal tissue so that the surface thereof can be scanned by the ultrasonic beams from said array of transducer elements; and
   c) means for energizing said transducer elements and for receiving signals produced in response to scanning of the surface, said means for energizing and receiving comprising pulser/receiver means operatively connected to each of said transducer elements for energizing said transducer elements and for receiving return echo signals and multiplexer means operatively connected to said pulser/receiver means for reading signals received from each of said pulser/receiver means.

80. A system according to claim 79, further including peak detector means operatively connected to said multiplexer means for providing a signal containing image information.

81. An ultrasonic imaging system for imaging human or animal tissue having a surface comprising:
   a) transducer means comprising a plurality of transducer elements each providing an output ultrasonic beam, said transducer elements being arranged in a two dimensional array extending over the area of the surface to be scanned;

b) means for supporting said human or animal tissue so that the surface thereof can be scanned by the ultrasonic beams from said array of transducer elements; and c) means for energizing said transducer elements and for receiving signals produced in response to scanning of the surface, said means for energizing and receiving comprising a plurality of pulser/receiver means, one for each of said transducer elements, operatively connected to corresponding ones of said transducer elements, each of said pulser/receiver means energizing a corresponding one of said transducer elements and receiving return echo signals, and a plurality of programmable delay lines, one for each of said transducer elements, operatively connected to corresponding ones of said pulser/receiver means, said delay lines differentially delaying the energization of said transducer elements in a manner providing sweeping and steering of the ultrasonic beams from said transducer elements.

82. A system according to claim 81 further including:

a) multiplexer means operatively connected to said pulser/receiver means for reading signals received from each of said pulser/receiver means;

b) timing and control means operatively connected to said multiplexer means and to said programmable delay lines for providing timing and control signals to said multiplexer means and to said programmable delay lines; and c) peak detection means operatively connected to said multiplexer means for peak detecting the output of said multiplexer means to provide a signal containing image information.

83. An ultrasonic imaging method for imaging human or animal tissue having a surface comprising:

a) providing a plurality of ultrasonic transducer elements arranged in an array and each providing an output ultrasonic beam;

b) rigidly supporting said human or animal tissue so that the surface thereof can be scanned by the ultrasonic beams from said array of transducers; and c) energizing said transducer elements; and d) receiving signals produced in response to scanning of the surface.

84. A method according to claim 83, further including processing the received signals to provide image information.

85. A method according to claim 83, including:

a) arranging said transducer elements in a linear array for scanning said surface in first direction; and b) moving said array of transducer elements in a second direction substantially perpendicular to said first direction.

86. A method according to claim 85, further including differentially delaying the energizing of said transducer elements in an appropriate fashion across the array so that the ultrasonic beams from said transducers can be electronically steered.

87. A method according to claim 83 including arranging said array of transducer elements in a two dimensional array extending over the area of the surface to be scanned.

88. A method according to claim 87, further including differentially delaying the energizing of said transducer elements in an appropriate fashion across the array so that the ultrasonic beams from said transducers can be electrically steered.

89. A biometric identification system comprising:

a) an ultrasonic imaging system for imaging human or animal tissue having a surface and comprising probe means including means for defining said surface in a manner supporting said human or animal tissue for imaging the same, transducer means positioned closely adjacent said supporting means for providing an output ultrasonic beam directed on said surface so that the size of said beam at its focal point is as small as possible to maximize the resolution of said system, said imaging system further comprising control means operatively connected to said probe means for controlling scanning of said surface by said transducer means and signal processor means operatively connected to said probe means for receiving signals produced in response to said scanning of said surface and for processing said signals to provide an output;

b) means for storing a database of previously stored images; and c) system processor means having inputs coupled to said database storage means and to the output of said processor means for comparing a scanned image from said ultrasonic imaging system to the previously stored images in said database storage means to determine if a match exists.

90. A system according to claim 89, further including data buffer means connected between the output of said signal processor means and said system processor means so that said ultrasonic imaging system can scan said surface at a relatively fast rate independent of the rate at which said system processor means reads data from said data buffer means.

91. A system according to claim 89, in combination with another ultrasonic imaging system, database storage means and system processor means together with local area network means for connecting said first-named system processor means and said another system processor means together.

92. A system according to claim 89, further including means for providing a wireless communication link between said ultrasonic imaging system and said system processor means.

93. A biometric identification system comprising:

a) a first ultrasonic imaging system for imaging human or animal tissue having a surface and comprising probe means including means for defining said surface in a manner supporting said human or animal tissue for imaging the same, transducer means positioned closely adjacent said supporting means for providing an output ultrasonic beam directed on said surface so that the size of said beam at its focal point is as small as possible to maximize the resolution of said system, said imaging system further comprising control means operatively connected to said probe means for controlling scanning of said surface by said transducer means and signal processor means operatively connected to said probe means for receiving signals produced in response to said scanning of said surface and for processing said signals to provide an output;

b) first means for storing a database of previously stored images;

c) first system processor means having inputs coupled to said database storage means and to the output of said processor means for comparing a scanned image from said ultrasonic imaging system to the previously stored images in said database storage means to determine if a match exists;

d) a second ultrasonic imaging system providing an output;

e) second means for storing a database of previously stored images;

f) second system processor means having inputs coupled to said second database storage means and to the output of said second ultrasonic imaging system for comparing a scanned image from the output of said second ultrasonic imaging system to the previously stored images in said second database storage means to determine if a match exists; and g) local area network means for connecting said first and second system processor means together.

94. A biometric identification system comprising:

a) an ultrasonic imaging system for imaging human or animal tissue having a surface and comprising probe means including means for defining said surface in a manner supporting said human or animal tissue for imaging the same, transducer means positioned closely adjacent said supporting means for providing an output ultrasonic beam directed on said surface so that the size of said beam at its focal point is as small as possible to maximize the resolution of said system, said imaging system further comprising control means operatively connected to said probe means for controlling scanning of said surface by said transducer means and signal processor means operatively connected to said probe means for receiving signals produced in response to said scanning of said surface and for processing said signals to provide an output;

b) means for storing a database of previously stored images;

c) system processor means having inputs coupled to said database storage means and to the output of said processor means for comparing a scanned image from said ultrasonic imaging system to the previously stored images in said database storage means to determine if a match exists; and d) means for providing a wireless communication link between said ultrasonic imaging system and said system processor means.

* * * * *

UNITED STATES PATENT AND TRADEMARK OFFICE
CERTIFICATE OF CORRECTION

PATENT NO. : 5,456,256
DATED : October 10, 1995
INVENTOR(S) : John K. Schneider et al It is certified that error appears in the above-identified patent and that said Letters Patent is hereby corrected as shown below:

Column 31, line 10
Claim 21, line 15 - change "date" to --data--.
Column 31, line 30
Claim 23, line 16 - after "surface;" insert --and--.
Column 33, line 35
Claim 33, line 16 - after "surface;" insert --and--.
Column 35, line 54
Claim 41, line 12 - after "system;" insert --and--.
Column 37, line 30

Claim 83, line 8 - after "transducers;" delete --and--.

Signed and Sealed this

Nineteenth Day of November, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,456,256
DATED : October 10, 1995
INVENTOR(S) : John K. Schneider, et al It is certified that error appears in the above-indentified patent and that said Letters Patent is hereby corrected as shown below:

Column 37, line 30, claim 56, change "53" to --50--.

Signed and Sealed this

Eleventh Day of March, 1997

Attest:

BRUCE LEHMAN

Attesting Officer

Commissioner of Patents and Trademarks